US011123404B2

(12) United States Patent
Cohen et al.

(10) Patent No.: US 11,123,404 B2
(45) Date of Patent: Sep. 21, 2021

(54) METHODS FOR GENERATING IMMUNOTOLERANT RESPONSES

(71) Applicant: B. G. Negev Technologies and Applications Ltd., at Ben-Gurion University, Beer Sheva (IL)

(72) Inventors: Smadar Cohen, Beer Sheva (IL); Alon Monsonego, Moshav Nir-Banim (IL)

(73) Assignee: B. G. NEGEV TECHNOLOGIES AND APPLICATIONS LTD., AT BEN-GURION UNIVERSITY, Beer Sheva (IL)

( * ) Notice: Subject to any disclaimer, the term of this patent is extended or adjusted under 35 U.S.C. 154(b) by 102 days.

(21) Appl. No.: 16/068,133

(22) PCT Filed: Jan. 5, 2017

(86) PCT No.: PCT/IL2017/050013
§ 371 (c)(1),
(2) Date: Jul. 5, 2018

(87) PCT Pub. No.: WO2017/118979
PCT Pub. Date: Jul. 13, 2017

(65) Prior Publication Data
US 2019/0008924 A1    Jan. 10, 2019

Related U.S. Application Data

(60) Provisional application No. 62/275,827, filed on Jan. 7, 2016.

(51) Int. Cl.
| | | |
|---|---|---|
| A61K 38/18 | (2006.01) | |
| A61K 31/737 | (2006.01) | |
| A61K 47/61 | (2017.01) | |
| A61P 37/06 | (2006.01) | |
| A61P 3/10 | (2006.01) | |
| A61K 45/06 | (2006.01) | |
| A61K 47/36 | (2006.01) | |
| A61K 9/06 | (2006.01) | |
| A61K 9/00 | (2006.01) | |

(52) U.S. Cl.
CPC ........ *A61K 38/1841* (2013.01); *A61K 31/737* (2013.01); *A61K 38/1866* (2013.01); *A61K 45/06* (2013.01); *A61K 47/61* (2017.08); *A61P 3/10* (2018.01); *A61P 37/06* (2018.01); *A61K 9/0024* (2013.01); *A61K 9/06* (2013.01); *A61K 47/36* (2013.01); *Y02A 50/30* (2018.01)

(58) Field of Classification Search
None
See application file for complete search history.

(56) References Cited

U.S. PATENT DOCUMENTS

| | | |
|---|---|---|
| 4,178,361 A | 12/1979 | Cohen et al. |
| 6,334,968 B1 | 1/2002 | Shapiro et al. |
| 6,388,060 B1 | 5/2002 | Guo et al. |
| 6,425,918 B1 | 7/2002 | Shapiro et al. |
| 6,479,064 B1 | 11/2002 | Atala |
| 6,773,723 B1 | 8/2004 | Spiro et al. |
| 6,793,675 B2 | 9/2004 | Shapiro et al. |
| 7,517,856 B2 | 4/2009 | Cohen et al. |
| 7,642,240 B2 | 1/2010 | Cohen et al. |
| 8,609,126 B2 | 12/2013 | Michal et al. |
| 8,852,637 B2 | 10/2014 | Naughton et al. |
| 2005/0169941 A1 | 8/2005 | Lees |
| 2007/0081976 A1 | 4/2007 | Cohen et al. |
| 2009/0053249 A1 | 2/2009 | Qi et al. |
| 2010/0247652 A1 | 9/2010 | Ilan et al. |
| 2011/0212501 A1 | 9/2011 | Yoo |
| 2012/0321665 A1 | 12/2012 | Bollyky et al. |

FOREIGN PATENT DOCUMENTS

| | | |
|---|---|---|
| EP | 1886696 | 2/2008 |
| EP | 1428871 B1 | 8/2008 |
| EP | 2174656 A2 | 4/2010 |
| WO | WO 1989/012464 | 12/1989 |
| WO | WO 1999/021588 A1 | 5/1999 |
| WO | WO 2000/064481 | 11/2000 |
| WO | WO 2001/066164 | 9/2001 |
| WO | WO 2002/46374 A1 | 6/2002 |
| WO | WO 2003/072764 A1 | 9/2003 |
| WO | WO 2005/035726 A2 | 4/2005 |
| WO | WO 2007/043050 A2 | 7/2008 |
| WO | WO 2008/082766 A2 | 7/2008 |
| WO | WO 2011/078990 A1 | 6/2011 |
| WO | WO 2011/163568 A1 | 12/2011 |
| WO | WO 2012/113812 | 8/2012 |

(Continued)

OTHER PUBLICATIONS

Devaux et al., Induction of EAE in mice with recombinant human MOG, and treatment of EAE with a MOG peptide. J. Neuroimmunol. 75, 169-173, 1997. (Year: 1997).*

Akashi et al. "Synthesis and anticoagulant activity of sulfated glucoside-bearing polymer" Bioconjug Chem. Jul.-Aug. 1996;7(4):393-5.

Amara et al. "Stromal cell-derived factor-1alpha associates with heparan sulfates through the first beta-strand of the chemokine" J Biol Chem. Aug. 20, 1999;274(34):23916-25.

Arlov et al. "Sulfated alginates as heparin analogues: a review of chemical and functional properties" Molecules. 2017;22(5):778.

(Continued)

*Primary Examiner* — Elly-Gerald Stoica
(74) *Attorney, Agent, or Firm* — Mark S. Cohen; Pearl Cohen Zedek Latzer Baratz LLP

(57) ABSTRACT

The invention relates generally to compositions and methods for generating immunotolerant responses in a subject. Specifically, the invention relates to a composition comprising a sulfated polysaccharide and a bioactive polypeptide for generating an immunotolerant response.

18 Claims, 38 Drawing Sheets

Specification includes a Sequence Listing.

(56) References Cited

FOREIGN PATENT DOCUMENTS

WO  WO 2013/124855 A1  8/2013
WO  WO 2017/175229 A1  10/2017

OTHER PUBLICATIONS

Bondalapati et al. "Rapid end-group modification of polysaccharides for biomaterial applications in regenerative medicine" Macromolecular rapid communications. Oct. 2014;35(20):1754-62.
Bonner-Weir et al. "In vitro cultivation of human islets from expanded ductal tissue" Proceedings of the National Academy of Sciences. Jul. 5, 2000;97(14):7999-8004.
Bowers et al. "Advances in local drug release and scaffolding design to enhance cell therapy for diabetes" Tissue Engineering Part B: Reviews. Oct. 26, 2015;21(6):491-503.
Brill et al. "Expansion conditions for early hepatic progenitor cells from embryonal and neonatal rat livers" Digestive diseases and sciences. Feb. 1, 1999;44(2):364-71.
Brunk et al. "Assay for nanogram quantities of DNA in cellular homogenates" Analytical biochemistry. Jan. 15, 1979;92(2):497-500.
Capila et al. "Heparin-protein interactions" Angewandte Chemie International Edition. Feb. 1, 2002;41(3):390-412.
Chung et al. "A facile method to prepare heparin-functionalized nanoparticles for controlled release of growth factors" Biomaterials. Apr. 1, 2006;27(12):2621-6.
Cochran et al. "Probing the interactions of phosphosulfomannans with angiogenic growth factors by surface plasmon resonance" J Med Chem. Oct. 9, 2003;46(21):4601-8.
Cohen et al. "Direct freeform fabrication of seeded hydrogels in arbitrary geometries" Tissue Eng. May 2006;12(5):1325-35.
Crawford et al. "An autologous cartilage tissue implant NeoCart for treatment of grade III chondral injury to the distal femur: prospective clinical safety trial at 2 years" The American journal of sports medicine, Jul. 2009;37(7):1334-43.
Cusick et al. "The effect of donor and recipient age on engraftment of tissue-engineered liver" Journal of pediatric surgery. Feb. 1, 1997;32(2):357-60.
Dabeva et al. "Proliferation and differentiation of fetal liver epithelial progenitor cells after transplantation into adult rat liver" The American journal of pathology. Jun. 1, 2000;156(6):2017-31.
Dodgson et al. "A note on the determination of the ester sulphate content of sulphated polysaccharides" Biochem J. Jul. 1962;84:106-10.
Dvir et al. "Prevascularization of cardiac patch on the omentum improves its therapeutic outcome" Proc Natl Acad Sci U S A. Sep. 1, 2009;106(35):14990-5.
Dvir-Ginzberg et al. "Induced differentiation and maturation of newborn liver cells into functional hepatic tissue in macroporous alginate scaffolds" The FASEB Journal. May 2008;22(5):1440-9.
Dvir-Ginzberg et al. "Liver tissue engineering within alginate scaffolds: effects of cell-seeding density on hepatocyte viability, morphology, and function" Tissue engineering. Aug. 1, 2003;9(4):757-66.
Dvir-Ginzberg et al. "Ultrastructural and functional investigations of adult hepatocyte spheroids during in vitro cultivation" Tissue engineering. Nov. 1, 2004;10(11-12):1806-17.
Ehashi et al. "Oncostatin M stimulates proliferation and functions of mouse fetal liver cells in three-dimensional cultures" Journal of cellular physiology. Mar. 2005;202(3):698-706.
Elisseeff J. Regenerating organized tissues and understanding cell-cell interactions. In FASEB Journal Mar. 23, 2004 (vol. 18, No. 4, pp. A405-A406), Abstract.
Elkayam et al. "Enhancing the drug metabolism activities of C3A—a human hepatocyte cell line—by tissue engineering within alginate scaffolds" Tissue engineering. May 1, 2006;12(5):1357-68.
Faris et al. "Liver stem cells: a potential source of hepatocytes for the treatment of human liver disease"glick Artificial organs. Jul. 1, 2001;25(7):513-21.

Freeman et al. "The influence of the sequential delivery of angiogenic factors from affinity-binding alginate scaffolds on vascularization" Biomaterials. Apr. 1, 2009;30(11):2122-31.
Freeman et al. "The effect of sulfation of alginate hydrogels on the specific binding and controlled release of heparin-binding proteins" Biomaterials. Aug. 1, 2008;29(22):3260-8.
Freeman et al. "Abstract Book of the Joint Meeting of the Tissue Engineering Society International and the European Tissue Engineering Society", Oct. 13, 2004, XP007923141.
Garanger et al. "New multifunctional molecular conjugate vector for targeting, imaging, and therapy of tumors" Molecular Therapy. Dec. 1, 2005;12(6):1168-75.
Genbank Accession No. X02812, Feb. 2, 2011, Version1.
Geresh et al. "Sulfation of extracellular polysaccharides of red microalgae: preparation, characterization and propert" J Biochem Biophys Methods. Jan. 4, 2002;50(2-3):179-87.
Glicklis et al. "Hepatocyte behavior within three-dimensional porous alginate scaffolds" Biotechnology and bioengineering. Feb. 5, 2000;67(3):344-53.
Glicklis et al. "Modeling mass transfer in hepatocyte spheroids via cell viability, spheroid size, and hepatocellular functions" Biotechnology and bioengineering. Jun. 20, 2004;86(6):672-80.
Goodell et al. "Isolation and functional properties of murine hematopoietic stem cells that are replicating in vivo" Journal of Experimental Medicine. Apr. 1, 1996;183(4):1797-806.
Goretzki et al. "High-affinity binding of basic fibroblast growth factor and platelet-derived growth factor-AA to the core protein of the NG2 proteoglycan" J Biol Chem. Jun. 11, 1999;274(24):16831-7.
Gotterbarm et al. "An in vivo study of a growth-factor enhanced, cell free, two-layered collagen-tricalcium phosphate in deep osteochondral defects" Biomaterials. Jun. 1, 2006;27(18):3387-95.
Habuchi et al. "Structure of a heparan sulphate oligosaccharide that binds to basic fibroblast growth factor" Biochem J. Aug. 1, 1992;285 ( Pt 3):805-13.
Hansen et al. "Integrin binding and cell spreading on extracellular matrix act at different points in the cell cycle to promote hepatocyte growth" Molecular Biology of the Cell. Sep. 1994;5(9):967-75.
International Search Report for PCT Application No. PCT/IL2017/050013 dated Apr. 2, 2017.
Jabbari E. "Engineering bone formation with peptidomimetic hybrid biomaterials" In 2009 Annual International Conference of the IEEE Engineering in Medicine and Biology Society Sep. 3, 2009 (pp. 1172-1175). IEEE.
Jiang et al. "Efficacy of engineered liver tissue based on poly-L-lactic acid scaffolds and fetal mouse liver cells cultured with oncostatin M, nicotinamide, and dimethyl sulfoxide" Tissue engineering. Sep. 1, 2004:10(9-10):1577-88.
Junker et al. "Effect of adhesion factors fibronectin, laminin, and type IV collagen on spreading and growth of transformed and control rat liver epithelial cells" Cancer research. Jul. 15, 1987;47(14):3802-7.
Kamei et al. "The analysis of heparin-protein interactions using evanescent wave biosensor with regioselectively desulfated heparins as the ligands" Anal Biochem. Aug. 15, 2001;295(2):203-13.
Kamiya et al. "Maturation of fetal hepatocytes in vitro by extracellular matrices and oncostatin M: induction of tryptophan oxygenase" Hepatology. Jun. 1, 2002;35(6):1351-9.
Karp et al. "Mesenchymal stem cell homing: the devil is in the details" Cell Stem Cell. Mar. 6, 2009;4(3):206-16.
Kock et al. "Tissue engineering of functional articular cartilage: the current status" Cell Tissue Res. Mar. 2012;347(3):613-27.
Kohan et al. "Osteopontin induces airway remodeling and lung fibroblast activation in a murine model of asthma" Am J Respir Cell Mol Biol. Sep. 2009;41(3):290-6.
Kozawa et al. "Divergent regulation by p44/p42 MAP kinase and p38 MAP kinase of bone morphogenetic protein-4-stimulated osteocalcin synthesis in osteoblasts" J Cell Biochem. 2002;84(3):583-9.
Kreuger et al. Characterization of fibroblast growth factor 1 binding heparan sulfate domain Glycobiology. Jul. 1999;9(7):723-9.
Laird et al. "Stem cell trafficking in tissue development, growth, and disease" Cell. Feb. 22, 2008;132(4):612-30.

(56) References Cited

OTHER PUBLICATIONS

Lang et al. "Tamarind seed polysaccharide: preparation, characterisation and solution properties of carboxylated, sulphated and alkylaminated derivatives". Carbohydrate polymers. Dec. 31, 1992;17(3):185-98.
Lázaro et al. "Establishment, characterization, and long-term maintenance of cultures of human fetal hepatocytes" Hepatology. Nov. 2003;38(5):1095-106.
Lees et al. "Versatile and efficient synthesis of protein-polysaccharide conjugate vaccines using aminooxy reagents and oxime chemistry" Vaccine. Feb. 6, 2006;24(6):716-29.
"Lduronic Acid"; downloaded from: en.wikipedia.org/wiki/lduronic_acid.
Levy et al. "Signal transducer and activator of transcription 3-A key molecular switch for human mesenchymal stem cell proliferation" Int J Biochem Cell Biol. 2008;40(11):2606-18.
Levy et al. "Highly efficient osteogenic differentiation of human mesenchymal stem cells by eradication of STAT3 signaling" Int J Biochem Cell Biol. Nov. 2010;42(11):1823-30.
Liu et al. "Biomaterials Transforming growth factor-beta 1 delivery from microporous scaffolds decreases inflammation post-implant and enhances function of transplanted islets" Biomaterials. Feb. 1, 2016;80:11-9.
Ma et al. "Core-shell hydrogel microcapsules for improved islets encapsulation" Advanced healthcare materials. May 2013;2(5):667-72.
Majka et al. "Numerous growth factors, cytokines, and chemokines are secreted by human CD34+ cells, myeloblasts, erythroblasts, and megakaryoblasts and regulate normal hematopoiesis in an autocrine/paracrine manner" Presented at the 41st Annual Meeting of the American Society of Hematology, New Orleans, LA, Dec. 3-7, 1999, and published in abstract form in Blood. 1999; 94 (suppl 1): 465a. Blood. May 15, 2001;97(10):3075-85.
Marcacci et al. "Articular Cartilage Engineering with Hyalograft (R) C: 3-Year Clinical Results" Clinical Orthopaedics and Related Research (1976-2007). Jun. 1, 2005;435:96-105.
Michalopoulos et al. "Hepatocytes undergo phenotypic transformation to biliary epithelium in organoid cultures" Hepatology. Aug. 1, 2002;36(2):278-83.
Michalopoulos et al. "Liver regeneration" Science. Apr. 4, 1997;276(5309):60-6.
Miller et al. "Experimental autoimmune encephalomyelitis in the mouse." Current protocols in immunology. Feb. 2010;88(1):15-.
Mooney et al. "Switching from differentiation to growth in hepatocytes: control by extracellular matrix"oja Journal of cellular physiology. Jun. 1992;151(3):497-505.
Ng et al. "Zonal chondrocytes seeded in a layered agarose hydrogel create engineered cartilage with depth-dependent cellular and mechanical inhomogeneity" Tissue Eng Part A. Sep. 2009;15(9):2315-24.
Nixon et al. "Enhanced repair of extensive articular defects by insulin-like growth factor-I-laden fibrin composites" Journal of Orthopaedic Research. Jul. 1999;17(4):475-87.
Ojakian et al. "Regulation of epithelial cell surface polarity reversal by beta 1 integrins" Journal of cell science. Mar. 1, 1994;107(3):561-76.
"Organoid" definition; accessed at: http://medical-dictionary.thefreedictionary.com/p/organoid, Mosby's Medical Dictionary, accessed Jul. 2012.
Orr et al. "TGF-β affinity-bound to a macroporous alginate scaffold generates local and peripheral immunotolerant responses and improves allocell transplantation" Acta biomaterialia. Nov. 1, 2016;45:196-209.
Paredes et al. "Mechanisms responsible for catalysis of the inhibition of factor Xa or thrombin by antithrombin using a covalent antithrombin-heparin complex" J Biol Chem. Jun. 27, 2003;278(26):23398-409.
Polyak et al. "Synthesis and characterization of a biotin-alginate conjugate and its application in a biosensor construction" Biomacromolecules. Mar.-Apr. 2004;5(2):389-96.

Prockop "Repair of tissues by adult stem/progenitor cells (MSCs): controversies, myths, and changing paradigms" Mol Ther. Jun. 2009;17(6):939-46.
Qi et al. "Identification of genes responsible for osteoblast differentiation from human mesodermal progenitor cells" Proc Natl Acad Sci U S A. Mar. 18, 2003;100(6):3305-10.
Rahmoune et al. "Hepatocyte growth factor/scatter factor has distinct classes of binding site in heparan sulfate from mammary cells" Biochemistry. Apr. 28, 1998;37(17):6003-8.
Re'em et al. "Chondrogenesis of hMSC in affinity-bound TGF-beta scaffolds" Biomaterials. Jan. 1, 2012;33(3):751-61.
Re'em et al. "Simultaneous regeneration of articular cartilage and subchondral bone induced by spatially presented TGF-beta and BMP-4 in a bilayer affinity binding system" Acta biomaterialia. Sep. 1, 2012;8(9):3283-93.
Renaudet et al. "Chemoselectively template-assembled glycoconjugates as mimics for multivalent presentation of carbohydrates" Organic letters. Feb. 6, 2003;5(3):243-6.
Richert et al. "Evaluation of the effect of culture configuration on morphology, survival time, antioxidant status and metabolic capacities of cultured rat hepatocytes" Toxicology in vitro. Feb. 1, 2002;16(1):89-99.
Risbud et al. "Hydrogel-coated textile scaffolds as candidate in liver tissue engineering: II. Evaluation of spheroid formation and viability of hepatocytes" Journal of Biomaterials Science, Polymer Edition. Jan. 1, 2003;14(7):719-31.
Ruvinov et al. "The effects of controlled HGF delivery from an affinity-binding alginate biomaterial on angiogenesis and blood perfusion in a hindlimb ischemia model" Biomaterials. Jun. 2010;31(16):4573-82.
Ruvinov et al. "The promotion of myocardial repair by the sequential delivery of IGF-1 and HGF from an injectable alginate biomaterial in a model of acute myocardial infarction" Biomaterials. Jan. 2011;32(2):565-78.
Sandhu et al. "Stem cell properties and repopulation of the rat liver by fetal liver epithelial progenitor cells" The American journal of pathology. Oct. 1, 2001;159(4):1323-34.
Schaefer et al. "Tissue-engineered composites for the repair of large osteochondral defects" Arthritis & Rheumatism. Sep. 2002;46(9):2524-34.
Schroeder-Tefft et al. "Collagen and Heparin Matrices for Growth Factor Delivery" Journal of Controlled Release, vol. 48, 1997, pp. 29-33, XP002088404.
Schubart UK. "Regulation of gene expression in rat hepatocytes and hepatoma cells by insulin: quantitation of messenger ribonucleic acid's coding for tyrosine aminotransferase, tryptophan oxygenase, and phosphoenolpyruvate carboxykinase" Endocrinology. Oct. 1, 1986;119(4):1741-9.
Schwartz et al. "Muitipotent adult progenitor cells from bone marrow differentiate into functional hepatocyte-like cells" The Journal of clinical investigation. May 15, 2002;109(10):1291-302.
Selden et al. "Three-dimensional in vitro cell culture leads to a marked upregulation of cell function in human hepatocyte cell lines—an important tool for the development of a bioartificial liver machine" Annals of the New York Academy of Sciences. Jun. 1999;875(1):353-63.
Sestak et al. "Single-step grafting of aminooxy-peptides to hyaluronan: a simple approach to multifunctional therapeutics for experimental autoimmune encephalomyelitis" Journal of controlled release. Jun. 28, 2013;168(3):334-40.
Shachar et al. "The effect of immobilized RGD peptide in alginate scaffolds on cardiac tissue engineering" Acta biomaterialia. Jan. 1, 2011;7(1):152-62.
Shao et al. "Evaluation of a hybrid scaffold/cell construct in repair of high-load-bearing osteochondral defects in rabbits" Biomaterials. Mar. 1, 2006;27(7):1071-80.
Shapiro et al. "Novel alginate sponges for cell culture and transplantation" Biomaterials. Apr. 1997;18(8):583-90.
Shimano et al. "Hepatic oval cells have the side population phenotype defined by expression of ATP-binding cassette transporter ABCG2/BCRP1" The American journal of pathology. Jul. 1, 2003;163(1):3-9.

(56) References Cited

OTHER PUBLICATIONS

Song et al. "Overlap of IGF- and heparin-binding sites in rat IGF-binding protein-5" J Mol Endocrinol. Feb. 2000;24(1):43-51.
Sugimoto et al. "Hepatic organoid formation in collagen sponge of cells isolated from human liver tissues" Tissue engineering. Mar. 1, 2005;11(3-4):626-33.
Supplementary European Search Report for European Application No. 17735926.2 dated Jun. 6, 2019.
Tzanakakis et al. "Probing enhanced cytochrome P450 2B1/2 activity in rat hepatocyte spheroids through confocal laser scanning microscopy" Cell Transplantation. Apr. 2001;10(3):329-42.
Ulrich et al. "Oxime ligation: a chemoselective click-type reaction for accessing multifunctional biomolecular constructs" Chemistry—A European Journal. Jan. 3, 2014;20(1):34-41.
Weadock et al. "Effect of physical crosslinking methods on collagen-fiber durability in proteolytic solutions" Journal of Biomedical Materials Research: An Official Journal of The Society for Biomaterials and The Japanese Society for Biomaterials. Oct. 1996;32(2):221-6.

Wijelath et al. "Novel vascular endothelial growth factor binding domains of fibronectin enhance vascular endothelial growth factor biological activity" Circ Res. Jul. 12, 2002;91(1):25-31.
Wu et al. "Surface plasmon resonance analysis to evaluate the importance of heparin sulfate groups' binding with human aFGF and bFGF" J Zhejiang Univ Sci. Jan.-Feb. 2003;4(1):86-94.
Wu et al. "Enhanced cytochrome P450 IA1 activity of self-assembled rat hepatocyte spheroids" Cell transplantation. May 1999;8(3):233-46.
Yin et al. "VEGF-conjugated alginate hydrogel prompt angiogenesis and improve pancreatic islet engraftment and function in type 1 diabetes" Materials Science and Engineering: C. Feb. 1, 2016;59:958-64.
Zhang et al. "Inhibition of angiogenesis is associated with reduced islet engraftment in diabetic recipient mice" In Transplantation proceedings Dec. 1, 2005 (vol. 37, No. 10, pp. 4452-4457). Elsevier.
Zhang et al. "A highly stable covalent conjugated heparin biochip for heparin-protein interaction studies" Anal Biochem. May 15, 2002;304(2):271-3.
Zmora et al. "Tailoring the pore architecture in 3-D alginate scaffolds by controlling the freezing regime during fabrication" Biomaterials. Oct. 1, 2002;23(20):4087-94.

* cited by examiner

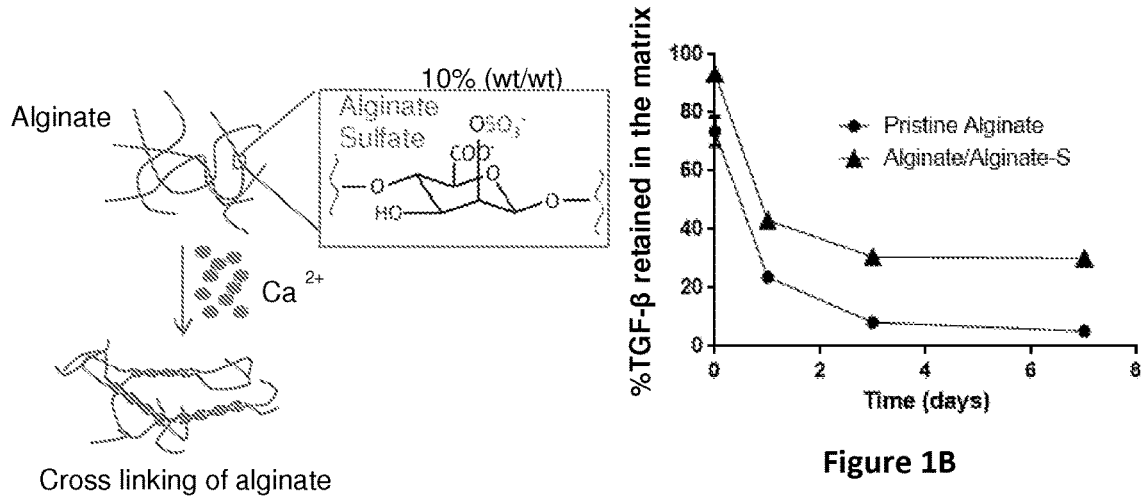
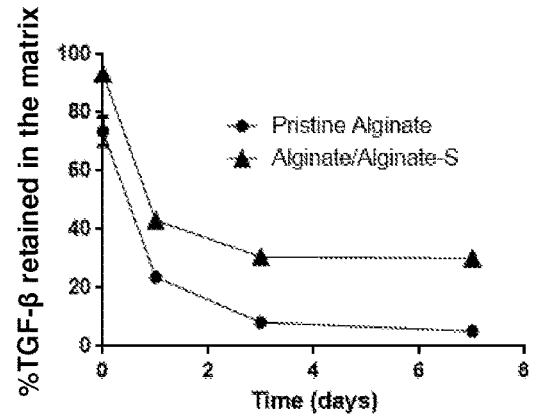
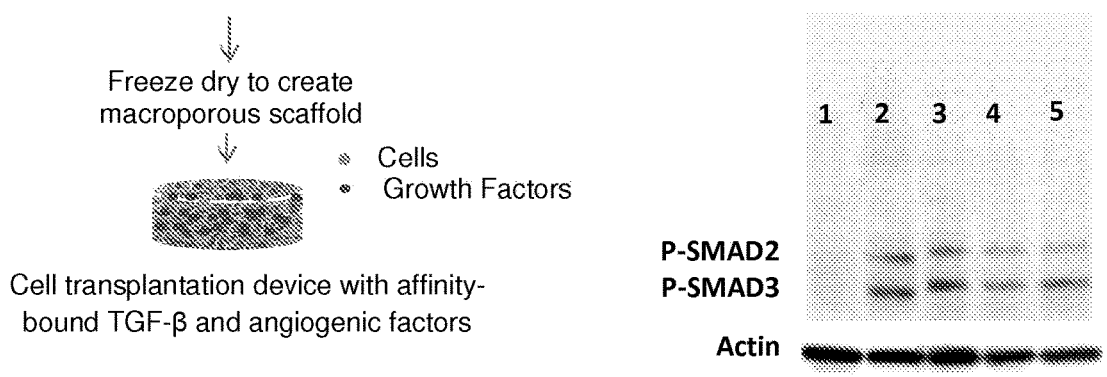
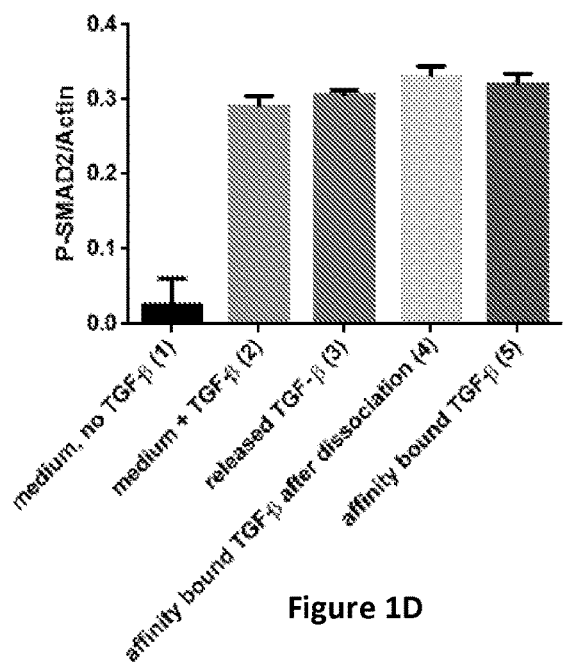
Figure 1A
Figure 1B
Figure 1C
Figure 1D

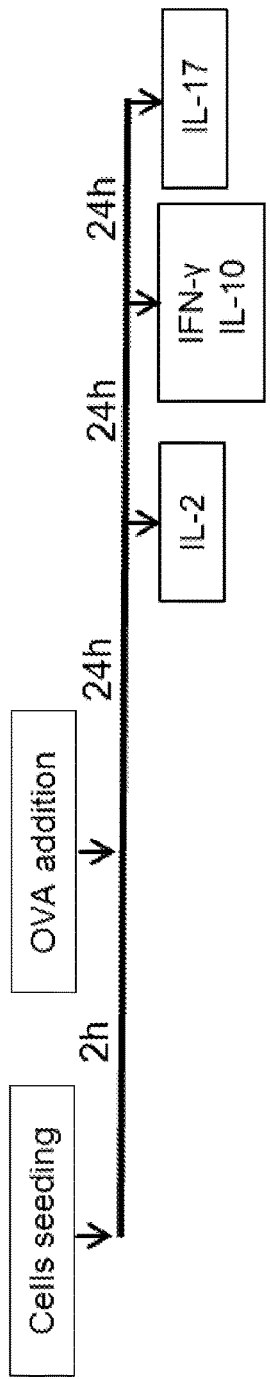
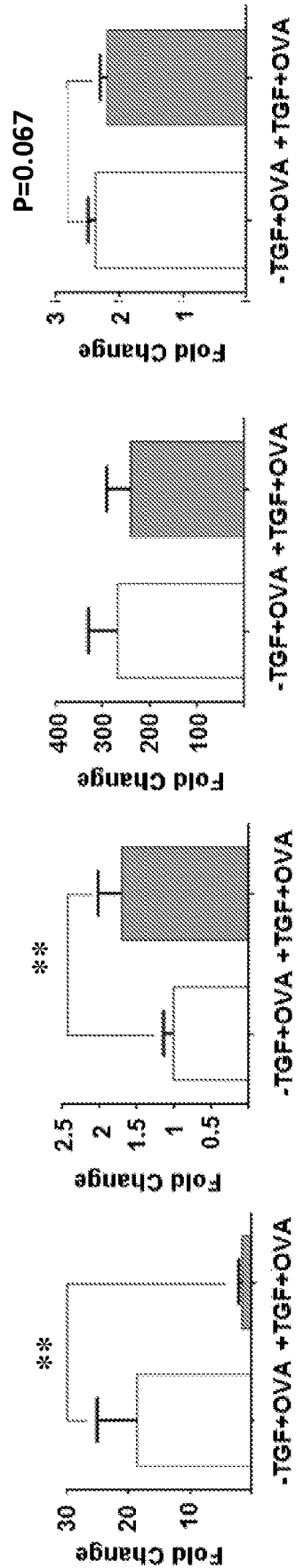
Figure 2A
Figure 2B
Figure 2C
Figure 2D
Figure 2E

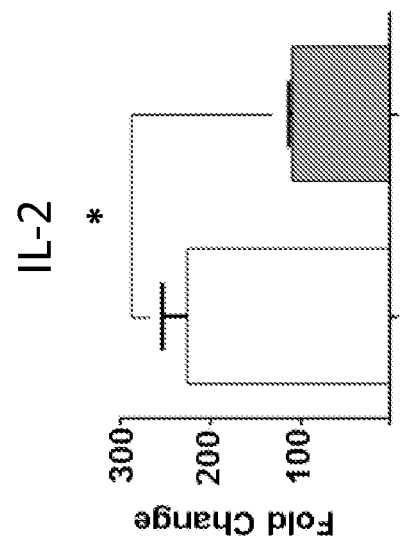
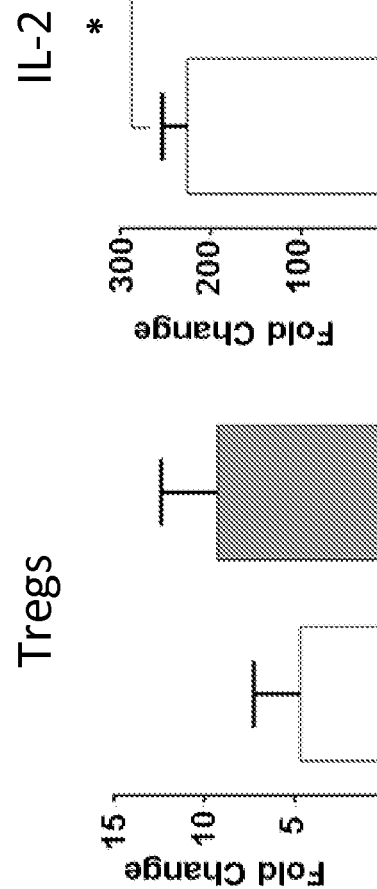
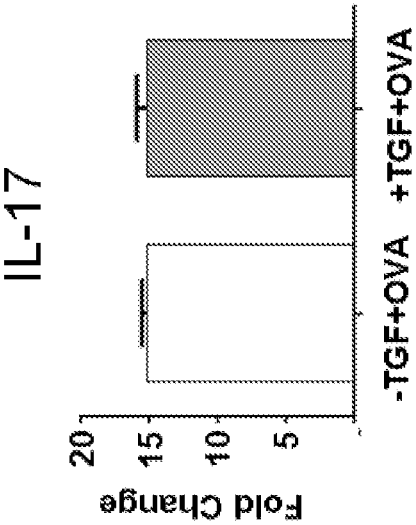
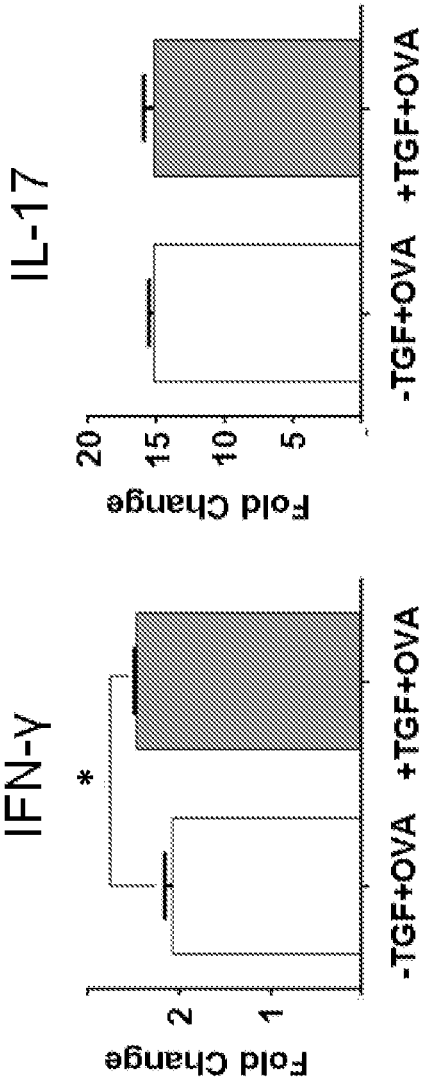
Figure 5C
Figure 5D
Figure 5E
Figure 5F

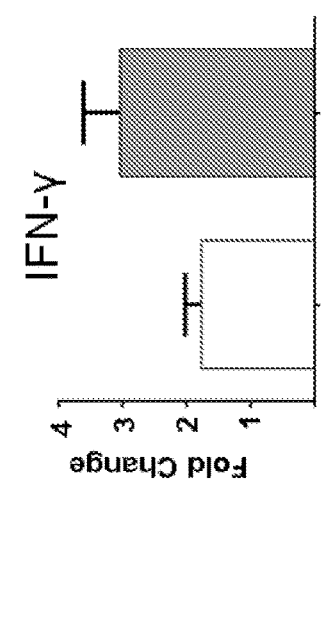
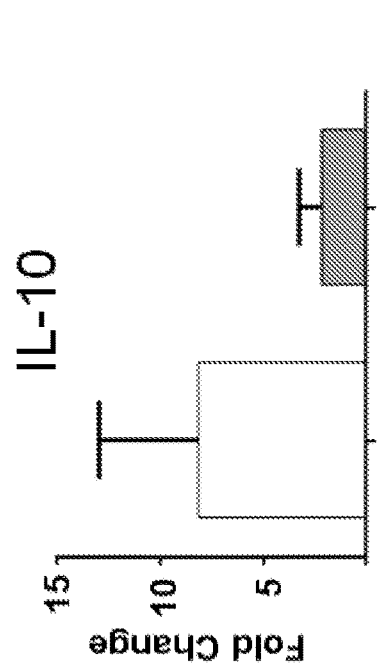
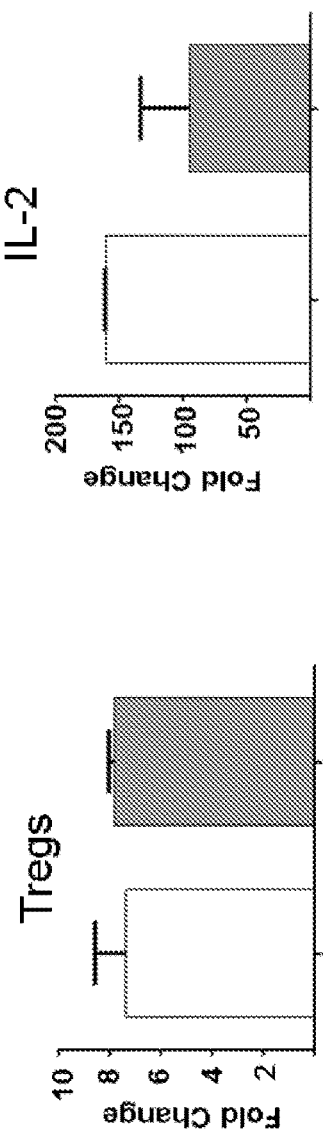
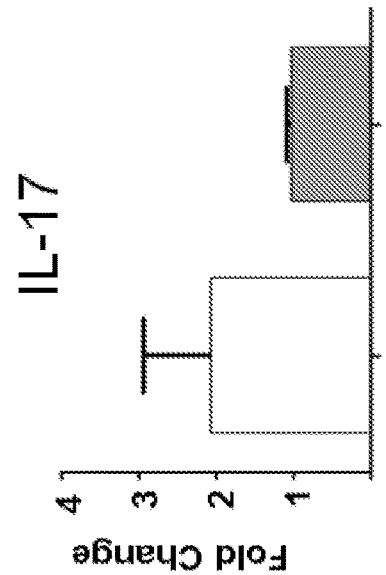
Figure 6A
Figure 6B
Figure 6C
Figure 6D
Figure 6E

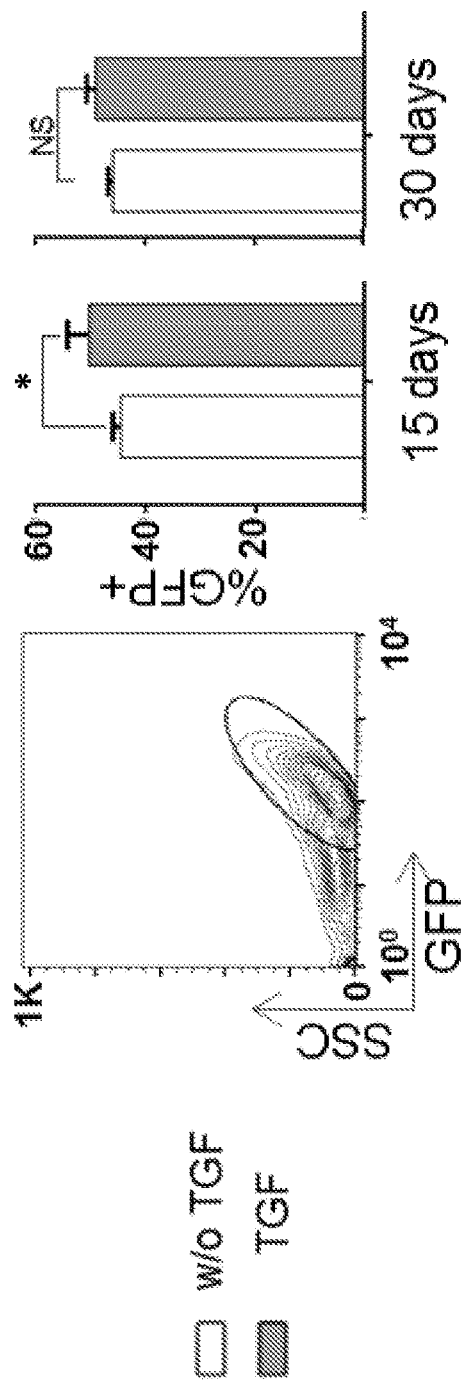
Figure 10A
Figure 10B
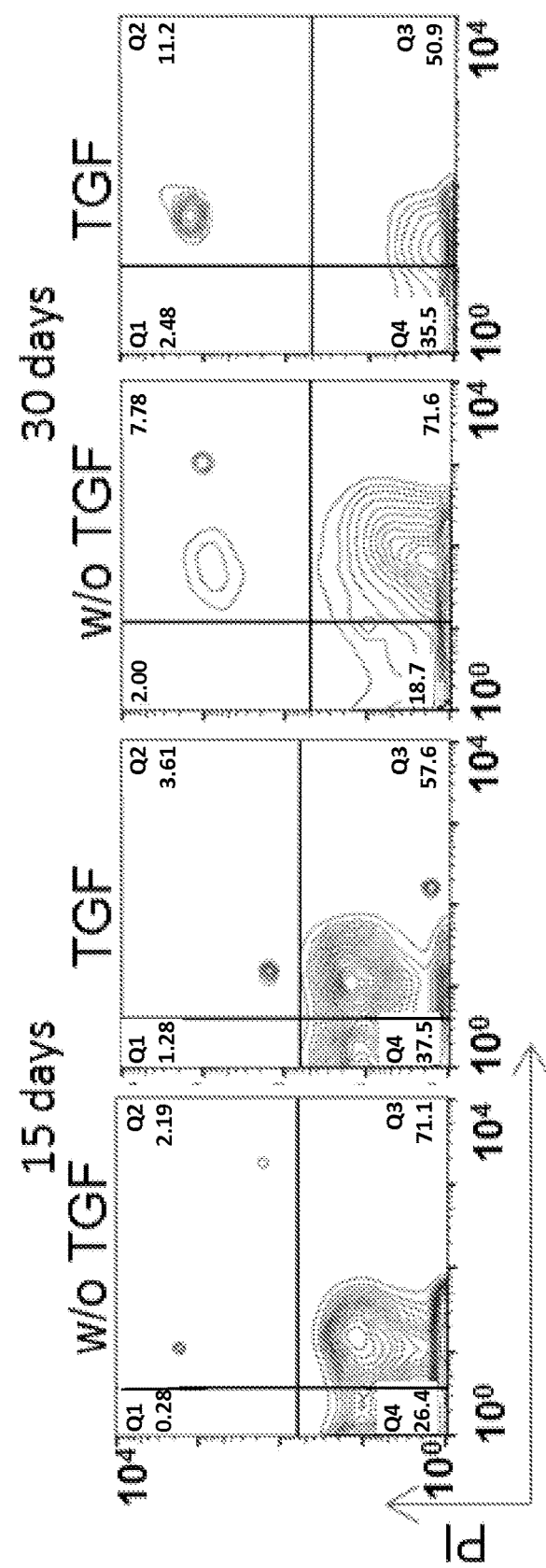
Figure 10C

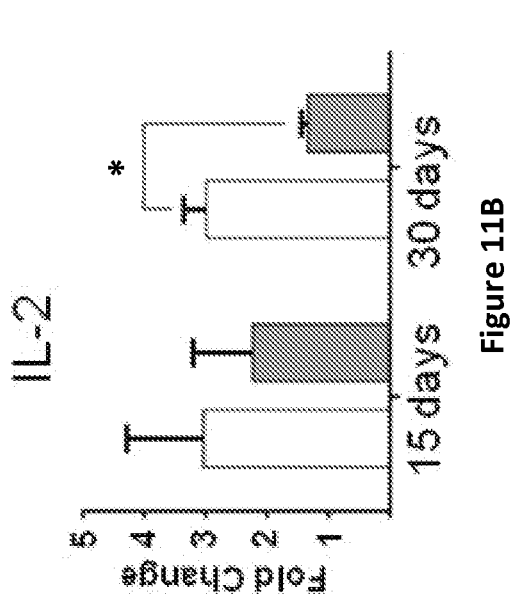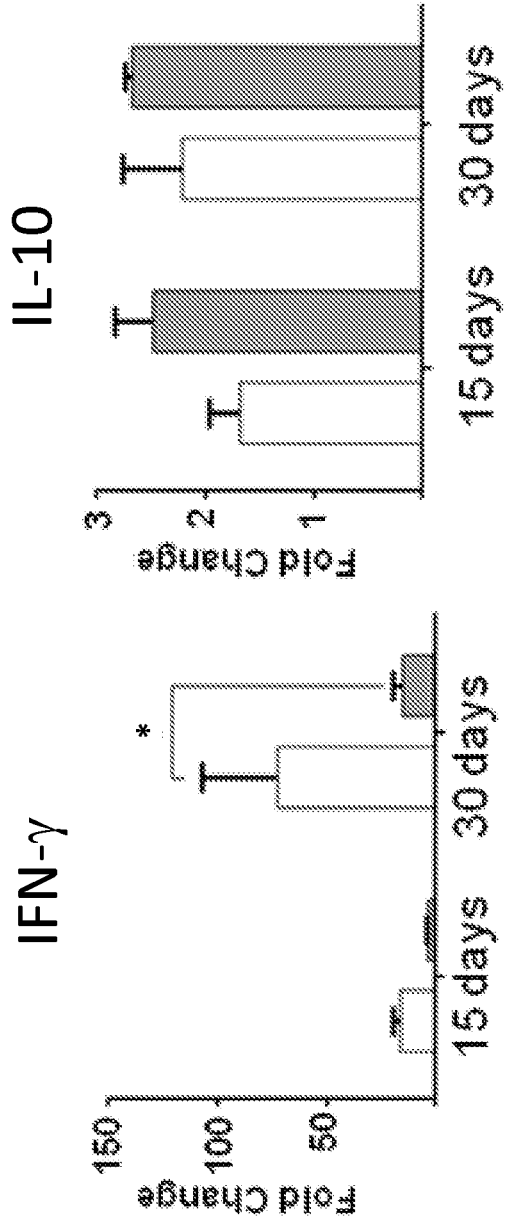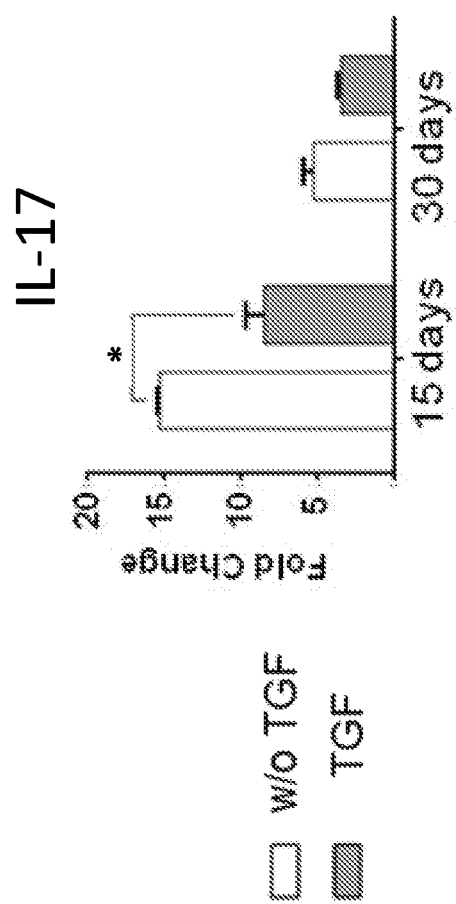
Figure 11A, Figure 11B, Figure 11C, Figure 11D

SEQUENCE LISTING

<160> NUMBER OF SEQ ID NOS: 1

<210> SEQ ID NO 1
<211> LENGTH: 21
<212> TYPE: PRT
<213> ORGANISM: Mus musculus

<400> SEQUENCE: 1

```
Met Glu Val Gly Trp Tyr Arg Ser Pro Phe Ser Arg Val Val His Leu
1               5                   10                  15

Tyr Arg Asn Gly Lys
            20
```

METHODS FOR GENERATING IMMUNOTOLERANT RESPONSES

CROSS-REFERENCE TO RELATED APPLICATIONS

This application is a National Phase Application of PCT International Application No. PCT/IL2017/050013, which was filed on Jan. 5, 2017, claiming priority to U.S. Patent Application No. 62/275,827, filed Jan. 7, 2016, which is hereby incorporated by reference in its entirety.

FIELD OF THE INVENTION

The invention relates generally to compositions and methods for generating immunotolerant responses in a subject. Specifically, the invention relates to a composition comprising a sulfated polysaccharide and a bioactive polypeptide for generating an immunotolerant response.

BACKGROUND OF THE INVENTION

Preventing cell allograft rejection is a major challenge in current cell therapy strategies. Such a rejection is mediated by allograft-reactive effector CD4 and CD8 T cells. Lifelong treatment with immunosuppressive drugs can attenuate alloreaction and graft rejection, but it is associated with an increased risk of infection and malignancies. In recent years, several biomaterial-based strategies have been developed for preventing immune rejection of allogenic cell grafts, relying on cell encapsulation within a membrane capsule permeable to nutrients and waste products; however, the capsule also prevents cell entry and vascularization, thus limiting the size of the device to the oxygen diffusion distance of 200 μm.

An ideal cell transplantation device should enable vascularization of its entire volume to maintain the viability of the transplanted cells, and should promote graft integration within the host. Nevertheless, device vascularization is often associated with increased risk of allograft rejection due to massive infiltration of leukocytes via blood circulation.

Transforming growth factor-β (TGF-β) is an immunoregulatory cytokine, which can potentiate the generation of an immunotolerant microenvironment as it acts to suppress inflammatory processes, such as those evident in autoimmune diseases and cancer. In a TGF-β-rich environment, dendritic cells (DCs), which uptake antigens, become tolerogenic and mediate the differentiation of CD4+ T cells into anti-inflammatory regulatory T cells, which suppress not only the generation of effector CD4+ T cells but also the activation and proliferation of cytotoxic CD8+ T cells.

Thus, there exists a need for improved compositions and methods for generating local immunotolerant microenvironment while avoiding undesirable systemic effects.

SUMMARY OF THE INVENTION

The present invention relates, in one aspect, to a method for inducing an immunotolerant response in a subject, the method comprising administering to said subject a composition comprising a sulfated polysaccharide and a bioactive polypeptide and wherein said bioactive polypeptide non-covalently associates with a sulfate group of the sulfated polysaccharide. In one embodiment, the bioactive polypeptide is a transforming growth factor β1 (TGF-β1).

In yet a further aspect, the present invention relates to a method for reducing or preventing an allograft rejection in a subject the method comprising administering to said subject a composition comprising a sulfated polysaccharide and a bioactive polypeptide, and wherein said bioactive polypeptide non-covalently associates with a sulfate group of the sulfated polysaccharide, thereby reducing or preventing an allograft rejection in said subject. In one embodiment, the bioactive polypeptide is a transforming growth factor β1 (TGF-β1).

The present invention further relates to a method for treating an autoimmune disease or disorder in a subject, the method comprising administering to said subject a composition comprising a sulfated polysaccharide, a first bioactive polypeptide and a second bioactive polypeptide, wherein each of the first and second bioactive polypeptides non-covalently associates with a sulfate group of the sulfated polysaccharide, and said composition further comprising a supporting matrix, wherein the supporting matrix is a polymer selected from the group consisting of a polysaccharide, a protein, an extracellular matrix component, a synthetic polymer, and a mixture thereof. In one embodiment, the first bioactive polypeptide is a TGF-β1. In one embodiment, the second bioactive polypeptide is myelin oligodendrocyte glycoprotein (MOG).

BRIEF DESCRIPTION OF THE DRAWINGS

FIG. 1A shows the fabrication process of alginate-sulfate/alginate scaffolds. A mixture of 90% alginate and 10% alginate-sulfate was cross-linked by using calcium ions. The mixture was then poured onto a 96-well plate and freeze-dried to form a macroporous scaffold. TGF-β and angiogenic factors were affinity-bound to alginate-sulfate in the scaffold.

FIG. 1B shows the graph measuring the percentage of retained TGF-β when affinity-bound to alginate-sulfate/alginate scaffold vs. adsorbed to pristine scaffold. The percentage is calculated from total input TGF-β over a period of 7 days, as detected by ELISA.

FIG. 1C shows western blot plot of p-SMAD2 and p-SMAD3, using lyses of NIH-3T3 fibroblasts cell line cultures 40 min after exposure to 0.5 ng/ml TGF-β.

FIG. 1D shows a graph illustrating analysis of western blot of P-SMAD2/actin. Lanes are: 1: medium, no TGF-β; 2: medium+ TGF-β; 3: TGF-β released from scaffold over time; 4: afTGF-β after dissociation from Alg/AlgS scaffold with acidic pH; and 5: afTGF-β after dissolving alginate-sulfate/alginate scaffold with EDTA. The data represent mean value and SD of triplicates.

FIG. 2A shows timeline of the in vitro experiment: OTII splenocytes were seeded within scaffolds with or without afTGF-β (50 ng/scaffold). Two hours post seeding, OVA peptide (20 μg/ml) was added to the medium to activate the splenocytes and cytokines were measured thereafter.

FIG. 2B shows a graph measuring IL-17 (72 h) folds change in cytokine secretion as compared with -TGF-OVA control group.

FIG. 2C shows a graph measuring IL-10 (48 h) folds change in cytokine secretion as compared with -TGF-OVA control group.

FIG. 2D shows a graph measuring IL-2 (24 h) folds change in cytokine secretion as compared with -TGF-OVA control group.

FIG. 2E shows a graph measuring IFN-γ (48 h) folds change in cytokine secretion as compared with -TGF-OVA control group.

FIG. 5C shows percentage of Tregs from total CD4+ T cells with and without afTGF-β, as compared with -TGF-OVA control group.

FIG. 5D shows IL-2 folds change secretion with or without afTGF-β, as compared with -TGF-OVA control.

FIG. 5E shows IFN-γ folds change secretion with or without afTGF-β, as compared with -TGF-OVA control.

FIG. 5F shows IL-17 folds change secretion with or without afTGF-β, as compared with -TGF-OVA control.

FIG. 6A shows a graph measuring percentage of Tregs from total CD4+ T cells with or without afTGF-β, as compared with a -TGF-OVA control group.

FIG. 6B shows a graph measuring IL-2 folds change secretion with or without afTGF-β, as compared with a -TGF-OVA control group.

FIG. 6C shows a graph measuring IFN-γ folds change secretion with or without afTGF-β, as compared with a -TGF-OVA control group.

FIG. 6D shows a graph measuring IL-17 folds change secretion with or without afTGF-β, as compared with a -TGF-OVA control group.

FIG. 6E shows a graph measuring IL-10 folds change secretion with or without afTGF-β, as compared with a -TGF-OVA control group.

FIG. 10A shows a FACS plot demonstrating GFP+ fibroblasts population gating in afTGF-β constructs; 15 days post transplantation.

FIG. 10B shows a graph demonstrating percentage of GFP+ fibroblasts from fibroblasts remaining 3 days post transplantation.

FIG. 10C shows a FACS plot measuring annexinV and PI stained GFP+ cells that remained inside the constructs.

FIG. 11A shows a graph measuring fold change in secretion of IL-17 (72 hours) by splenocytes isolated from mice 15 and 30 days post transplantation, cultured and activated using allofibroblast lysates as compared with a wild type (WT) mice control group.

FIG. 11B shows a graph measuring fold change in secretion of IL-2 (24 hours) by splenocytes isolated from mice 15 and 30 days post transplantation, cultured and activated using allofibroblast lysates as compared with a wild type (WT) mice control group.

FIG. 11C shows a graph measuring fold change in secretion of IFN-γ (48 hours) by splenocytes isolated from mice 15 and 30 days post transplantation, cultured and activated using allofibroblast lysates as compared with a wild type (WT) mice control group.

FIG. 11D shows a graph measuring fold change in secretion of IL-10 (48 hours) by splenocytes isolated from mice 15 and 30 days post transplantation, cultured and activated using allofibroblast lysates as compared with a wild type (WT) mice control group.

µg/ml) in 2D petri dishes and, as compared with control group without TGF-β and without OVA, indicating an immunoregulatory effect of TGF-β. The change in IL-10 secretion (d) was not different between cultures with or without TGF-β, and is according with the lack of difference in CD4+CD25+Foxp3+ Treg population.

Figures 16A, 16B:
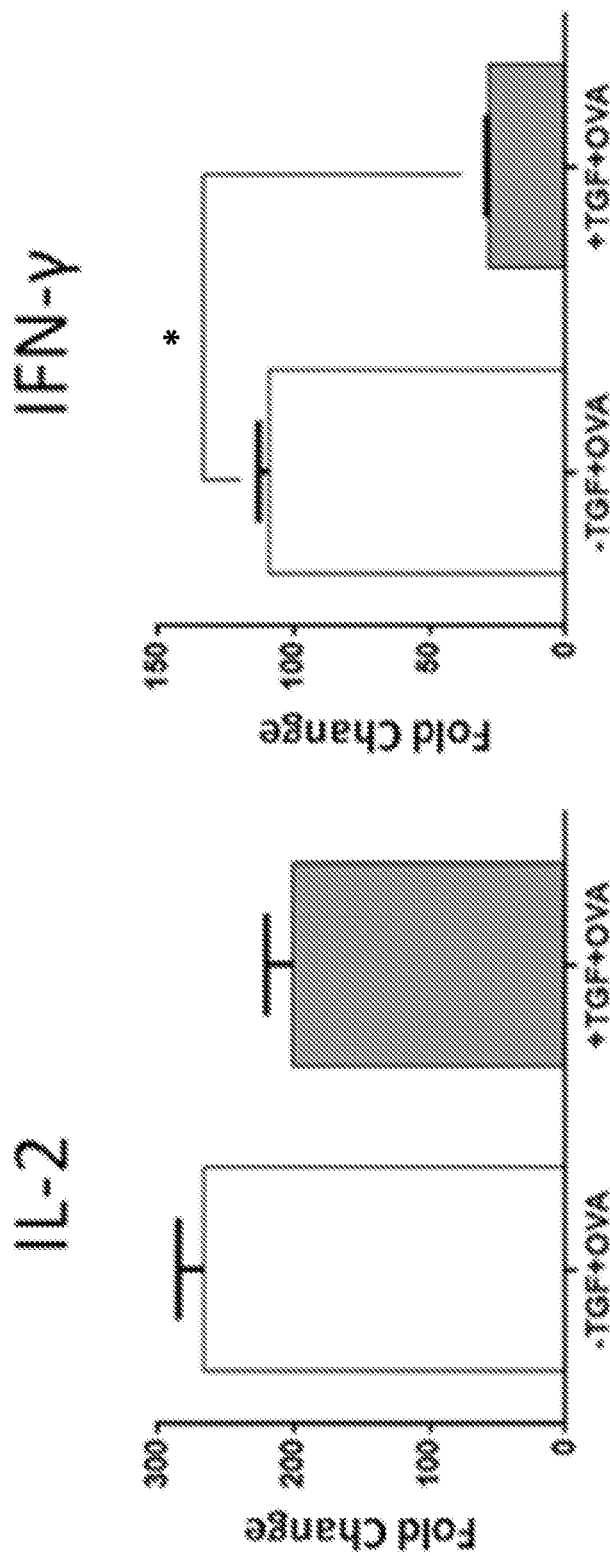
FIG. 16A shows fold change in IL-2 secretion by whole splenocytes isolated from OTII mice, cultured in the presence of soluble TGF-3 was added to the culture at a final concentration of 100 ng/ml (corresponding to an afTGF-β concentration of 50 ng/scaffold in 0.5 ml medium), and activated with the OVA peptide (final concentration: 20 μg/ml) in 2D petri dishes and, as compared with control group without TGF-β and without OVA, indicating that splenocytes were activated as a result of the OVA peptide.
FIG. 16B shows fold change in IFN-γ secretion by whole splenocytes isolated from OTII mice, cultured in the presence of soluble TGF-β was added to the culture at a final concentration of 100 ng/ml (corresponding to an afTGF-β concentration of 50 ng/scaffold in 0.5 ml medium), and activated with the OVA peptide (final concentration: 20 μg/ml) in 2D petri dishes and, as compared with control group without TGF-β and without OVA, indicating an immunoregulatory effect of TGF-β. The change in IL-10 secretion (d) was not different between cultures with or without TGF-β, and is according with the lack of difference in CD4+CD25+Foxp3+ Treg population.
Figure 16D:
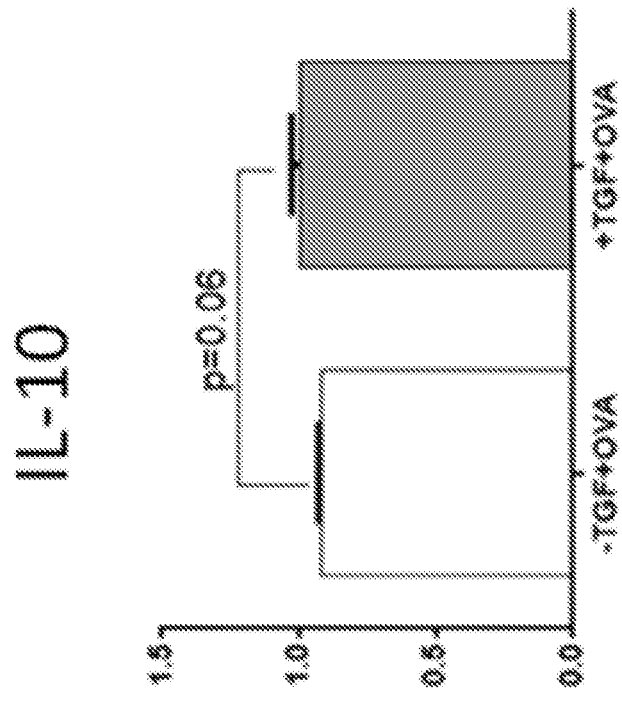
FIG. 16D shows fold change in IL-10 secretion by whole splenocytes isolated from OTII mice, cultured in the presence of soluble TGF-β was added to the culture at a final concentration of 100 ng/ml (corresponding to an afTGF-β concentration of 50 ng/scaffold in 0.5 ml medium), and activated with the OVA peptide (final concentration: 20
Figure 16C:
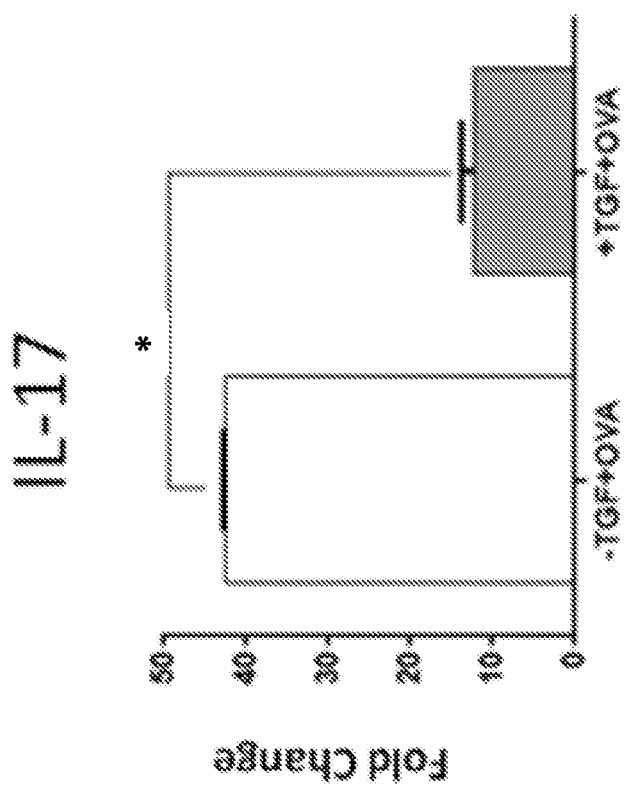
FIG. 16C shows fold change in IL-17 secretion by whole splenocytes isolated from OTII mice, cultured in the presence of soluble TGF-β was added to the culture at a final concentration of 100 ng/ml (corresponding to an afTGF-β concentration of 50 ng/scaffold in 0.5 ml medium), and activated with the OVA peptide (final concentration: 20 μg/ml) in 2D petri dishes and, as compared with control group without TGF-β and without OVA, indicating an immunoregulatory effect of TGF-β. The change in IL-10 secretion (d) was not different between cultures with or without TGF-β, and is according with the lack of difference in CD4+CD25+Foxp3+ Treg population.
Figure 16E:
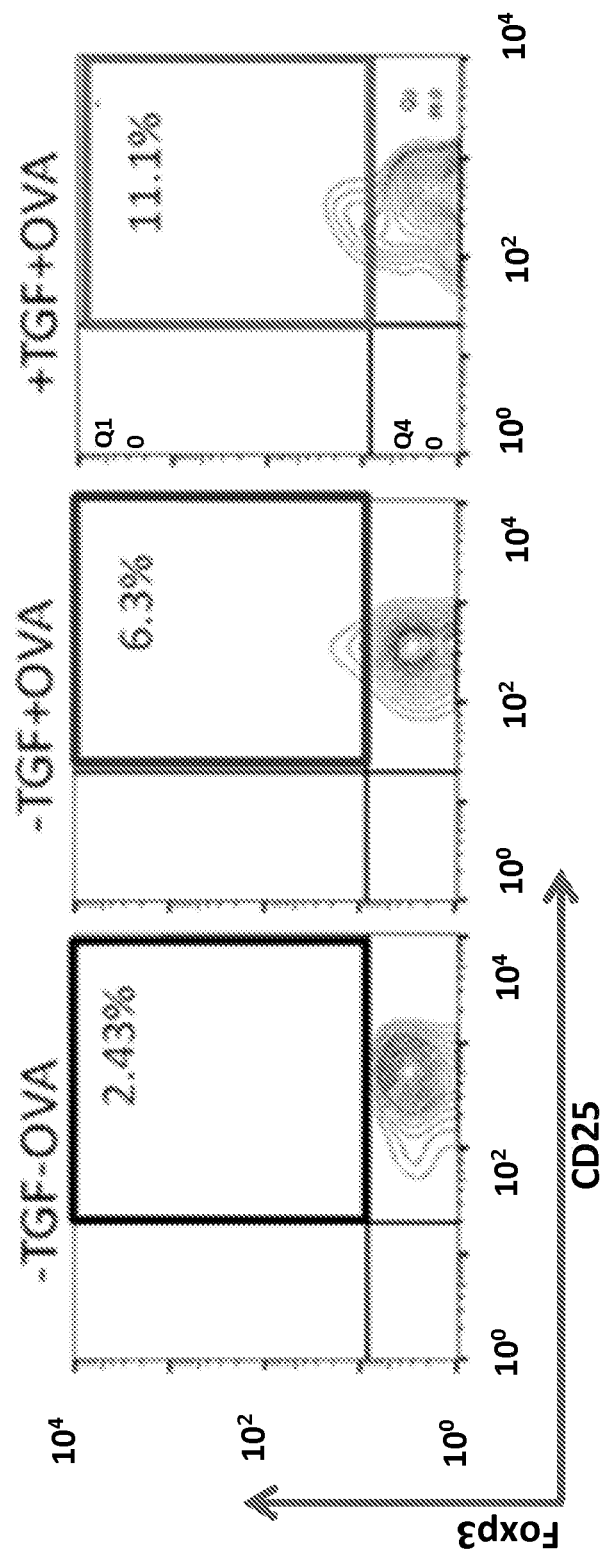

FIG. 16E shows a representative FACS plots of CD25 and Foxp3 expression of CD4+ T cells, 3 days after seeding in 2D cultures.

Figure 17B:
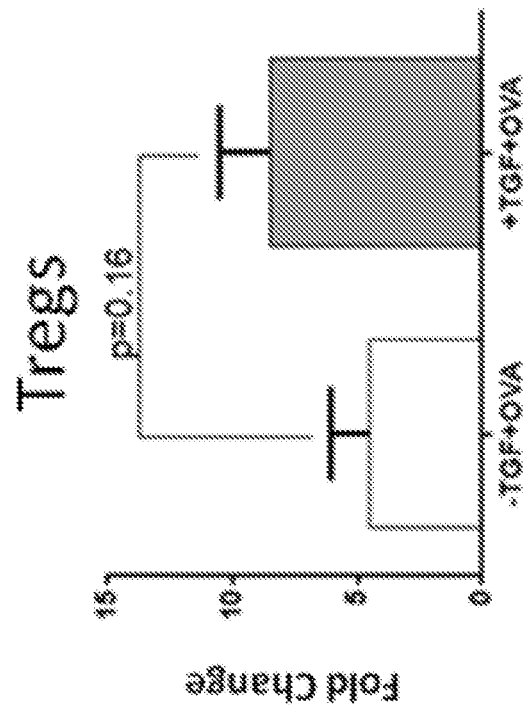
Figure 17A:
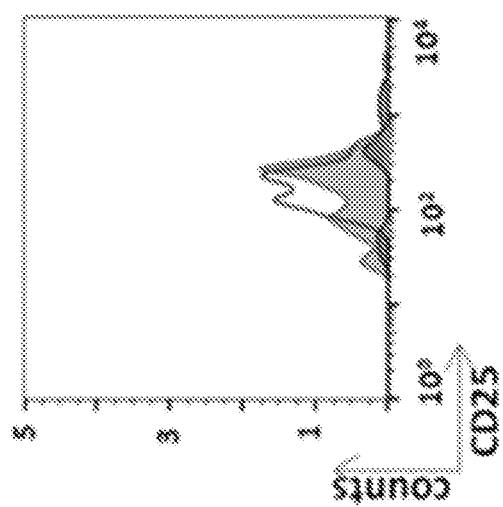

FIG. 17A shows a representative representative FACS histogram, indicating that Tregs do not increase in the presence of soluble TGF-β. Red: TGF-β, blue: TGF-β-free, black: control group (Tregs not detected).

FIG. 17B shows a graph measuring change in the percentage of CD4+CD25+Foxp3+ of the total CD4+ T cells, with or without afTGF-β, as compared with the control group without TGF-β and without OVA. The bars represent the mean values of triplicates and the SEMs of 3 separate experiments, and are compared with an unpaired t-test. *p<0.05.

Figure 17D:
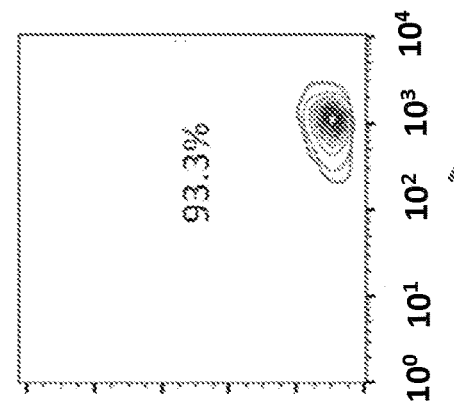
Figure 17C:
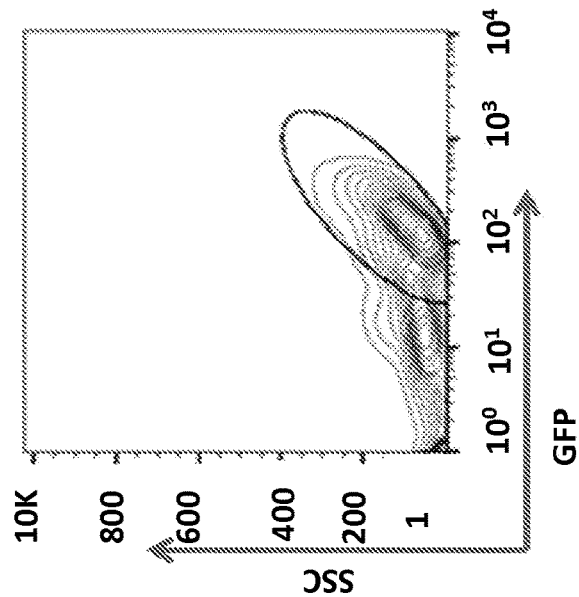

FIG. 17C shows a FACS plot of GFP+ cells isolated from a scaffold with affinity bound VEGF and with PDGF-ββ (each at 200 ng/scaffold) and with or without afTGF-β (100 ng/scaffold), and initially seeded with GFP+ allofibroblasts ($0.5 \times 10^6$ cells/scaffold). The construct was transplanted under the kidney capsule of mice, and was retrieved 3 days post transplantation.

FIG. 17D shows a graph demonstrating that three days post transplantation, there was no significant difference was found (p>0.05) between afTGF-β constructs and TGF-β-lacking constructs in the percentage of GFP+ cells of the total seeded cells. n=5, results were compared with an unpaired t-test.

Figure 17E:
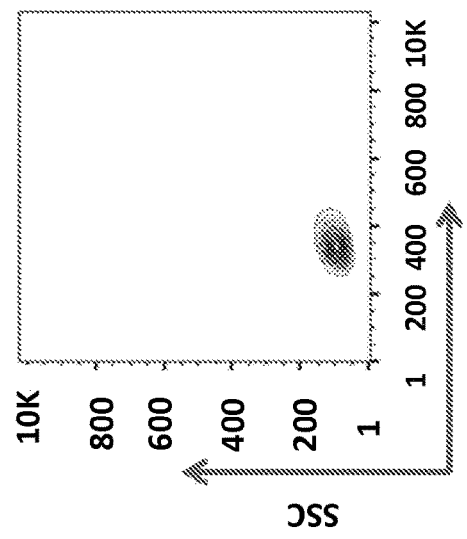

FIG. 17E shows a FACS plot of CD8+ cells that were magnetically separated from splenocytes of hosts transplanted with afTGF-β constructs or with TGF-β-lacking constructs, and were co-cultured with allofibroblasts for a CD8+ cytotoxicity assay. Magnetic separation resulted in above 93% purity of cells expressing CD8.

Figure 18:
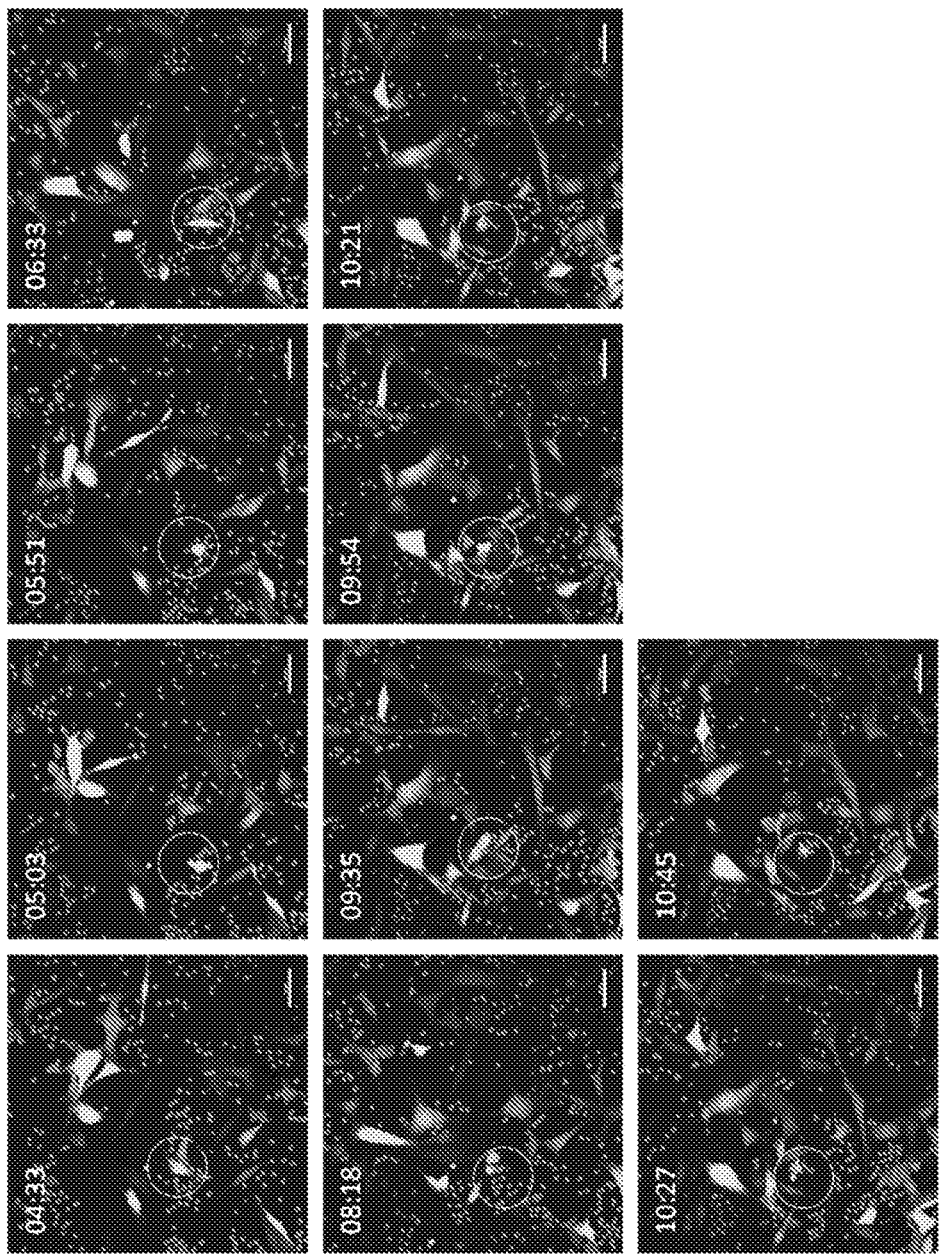

FIG. 18 shows live imaging of CD8+ cytotoxicity assay conducted by co-culturing fibroblasts and CD8+ T cells isolated from spleens of host mice transplanted with afTGF-β constructs or with TGF-β-lacking constructs, at a ratio of 1:4 between fibroblasts and CD8+ T cells respectively. The control group was CD8+ T cells isolated from wild type mice that did not undergo transplantation.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The present invention relates, in one aspect, to a method for generating an immunotolerant response in a subject, the method comprising administering to said subject a composition comprising a sulfated polysaccharide and a bioactive polypeptide and wherein said bioactive polypeptide non-covalently associates with a sulfate group of the sulfated polysaccharide. In one embodiment, the bioactive polypeptide is a transforming growth factor β1 (TGF-β1).

The present invention relates, in one aspect, to a method of generating an immunotolerant response in a subject comprising administering to said subject a composition comprising a sulfated polysaccharide and a transforming growth factor β1 (TGF-β1). Administering such a composition to a mammal, in one embodiment, a human, is useful for localized release of TGF-β1, thereby achieving a highly localized suppression of immune response, including autoimmune response. In another aspect, the immunosuppression is achieved through several TGF-β1-mediated effects, including inhibition of dendritic cell (DCs) maturation, increase the frequency of Tregs, reduction the effector functions of CD4 and CD8 cytotoxic T cells in an IL-10-dependent manner, and reduction in levels of pro-inflammatory cytokines. In an additional aspect, the local immunoregulatory effects of afTGF-β are projected to the spleen, resulting in significantly reduced effector functions of allofibroblast-specific CD4 and CD8 T cells. In a further aspect, the administered composition comprises additional bioactive polypeptides that may exert further highly localized effects. This approach has the advantage of avoiding large scale side effects that may result from systemic administration through traditional routes.

In yet a further aspect, the present invention relates to a method for improving the success of an allograft in a subject the method comprising administering to said subject a composition comprising a sulfated polysaccharide and a bioactive polypeptide, and wherein said bioactive polypeptide non-covalently associates with a sulfate group of the sulfated polysaccharide, thereby improving the success of said allograft in said subject. In one embodiment, the bioactive polypeptide is a transforming growth factor β1 (TGF-β1).

The present invention further relates to a method of improving allograft success, or reducing or preventing an allograft rejection, through localized suppression of a host immune response to an allocell transplant. The immune response is a consequence of transplant vascularization, which is also critical for draft integration with the host. The Examples below demonstrate that localized release of TGFβ1, an immunoregulatory cytokine, creates an immunoregulatory microenvironment that locally suppresses inflammatory signaling (e.g. via IL-17A), which otherwise would ultimately lead to anti-allograft cytotoxicity.

The present invention additionally describes a method of improving allograft success or reducing or preventing an allograft rejection through suppression of allocell apoptosis and increasing allocell survival. As demonstrated below, TGFβ1-scaffolds surprisingly and unexpectedly result in both lower rate of apoptotic allocells and higher rate of allocell survival, even after a prolonged implantation.

In one embodiment, the present invention provides a method for reducing or preventing an allograft rejection in a subject, the method comprising administering to said subject a composition comprising a sulfated polysaccharide and a bioactive polypeptide, wherein the bioactive polypeptide is a transforming growth factor β1 (TGF-β1), and wherein said TGF-β1 non-covalently associates with a sulfate group of the sulfated polysaccharide.

In another embodiment, the present invention provides a method for reducing or preventing an allograft rejection in a subject, the method comprising administering to said subject a composition comprising PDGF-ββ-alginate sulfate, VEGF-alginate sulfate, and TGFβ1-alginate sulfate, said composition further comprising a supporting matrix, wherein the supporting matrix is a polymer selected from the group consisting of a polysaccharide, a protein, an extracellular matrix component, a synthetic polymer, and a mixture thereof.

In another embodiment, the present invention relates to a method of promoting integration of an allograft with the host through stimulating vascularization of an allocell transplant without a concomitant anti-allograft immune response by the host. Thus, the present invention provides for a method of stimulating angiogenesis within an allograft through localized release of angiogenic factors concurrently with TGFβ-1. For example, administration of a bioconjugate comprising a sulfated alginate and a mixture of TGFβ and angiogenic factors VEGF and PDGF-β to animals, promoted sustained release of the factors and lead to vascularization and formation of mature blood vessels.

The present invention also relates to a method of generating an immunotolerant response through suppression of dendritic cell maturation. In some embodiments, as demonstrated below, the release of TGFβ1 results in a higher fraction of dendritic cells that infiltrate the scaffold remaining immature, thereby increasing the frequency of Tregs and suppressing the activation of cytotoxic CD8 T cells.

This invention further provides a prolonged presentation of bioactive polypeptides, including but not limited to TGFβ 1. As described in more detail below, the compositions of the present invention can reversibly and specifically interact with positively-charged polypeptides and/or heparin-binding polypeptides, for example TGFβ 1. This reversible binding leads to a gradual release of said polypeptides, which can be sustained over a prolonged period of time. The present invention contemplates the sustained release of polypeptides maintained over a period of about 10 days post administration. In another embodiment, the sustained release period is about 15 days. In yet another embodiment, the sustained release period is about 30 days. In a further embodiment, the sustained release period is about 60 days. In yet further embodiment, the sustained release period is more than 60 days. In another embodiment the sustained release period ranges from about 10 days to about 15 days, or from 10 to 15 days, or from about 15 days to about 30 days, or from 15 to 30 days or from about 30 days to about 60 days, or from 30 to 60 days, or 10, 15, 30, 60 days post administration or any integer day in between. The present invention further contemplates the sustained release of polypeptides not exceeding 10 days. In another embodiment, the sustained release period does not exceed 15 days. In yet another embodiment, the sustained release period does not exceed 30 days. In a further embodiment, the sustained release period does not exceed 60 days. In a yet further embodiment, the sustained release period does not exceed 90 days. In an additional embodiment, the sustained release period does not exceed 120 days. In one embodiment, the compositions and methods of the present invention promote systemic release of polypeptides (e.g. into subject's bloodstream). In another embodiment, the compositions and methods of the present invention promote local release of polypeptides.

In one embodiment, the present invention provides a method for treating an autoimmune disease or disorder in a subject, the method comprising administering to said subject a composition comprising a sulfated polysaccharide and a bioactive polypeptide, wherein the bioactive polypeptide is a transforming growth factor β1 (TGF-β1), and wherein said TGF-β1 non-covalently associates with a sulfate group of the sulfated polysaccharide.

The present invention further relates to a method for treating an autoimmune disease or disorder in a subject, the method comprising administering to said subject a composition comprising a sulfated polysaccharide, a first bioactive polypeptide and a second bioactive polypeptide, wherein each of the first and second bioactive polypeptides non-covalently associates with a sulfate group of the sulfated polysaccharide, and said composition further comprising a supporting matrix, wherein the supporting matrix is a polymer selected from the group consisting of a polysaccharide, a protein, an extracellular matrix component, a synthetic polymer, and a mixture thereof. In one embodiment, the first bioactive polypeptide is a TGF-β1. In one embodiment, the second bioactive polypeptide is myelin oligodendrocyte glycoprotein (MOG).

The present invention further relates to a method of suppressing or treating an autoimmune disease or disorder in a subject while avoiding side effects of systemic immunosuppression. Thus, the present invention provides for the localized release of bioactive polypeptides, including, but not limited to TGFβ-1 that interfere with autoimmune signaling resulting in its localized suppression. The autoimmune diseases and disorders contemplated by the present invention include, but are not limited to multiple sclerosis, type I diabetes, and psoriasis.

In another aspect, the present invention relates to the suppression of an autoimmune disorder, wherein said autoimmune disorder is selected from a group consisting of multiple sclerosis, psoriasis, and type I diabetes.

Thus, this invention in one aspect provides a method for inducing immunotolerance in CD4+ T cells specific to Multiple sclerosis (MS) autoantigens, which include, but are not limited to, myelin basic protein (MBP), proteolipid protein (PLP) and myelin oligodendrocyte glycoprotein (MOG). In one embodiment, the present invention provides a method for inducing immune tolerogenic effects in CD4+ T cells specific to MOG, or an autogenic fragment thereof, through administering of a bioconjugate comprising a sulfated polysaccharide, TGFβ1, and MOG, or an autoimmunogenic fragment thereof. Several autoimmunogenic MOG fragments are known in the art, and include peptides corresponding to mouse MOG amino acids 1-22, 35-55, and 64-96 (see e.g. US Pat. Pub 2009/0053249, hereby incorporated by reference in its entirety). In one embodiment, the MOG autoimmunogenic fragment is the peptide MEVGWYRSPFSRV-VHLYRNGK (mouse MOG35-55; SEQ ID NO: 1).

In an additional aspect, the present invention provides a method for preventing autoimmune destruction of pancreatic β cells (which, in one embodiment, underlies type I diabetes) through inducing immunotolerance in CD4+ T cells specific to pancreatic β cells. In one embodiment, the present invention provides a method for inducing immune tolerogenic effects in CD4+ T cells specific to pancreatic β cells, through administering of a bioconjugate comprising a sulfated polysaccharide, TGFβ1, and allogeneic or syngeneic β cells.

In yet an additional aspect, the present invention provides a method for suppressing autoimmune inflammatory signaling related to abnormal keratinocyte growth (which underlies psoriasis) through inducing immunotolerance in dermal CD4+ T cells. In one embodiment, the present invention provides a method for inducing immune tolerogenic effects in dermal CD4+ T cells through intradermal administering of a bioconjugate comprising a sulfated polysaccharide, TGFβ1, and cellular or molecular preparations representing the tissue, such as materials obtained from skin biopsy.

The term "bioactive polypeptide" as used herein refers to a polypeptide exhibiting a variety of pharmacological activities in vivo and include, without being limited to, growth factors, cytokines, chemokines, angiogenic factors, immunomodulators, hormones, and the like. In the present application, the terms "polypeptide" and "proteins" are used interchangeably. The at least one bioactive polypeptide may be a positively charged polypeptide and/or a heparin-binding polypeptide.

In one embodiment, the bioactive polypeptide is TGFβ. The present invention encompasses all the known isoforms of TGF (TGFβ1 to TGFβ5; TGFβ1-3 are mammalian, TGFβ4 is found in chicken; and TGFβ5 found in frog), as well as their fragments, mutants, homologs, analogs and allelic variants. In one embodiment, TGFβ is a mammalian TGFβ. In one embodiment, TGFβ is TGFβ1. In another embodiment, TGFβ is TGFβ2. In another embodiment, TGFβ is TGFβ3. In another embodiment, TGFβ is either human TGFβ1 (Genbank Accession No X02812) or mouse TGFβ1 (Genbank Accession No AJ00986).

In one embodiment, the term "positively charged polypeptide" refers to a polypeptide/protein that has a positive net charge at physiological pH of about pH=7.5. Examples of positively charged proteins include, but are not limited to, insulin, glatiramer acetate (also known as Copolymer 1 or Cop 1), antithrombin III, interferon (IFN)-γ (also known as heparin-binding protein), IGF, somatostatin, erythropoietin, luteinizing hormone-releasing hormone (LH-RH) and interleukins such as IL-2 and IL-6.

In one embodiment, the term "heparin-binding protein or polypeptide" refers to proteins that have clusters of positively-charged basic amino acids and form ion pairs with specially defined negatively-charged sulfo or carboxyl groups on the heparin chain (See Capila and Linhardt, 2002). Examples of heparin-binding proteins include, but are not limited to, thrombopoietin (TPO); proteases/esterases such as antithrombin III (AT III), serine protease inhibitor (SLP1), C1 esterase inhibitor (C1 INH) and Vaccinia virus complement control protein (VCP); growth factors such as a fibroblast growth factor (FGF, aFGF, bFGF), a FGF receptor, vascular endothelial growth factor (VEGF), insulin-like growth factor (IGF), hepatocyte growth factor (HGF), transforming growth factor β1 (TGF-β1), a platelet-derived growth factor (PDGF, PDGF-α and PDGF-β), epidermal growth factor (EGF), and bone morphogenetic proteins (BMP)—such as BMP-2, 4 and 7; chemokines such as platelet factor 4 (PF-4, now called CXC chemokine ligand 4 or CXCL4), stromal cell-derived factor-1 (SDF-I), IL-6, IL-8, RANTES (Regulated on Activation, Normal T Expressed and Secreted), monocyte chemoattractant protein-1 (MCP-I), macrophage inflammatory peptide-1 (MIP-I), lymphotactin, and fractalkine; lipid or membrane-binding proteins such as an annexin, apolipoprotein E (ApoE); pathogen proteins such as human immunodeficiency virus type-1 (HIV-I) coat proteins e.g. HIV-I gp120, cyclophilin A (CypA), Tat protein, viral coat glycoprotein gC, gB or gD of herpes simplex virus (HSV), an envelope protein of Dengue virus, circumsporozoite (CS) protein of *Plasmodium falciparum*, bacterial surface adhesion protein OpaA; and adhesion proteins such as 1- and P-selectin, heparin-binding growth-associated molecule (HB-GAM), thrombospondin type I repeat (TSR), peptide myelin oligodendrocyte glycoprotein (MOG), and amyloid P (AP).

Thus, in one embodiment, any bioactive polypeptide of the compositions and methods of the present invention, whether the first bioactive polypeptide or an additional bioactive polypeptide or a second or third bioactive polypeptide is AT III, TPO, SLP1, C1 INH, VCP, FGF, a FGF receptor, VEGF, HGF, IGF, PDGF, BMP, EGF, CXCL4, SDF-1, IL-6, IL-8, RANTES, MCP-1, MIP-1, lymphotactin, fractalkine, an annexin, ApoE, HIV-1 coat protein gp120, CypA, Tat protein, viral coat glycoprotein gC, gB or gD of herpes simplex virus HSV, an envelope protein of Dengue virus, CS protein of *Plasmodium falciparum*, bacterial surface adhesion protein OpaA, 1-selectin, P-selectin, HB-GAM, TSR, MOG, or AP, or a combination thereof.

In another embodiment, the bioactive polypeptide is PDGF-BB, PDGF-AA, bFGF, aFGF, VEGF, IL-6, TPO, SDF-1, HGF, EGF, MOG, BMP-2, BMP-4, BMP-7, IGF, or a combination thereof. In another embodiment, compositions for use in the methods of the present invention comprise TGF-beta, VEGF, and PDGF-ββ as bioactive polypeptides.

In some embodiments of the present invention, the at least one heparin-binding polypeptide is selected from PDGF-β, PDGF-α, bFGF, aFGF, VEGF, TGFβ1, IL-6, TPO, SDF-I, HGF, EGF, BMP, or IGF. In other embodiments of the invention, the at least one bioactive polypeptide is an angiogenic factor or a growth factor exhibiting angiogenic activity such as TGF-β1, VEGF, bFGF, aFGF, PDGF-β, IGF, and a combination thereof.

In one embodiment of the invention, the at least one angiogenic factor is VEGF, PDGF-β, or a combination of VEGF, PDGF-BB, and TGF-β 1.

In one embodiment, the bioactive polypeptide in the compositions and methods of the present invention is a cytokine. In one embodiment, the bioactive polypeptide is TGF-beta. In another embodiment, the bioactive polypeptide is interleukin (IL)-10. In another embodiment, the bioactive polypeptide is IL-4. In another embodiment, the bioactive polypeptide is IL-5. In another embodiment, the bioactive polypeptide is IL-13. In another embodiment, the bioactive polypeptide is a chemokine. In one embodiment, the chemokine is (C—X—C motif) ligand (CXCL) 12. In another embodiment, the chemokine is CXCL11.

In accordance with the present invention, the sulfated polysaccharides forming the bioconjugate may be composed of different recurring monosaccharide units, may be of different lengths, and may have different types of bonds linking said units. The sulfated polysaccharides may be linear as, for example, sulfated cellulose, branched as, for example, sulfated glycogen, and may vary in length; for example, it may be as small as a sulfated tetra- or tri-saccharide. The suitable sulfated polysaccharide may be a homopolysaccharide including, but not limited to, starch, glycogen, cellulose, chitosan, or chitin or a heteropolysaccharide including, but not limited to, alginic acid (alginate) salts and hyaluronic acid.

According to the present invention and in one embodiment, the sulfated polysaccharides comprise uronic acid residues such D-glucuronic, D-galacturonic, D-mannuronic, L-iduronic, and L-guluronic acids. Examples of polysaccharides comprising uronic acid residues include, but are not limited to, alginic acid salts, in one embodiment, sodium alginate, pectin, gums and mucilages from plant sources; and glycosaminoglycans (GAGs) from animal sources including hyaluronic acid (hyaluronan). The sulfated polysaccharides comprising uronic acid can be chemically sulfated or may be naturally sulfated polysaccharides.

In one embodiment, the sulfated polysaccharide is alginate sulfate. In another embodiment, the sulfated polysaccharide is hyaluronan sulfate.

Alginic acid is a linear polysaccharide obtained from brown algae and seaweed and consist of β-1,4-linked glucuronic and mannuronic acid units. As used herein, the term "alginate" refers to a polyanionic polysaccharide copolymer derived from sea algae (e.g., *Laminaria hyperborea, L. digitata, Eclonia maxima, Macrocystis pyrifera, Lessonia nigrescens, Ascophyllum codosum, L. japonica, Durvillaea antarctica,* and *D. potatorum*) and which includes β-D-mannuronic (M) and α-L-guluronic acid (G) residues in varying proportions.

An alginate suitable for use in the present invention has a ratio between α-L-guluronic acid and β-D-mannuronic in one embodiment, ranging between 1:1 to 3:1, in one embodiment, between 1.5:1 and 2.5:1, in one embodiment, about 2, and has a molecular weight ranging in one embodiment, between 1 to 300 kDa, in one embodiment, between 5 to 200 kDa in one embodiment, between 10 to 100 kDa, in one embodiment, between 20 to 50 kDa.

Alginate undergoes gelation in the presence of bivalent cations, such as $Ca^{2+}$ and $Ba^{2+}$. In the pharmaceutical/medicinal fields, it is used successfully as encapsulation material, mostly for cells (bacterial, plant and mammalian cells). For molecules, it is much less effective, and even macromolecules in size of 250 kDa are rapidly released from alginate hydrogel systems. In particular, biological molecules of interest such as cytokines, growth factors, with sizes ranging between 5 to 100 kDa, are rapidly released.

Hyaluronic acid is composed of repeating dimeric units of glucuronic acid and N-acetyl glucosamine and forms the core complex proteoglycans aggregates found in the extracellular matrix.

It has been previously shown that sulfating the polysaccharides, endows them with properties which allow binding and controlled release of important signal proteins such as various cytokines and growth factors. Alginate sulfate and hyaluronan sulfate were both found to mimic the biological specificities of heparan sulfate and heparin when forming the bioconjugates (see e.g. WO 2007/043050, which is hereby incorporated by reference in its entirety).

As a skilled artisan would understand, the binding between the bioactive polypeptide and the sulfated polysaccharide is selected from reversible non-covalent binding involving ionic bonds, electrostatic interactions, hydrophobic interactions, hydrogen bonds or van der Waals forces.

It should be understood that by having a positive charge, the bioactive polypeptides may be reversibly and un-covalently bound to the sulfated polysaccharides, which carry a negative charge due to their sulfur group.

Thus the present invention also provides a method for sustained localized release of at least one bioactive polypeptide.

According to the methods of the present invention, a bioconjugate can be injected or implanted to any part of the human body and serve as a delivery system for said bioactive polypeptide(s). In one embodiment, the bioconjugate of the present invention may be in the form of flowable gel. In another embodiment, a bioconjugate may be preformulated as a rigid implantable scaffold. In an additional embodiment, the implantable scaffold may further contain a supporting matrix.

The matrix may serve as support or as a carrier for the bioconjugate and may be made up of particles or porous materials. The matrix material may be flexible and amenable to be fixed in place preventing its migration to an unintended location. The polymer matrix materials can be either natural or synthetic and include, but are not limited to, synthetic polymers such as polyethylene glycol (polyethylene oxide), polyvinyl alcohol), polylactic acid, polyglycolic acid, and polyhydroxybutyrate, or natural polymers like collagen, fibrin, and gelatin, or polysaccharides like chitosan and alginate.

The matrix may be in any form appropriate to the mode of delivery, for example, hydrogel, beads, microspheres (microbeads), hydrogel microcapsules, sponges, scaffolds, foams, colloidal dispersions, nanoparticles, suspensions, and the like. Thus, a sustained release dosage form based on bioconjugates of sulfated polysaccharides and bioactive peptides may be fashioned as liquids, meshes, sponges, fibers and hydrogels.

The term "hydrogel" as used herein refers to a network of natural or synthetic hydrophilic polymer chains able to contain water. Examples of compounds able to form such networks are alginate, a partially calcium cross-linked alginate solution, chitosan and viscous hyaluronan.

The term "bioconjugate" as used herein refers to a sulfated polysaccharide bound covalently or non-covalently to a bioactive polypeptide. Examples of non-covalent binding are binding involving ionic bonds, electrostatic interactions, hydrophobic interactions, hydrogen bonds or van der Waals forces.

The term "scaffold" as used herein refers to any synthetic or organic structure comprising a void. Non-limiting examples of such scaffolds are molds, casts and voids in damaged tissue in a mammal.

The composition of the present invention can be administered by any suitable method, for example but is not limited to, intraliver, intradermal, transdermal (e.g. in slow release formulations), intramuscular, intraperitoneal, intravenous, intracoronary, subcutaneous, oral, epidural, topical, and intranasal routes. Administration also includes surgically administering, implanting, inserting, or injecting the implant (or sections thereof) into a subject. The implant (or section) can be located subcutaneously, intramuscularly, or located at another body location which allow the implant to perform its intended function. Generally, implants (or sections) are administered by subcutaneous implantation at sites including, but not limited to, the upper arm, back, or abdomen of a subject. Other suitable sites for administration may be readily determined by a medical professional. Multiple implants or sections may be administered to achieve a desired dosage for treatment. Any other therapeutically efficacious route of administration can be used. Administration also encompasses either systemic administration or local administration of compositions as described herein to a subject.

The term "subject" includes but is not limited to a human. In another embodiment, the subject is murine, which in one embodiment, is a mouse, and, in another embodiment, is a rat. In another embodiment, the subject is canine, feline, bovine, ovine, or porcine. In another embodiment, the subject is mammalian.

The methods of manufacturing sulfated polysaccharide bioconjugates are well known (see e.g. US Pat. Pub. 2015/0051148, hereby incorporated by reference in its entirety), and further described hereinbelow.

The present invention contemplates a mixture of sulfated and unsulfated polysaccharides, for example alginate and alginate sulfate. According to the present invention the proportion of sulfated polysaccharide may range from about 1% to about 40% of the total polysaccharide by weight, in one embodiment, from about 3% to about 30% of the total polysaccharide by weight, in one embodiment, from about 4% to about 20% of the total polysaccharide by weight, in one embodiment, from about 5% to about 10% of the total polysaccharide by weight. Alternatively the aforementioned proportions represent percentage by mass. In an alternative embodiment, the binding and release from these bioconjugates can be controlled by the degree of polysaccharide sulfation and by the extent of sulfated polysaccharide sulfate incorporation into the delivery system.

The present invention further contemplates adding a pharmaceutically acceptable carrier to the sulfated polysaccharide-bioactive polypeptide bioconjugate. The term "pharmaceutically acceptable carrier" refers to a vehicle which delivers the active components to the intended target and which will not cause harm to humans or other recipient organisms. As used herein, "pharmaceutical" will be understood to encompass both human and veterinary pharmaceuticals. Useful carriers include, for example, water, acetone, ethanol, ethylene glycol, propylene glycol, butane-1, 3-diol, isopropyl myristate, isopropyl palmitate, mineral oil and polymers composed of chemical substances like polyglycolic acid or polyhydroxybutyrate or natural polymers like collagen, fibrin or polysaccharides like chitosan and alginate. The carrier may be in any form appropriate to the mode of delivery, for example, solutions, colloidal dispersions, emulsions (oil-in-water or water-in-oil), suspensions, creams, lotions, gels, foams, mousses, sprays and the like. Methodology and components for formulation of pharmaceutical compositions are well known and can be found, for example, in Remington's *Pharmaceutical Sciences, Eighteenth Edition*, A. R. Gennaro, Ed., Mack Publishing Co. Easton Pa., 1990. In one embodiment of the invention, the carrier is an aqueous buffer. In another embodiment, the carrier is a polysaccharide and is in one embodiment, alginate hydrogel or in another embodiment, hyaluronic acid.

Examples of immunotolerant responses include, but are not limited to, allograft success, lack of allograft rejection, suppression of autoimmune disorder, suppression of an immune response to an allocell transplantation, suppression of allocell apoptosis, an increase in allocell survival, stimulation of vascularization of allocell transplant, prolonged presentation of said bioactive polypeptide, suppression of inflammatory signaling, suppression of dendritic cell maturation, suppression of CD8+ T cells cytotoxicity response, and stimulation of regulatory T cells differentiation.

Examples of a disease or disorder treated by the compositions of the present invention include, but are not limited to, allograft rejection, multiple sclerosis, psoriasis, type I diabetes, rheumatoid arthritis, systemic lupus erythematosus, myasthenia gravis, Hashimoto thyroiditis, primary biliary cirrhosis, active chronic hepatitis, adrenalitis/Addison's disease, polymyositis, dermatomyositis, autoimmune haemolytic anaemia, myocarditis, myopericarditis, scleroderma, uveitis (including phacouveitis and sympathetic ophthalmia) pemphigus vulgaris, pemphigoid, pernicious anaemia, autoimmune atrophic gastritis, Crohn's disease, and colitis ulcerosa.

All patents, patent applications, and scientific publications cited herein are hereby incorporated by reference in their entirety.

The invention will now be described with reference to some non-limiting examples.

EXAMPLES

Materials and Methods
Chemicals

Sodium alginate (>65% guluronic acid monomer content; VLVG of M.W. 30 kDa and LVG of 100 kDa) was purchased from NovaMatrix, FMC BioPolymer (Drammen, Norway). Cell culture medium was composed of Iscove's Modeified Dulbecoo's Medium (IMDM) (Bone marrow derived dendritic cells (bmDC) medium) or Dulbecoo's Modified Eagle Medium (DMEM) (clone medium), purchased from Gibco (CA, USA), supplemented with 10% Fetal Bovine Serum (FBS, HyClone™), 2 mm L-glutamine, 100 U/mL penicillin, 1 µg/mL streptomycin (Pen/Strep), 2.5 U/mL Nystatin (all from Biological Industries, Kibbutz Beth HaEmek, Israel) and 50 µm β-mercaptoethanol (Sigma-Aldrich, Rehovot, Israel). Hank's balanced salt solution (HBSS) and phosphate buffer saline (PBS) were also purchased from Biological Industries. Ammonium-Chloride-Potassium (ACK) lysis buffer was purchased from BioWhittaker (Walkersville, Md., USA). Isoflurane was purchased from Minrad (NY, USA). CD4+ and CD8+ T-cell purification kits were purchased from STEMCELL™ Technologies (Vancouver, Canada). All antibodies used for ELISA, FACS, Western blotting, and IHC were purchased from BioLegend (CA, USA) unless stated otherwise. Vascular Endothelial Growth Factor (VEGF), Platelet-Derived Growth Factor (PDGF-ββ), and Transforming growth factor β1 (TGF-β) were purchased from PeproTech (NJ, USA). Phosphatase inhibitors and nitrocellulose membrane used in western blotting were purchased from Santa Cruz Biotech (TX, USA). The Tissue-Tek O.C.T. compound was purchased from Sakura (CA, USA). All other chemicals, unless specified otherwise, were purchased from Sigma-Aldrich. Ovalbumin (OVA) peptide was purchased from GenScript (NJ, USA).

Animals and Cells Lines

C57/Bl6 mice and CD11cdnR transgenic mice were purchased from Jackson Laboratory (Maine, USA). OVA-specific, MHC class II-restricted alpha beta T cell receptor (OTII) transgenic mice were a generous gift from Dr. Eli Lewis, at Ben-Gurion University of the Negev, Israel. All mice were housed and bred at the animal facility of the Ben-Gurion University Medical Center (Beer-Sheva, Israel) and were maintained in autoclaved cages with autoclaved bedding, food, and water.

NIH/3T3 fibroblasts cell line (ATCC® CRL1658™) was a generous gift from Dr. Eli Lewis at Ben-Gurion University of the Negev.

Preparation of Alginate Matrix

Alginate with covalently-bound adhesion peptide G4RGDY and heparin-binding peptide G4SPPRRARVTY (RGD/HBP) was synthesized as previously described, and alginate-sulfate was synthesized according to Freeman et al. 2009 (*Biomaterials*. 2009; 30(2122-31)) and Freeman et al. 2008 (*Biomaterials*. 2008; 29(3260-8)). The macroporous scaffolds were fabricated by a freeze-dry technique. Briefly, a 1.2% (w/v) sodium alginate solution was cross-linked with a 1.32% (w/v) D-gluconic acid/hemicalcium salt by homogenizing the solution to obtain a homogenous calcium ions distribution. Final component concentrations in the cross-linked solutions were 1.0% and 0.22% (w/v) for the alginate and for the cross-linker, respectively. Fifty microliters of the cross-linked alginate solution were poured into each well of 96-well plates, cooled to 4° C., frozen at (−20)° C. for 24 h, and lyophilized for 48 h at 0.08 bar and (−57)° C. Sterilization of the scaffolds was achieved by exposure to ultraviolet (UV) light in a biological hood for 1 h.

In Vitro Release Study and Evaluation of TGF-β Bioactivity

The release study of afTGF-β was tested in two groups of scaffold: a pristine alginate scaffold, and an alginate/alginate-sulfate (Alg/AlgS) scaffold (namely, 90% pristine alginate with 10% alginate sulfate). Scaffolds loaded with TGF-β were incubated in 500 µL medium (high-glucose DMEM supplemented with 100 U/mL penicillin, 0.1 mg/mL streptomycin, 0.1 mg/mL neomycin, and 0.1% bovine serum albumin (BSA) (w/v)) in 48-well plates on a rotational shaker, at 37° C., for 7 d, under sterile conditions. Medium samples were collected at 0, 1, 3, and 7 days after scaffolds were loaded with TGF-β and analyzed for released TGF-β with an anti-human recombinant TGF-β ELISA kit, according to the manufacturer's instructions. For the quantification of retained afTGF-β at the time points specified above, scaffold samples were taken and the scaffolds were dissolved in Ethylenediamine tetraacetic acid (EDTA). The solution was brought to pH=3 to dissociate the afTGF-β from the alginate chains, and was centrifuged to achieve phase separation. Prior to ELISA, the pH of the solutions was brought back to pH=7. The percentage of afTGF-β was calculated at each time point as (amount of TGF-β/initial input TGF-β amount)×100.

Isolation and Cultivation of Total Splenocytes

Animals were sacrificed and their spleen was removed, homogenized, and filtered through a 70 μm mesh to achieve a single-cell suspension. The erythrocytes were lysed with 300 μl ACK buffer and remaining cells were counted. Cells were cultured in a Clone medium (DMEM supplemented with 10% fetal calf serum, 10 mM HEPES, 1 mM sodium pyruvate, 10 mM nonessential amino acids, 1% Pen/Strep, and 50 μM β-mercaptoethanol).

Magnetic Separation of CD4+ and CD8+ T Cells

After receiving a single-cell suspension of whole splenocytes, CD4+ T cells or CD8+ T cells were separated by a magnetic bead negative selection kit, using EasySep™ Magnet (STEMCELL Technologies, Vancouver, Canada), according to manufacturer's instructions. The purified T cells were stained for CD4 or CD8, as described later for flow cytometry, and analyzed by flow cytometry to evaluate purification.

Purification and Cultivation of Bone Marrow-Derived Dendritic Cells

Dendritic cells (DCs) were generated by cultivating bone marrow-derived precursors with Granulocyte-macrophage colony-stimulating factor (GM-CSF), according to a method adapted from previous studies with several modifications. On day 0, femurs and tibiae of 4-12 week old C57/Bl6 mice were removed and purified from the surrounding tissue with gauze pads. Thereafter, the bones were placed in cold PBS, their tips were removed with scissors, and the bone marrow was flushed with cold PBS by using a 27 G needle. The resulting suspension was filtered through a 70 μm mesh and the erythrocytes were lysed for 1 min with 100 μl ACK buffer. The cell suspension was washed twice with HBSS, centrifuged at 150 g at 6° C. for 6 min, and re-suspended in DC medium [IMDM supplemented with 10% FBS, 2 mM L-Glutamine, penicillin (100 U/ml), streptomycin (1 μg/ml), nystatin (2.5 U/ml), 50 μM β-mercapthoethanol, and 20% GM-CSF supernatant from J554 cells (as detailed below)]. The cells were seeded on bacteriological 90 mm petri dishes at $5 \times 10^6$ cells/dish in 10 ml medium, and incubated for eight days. The cells were cultivated in a humidified chamber at 37° C. with 5% $CO_2$. The DC medium and the GM-CSF were replaced on day 3 and on day 5, and were ready for further experimentations on day 8.

Generation of Supernatant Containing GM-CSF

J558 cells transfected with murine a GM-CSF construct were a gift from Prof. Angel Porgador (Ben-Gurion University of the Negev, Israel). Transfected cells were selected by cultivation in the presence of 1 mg/ml G-418 for two weeks, and were seeded at a density of $\sim 2 \times 10^5$ cells/ml in tissue culture flasks. The cells were then diluted 1:5 in culture media every 2-3 days for 3 weeks. The supernatant was filtered with a 0.2 μm filter and stored at $(-80)°$ C.

Seeding and Activation of Cells within the Matrix: In Vitro Cultures

Cells were seeded ($0.5 \times 10^6$ total cells/matrix) by dropping 14 μL of cell suspension, with or without TGF-β, onto the dry alginate/alginate-sulfate matrix. The cell constructs were then centrifuged for 30 s at 500 rpm and incubated for 10 min at 37° C. and 5% $CO_2$ to allow for cell distribution within the matrix. Then, an additional 200 μL of the culture medium was added gradually and the cell device was incubated for 2 h.

For cell activation, the cell constructs were transferred to 48-well plates and supplemented with 1 ml culture media, with or without OVA peptide (final peptide concentration: 20 mg/ml). Cultivation took place within a humidified incubator, at 37° C. with 5% $CO_2$.

IL-10 Inhibition

Purified anti-mouse IL-10 (Biolegend; Cat 505012) was added as an IL-10 inhibitor at a final concentration of 1 ng/ml (an order of magnitude higher than the maximal concentration of IL-10 in the cultures). Sandwich ELISA showed no traces of IL-10 in the culture.

Retroviral Infection of NIH 3T3 Fibroblasts

PLAT-E cells were maintained in DMEM containing 10% FBS and 0.5% penicillin, streptomycin, blasticidin, and puromycin. PLAT-E packaging cells were plated at $8 \times 10^6$ cells per 100 mm dish and incubated overnight. On the next day, the cells were transfected with a pMX-IRES-GFP vector with a PolyJet in vitro transfection reagent (SignaGen, MD, USA). Twenty-four hours after transfection, the medium was replaced with a new medium and was collected 24 h and 48 h after transfection.

The 3T3/NIH fibroblasts were seeded 1 day before transduction, at $10^5$ cells per 12-well plate. The virus-containing supernatant (collected after 24 h) was supplemented with 2 μg/ml protamine sulfate, transferred to the fibroblast dish, and incubated overnight. Twenty-four hours after transfection, the virus-containing medium was replaced with the 48 h supernatant. The fibroblasts underwent three cycles of transfection.

Seeding the NIH/3T3 Fibroblasts within the Matrix: In Vivo

NIH/3T3 fibroblasts infected to express GFP (as described above) were seeded ($0.5 \times 10^6$ total cells/matrix) by dropping 30 μL of cell suspension (namely, cells in DMEM supplemented with 200 ng TGF-β or without TGF-β) onto the dry covalently-bound RGD/HBP alginate/alginate-sulfate matrix. We found that 30 μL of cell suspension is the appropriate volume to wet the entire scaffold without leaving access liquid, thus ensuring maximum binding of all of the growth factors to the scaffold. Matrices were incubated for 5 min at 37° C. and 5% $CO_2$ to allow cell distribution within the scaffold before transplanting the construct.

Device Transplantation

Immediately after seeding the cells within the matrix, the cell transplantation devices were transplanted under the left kidney capsule of C57/Bl6 wild type mice, which were anesthetized with an isoflurane-based anesthesia machine. At different days (10, 15, or 30) post transplantation, the cell transplantation devices were surgically removed with the surrounding fibrosis. Their vascularization was analyzed by immunohistochemistry and the penetrating lymphocytes populations and fibroblasts survival were analyzed with flow cytometry. At days 15 and 30 post transplantation, the spleens were also removed for a whole-lymphocytes culture and for a CD8+ cytotoxicity assay.

Fibroblasts Lysates

NIH/3T3 fibroblasts ($10^7$ cells) underwent five cycles of freezing and thawing, centrifuged, and their total protein concentration was determined with the Bio-Rad protein assay (Bio-Rad, Israel).

Activation of Total Splenocytes with Fibroblasts Lysates

Fifteen and 30 days post transplantation, total splenocytes were cultured in 96-well U plates ($2\times10^4$ cells per well), and were activated with fibroblasts lysates (final protein concentration: 10 mg/ml).

CD8+ Cytotoxicity Assay

CD8+ T cells were magnetically separated from whole splenocytes 15 and 30 days post transplantation, as described above. CD8+ T cells and NIH 3T3 fibroblasts were co-cultured at a ratio of 4:1. Two hours and 12 h post co-culturing, the cytotoxicity of the CD8+ T cells and the viability of the fibroblasts were analyzed with FACS.

Western Blotting

The NIH/3T3 fibroblasts were treated with 5 ng/ml TGF-β for 40 min and cell lysates were obtained by using Radioimmunoprecipitation assay (RIPA) buffer [150 mM NaCl, 1 mM EGTA, 50 mM Tris-HCl (pH=7.5), 1% NP-40] supplemented with a protease inhibitor cocktail and with phosphatase inhibitors. Cells were incubated with RIPA on ice for 30 minutes and then centrifuged at 13,000 rpm. The supernatants were collected, the protein concentration was determined with a Bio-Rad protein assay, and 30 μg/well of protein were used in an SDS-PAGE, and then transferred onto a nitrocellulose membrane. The membranes were blocked, for 1 h at room temperature, with 5% BSA (MP Biochemicals, Santa Ana, Ca) or with 5% milk in Tris-buffered saline supplemented with 0.5% Polysorbate 20 (TWEEN 20) (TBST), and were then incubated with the primary antibody overnight at 4° C. Proteins were detected by using the following primary antibodies: rabbit anti-phospho-SMAD2, rabbit anti-SMAD2/3 (both from Cell Signaling, Danvers, Mass.), and mouse anti-actin (MP Biochemicals, Santa Ana, Ca). Secondary horseradish peroxidase (HRP)-conjugated antibodies were goat anti-mouse IgG (Jackson labs, Sacramento, Calif.) and donkey anti-rabbit IgG (Amersham, GE healthcare, UK). A Supersignal West Pico Chemiluminescent Substrate kit (Thermo Scientific, Waltham, Mass.) was used to induce chemiluminescence, which was then detected with the ImageQuant LAS 4000 software (GE Healthcare Life Sciences, UK). Band intensity was quantified with the ImageJ software.

Flow Cytometry Analysis

For matrix analysis after in vitro studies, the matrix was first dissolved, and the cells were then obtained by centrifugation, washed with HBSS, centrifuged again, and suspended in a FACS buffer (2% FBS in PBS). For the analysis of the cell transplantation device after in vivo transplantation, the matrix and surrounding fibrosis were homogenized and filtered through a 70 μm mesh to obtain a single cell suspension, and the cells were centrifuged and re-suspended in FACS buffer (2% FBS in PBS).

After obtaining a single-cell suspension, an Fc-blocker was added for 5 min to prevent non-specific antigen binding. Thereafter, fluorescent antibodies were added according to manufacturer's instructions, and the plate was incubated on ice for 15 min. Samples were then washed with FACS buffer and centrifuged twice at 420 g for 3 min at 6° C.

For an intracellular FACS staining (Foxp3), cells were first stained with fluorescent antibodies, then incubated in a fixing buffer for 20 min, washed twice, and incubated for 15 min in a permeabilizing buffer. Thereafter, cells were washed with FACS buffer and incubated with the intracellular antibody for 30 min, centrifuged, and suspended in FACS buffer. Gallios™ Flow Cytometer (Beckman Coulter, Inc., Brea, Calif.) utilizing the FlowJo software was used for flow cytometry analysis.

All antibodies used in this study were flour-conjugated antibodies, and included APC-Cy7-conjugated anti-CD4 (Biolegend; cat 100414), PerCP-conjugated anti-CD8 (Biolegend; cat 100732), PE-conjugated anti-CD25 (Biolegend; cat 101904), PE-Cy7-conjugated anti-CD69 (Biolegend; cat 104512), APC-conjugated anti-CD107a (Biolegend; cat 121614), FITC-conjugated anti-FoxP3 (Biolegend; cat 137214), PE/Dazzle-conjugated anti-CD11c (Biolegend; cat 117348), anti-CD86 Brilliant Violet (Biolegend; cat 305431), APC-conjugated Annexin V (Biolegend; cat 640920), and PI (Biolegend; cat 421301).

Cytokine Secretion Analysis Using ELISA

Cell-free supernatants were obtained from in vitro and ex vivo studies after activation by using OVA peptide or fibroblast lysates. For IL-2 measurements, supernatants were collected 24 h after cell activation. For IFN-γ and for IL-10 and IL-17A measurements, supernatants were collected 48 h and 72 h, respectively, after cell activation. Sandwich ELISA was implemented for measuring cytokine concentrations in the supernatants, according to manufacturer's instructions.

Immunohistochemistry and Confocal Imaging Analyses

For in vivo vascularization analysis, the cell transplantation devices and the surrounding fibrosis were removed from the animal and fixed for 24 h in 4% Paraformaldehyde (PFA) and then in a sucrose solution (30%) for 48 h. Then, the devices were embedded in Optimal Cutting Temperature compound (OCT) and stored at ($-80$)° C. Horizontal cross-sections (20 μm thick) were cut with a cryostat (Lecia CM3050 S) and kept at ($-80$)° C. until use. Cross-sections were washed in PBS/TWEEN (0.05% v/v). Prior to staining, the primary antibody diluting buffer was used to block non-specific binding. Sections were then incubated with a primary monoclonal anti-mouse CD31 antibody (Biolegend; cat 910003) and stained with Alexa Flour 633-conjugated anti-rat IgG (Biolegend; cat 405416).

Confocal imaging of the sections was performed with a Nikon C1si laser scanning confocal microscope. Vessel density was calculated as percentage of Platelet endothelial cell adhesion molecule (PECAM), CD31-occupied area of the total image area, and was determined from 15 different fields, randomly selected from the PECAM-immunostained cross-sectional slides, by using the Imaris Software (Bitplane scientific solutions, South Windsor, Conn.).

For CD8+ cytotoxicity imaging, the CD8+ T cells were stained with SNARF1 (Invitrogen, CA, USA), according to manufacturer's instructions, prior to co-culturing with the NIH/3T3 fibroblasts. Twelve hours post co-culturing, cells in wells were fixed with 4% PFA. Prior to staining for Granzyme B, the primary antibody diluting buffer was used to block non-specific binding, and the cells then underwent permeabilization. Then, the cells were incubated with a fluor-conjugated primary monoclonal anti-mouse Granzyme B (Biolegend; cat 515405) overnight. Confocal imaging of the sections and the wells in which the CD8+ cytotoxicity assay was conducted was performed with a Nikon C1si laser scanning confocal microscope.

For in vitro splenocytes cultivation within the scaffold 72 h post activation images, the scaffolds were collected and fixed for 20 min in 4% PFA in DMEM buffer, followed by 24 h of incubation in a sucrose solution. After fixation, the devices were embedded in O.C.T and stored at ($-80$) ° C. Horizontal cross-sections (30 μm thick) were cut with a cryostat (Lecia CM3050 S) and kept at (−80) °C. until use. Cross-sections were washed in DMEM buffer. Prior to staining, 2% BSA in DMEM buffer was used to block non-specific binding. Sections were then incubated with a primary monoclonal anti-mouse CD11c antibody (Biolegend; cat 117302) and with a primary monoclonal anti-mouse CD4 antibody (Biolegend; cat 100402), and stained with Alexa Flour 488-conjugated anti rat IgG (Biolegend; cat 405418) and with Alexa Flour 546 anti-Armenian hamster IgG (Biolegend; cat 405423).

Statistics

All statistical analyses were performed using GraphPad Prism version 5.02 for Windows (GraphPad Software, San Diego, Calif.). All variables are expressed as mean±SEM. In vitro studies were compared by two-tailed unpaired t test (p<0.05). All ex vivo experiments were compared by one-way ANOVA with Tukey's post-hoc test (p<0.05).

Study Approval

All surgical and experimental procedures were reviewed and approved by the Institutional Animal Care and Use Committee (IACUC) of the Ben-Gurion University of the Negev, Israel.

Example 1

Construction and Immunoregulatory Properties of the Cell-Transplantation Device

The cell-transplantation device was an alginate scaffold (mean pore size=80 μm) that has been previously shown to be effectively vascularized after transplantation due to its macroporous structure. To enhance vascularization, the alginate scaffold was supplemented with affinity-bound vascular endothelial growth factor (VEGF) and platelet-derived growth factor (PDGF-ββ). The affinity-binding of the growth factors to alginate matrix was mediated by their interactions with alginate-sulfate, which constitutes 10% of the dry weight of the scaffold. We have previously demonstrated that growth factors of the heparin-binding proteins family, such as VEGF, PDGF-ββ, and TGF-β, interact with alginate-sulfate in a manner similar to their natural interactions with heparin/heparan-sulfate (FIG. 1A). Thus, we expected that affinity-binding of the growth factors to the alginate scaffold matrix will improve their biological function.

Based on this expectation, we generated an immunotolerant microenvironment by affinity-binding TGF-β to an alginate-sulfate/alginate scaffold (FIG. 1A, and see Materials and Methods for details). This process prolonged the presentation of TGF-β, as compared to when TGF-β was non-specifically adsorbed to a pristine alginate scaffold. An ELISA of TGF-β revealed that 30.2%±0.8% of the initial loaded afTGF-β were still presented in the matrix after 7 days in the alginate sulfate-containing scaffold, while only 5.2%±0.3% were retained in the pristine scaffold (FIG. 1B). Importantly, the released TGF-β found in the media and the TGF-β affinity-bound to the alginate/sulfated alginate matrix (afTGF-β) similarly activated SMAD2 phosphorylation in fibroblast monolayers (FIG. 1C, D). Of note, afTGF-β showed similar activity when it was still affinity bound to the matrix and after it was dissociated from the scaffold, indicating that cells can interact with TGF-β both in its affinity-bound form and upon its release.

Figure 13A:
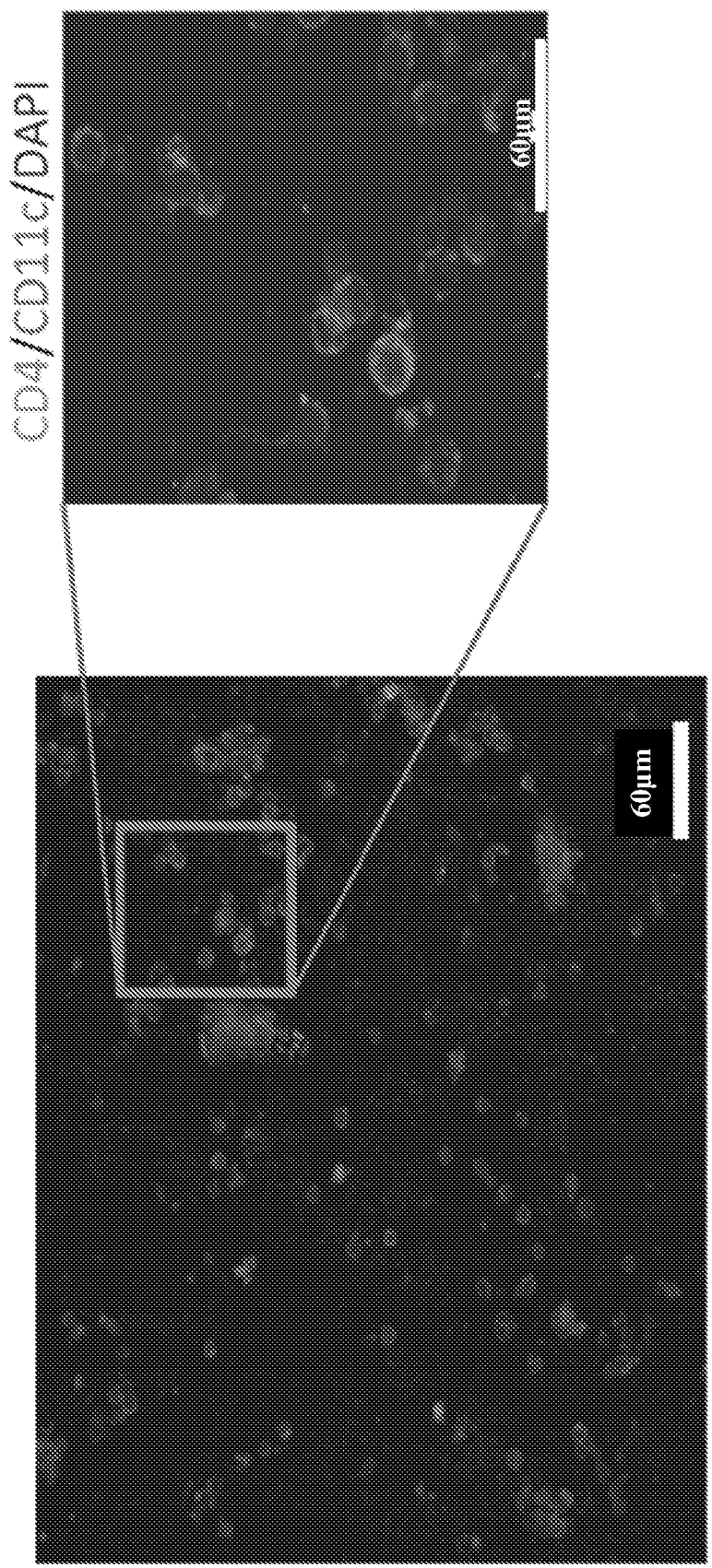
FIG. 13A shows confocal image of splenocytes isolated from spleens of OTII mice and seeded within the alginate scaffold, with or without OVA peptide (final peptide concentration: 20 g/ml), 72 h post activation.
Figure 13B:
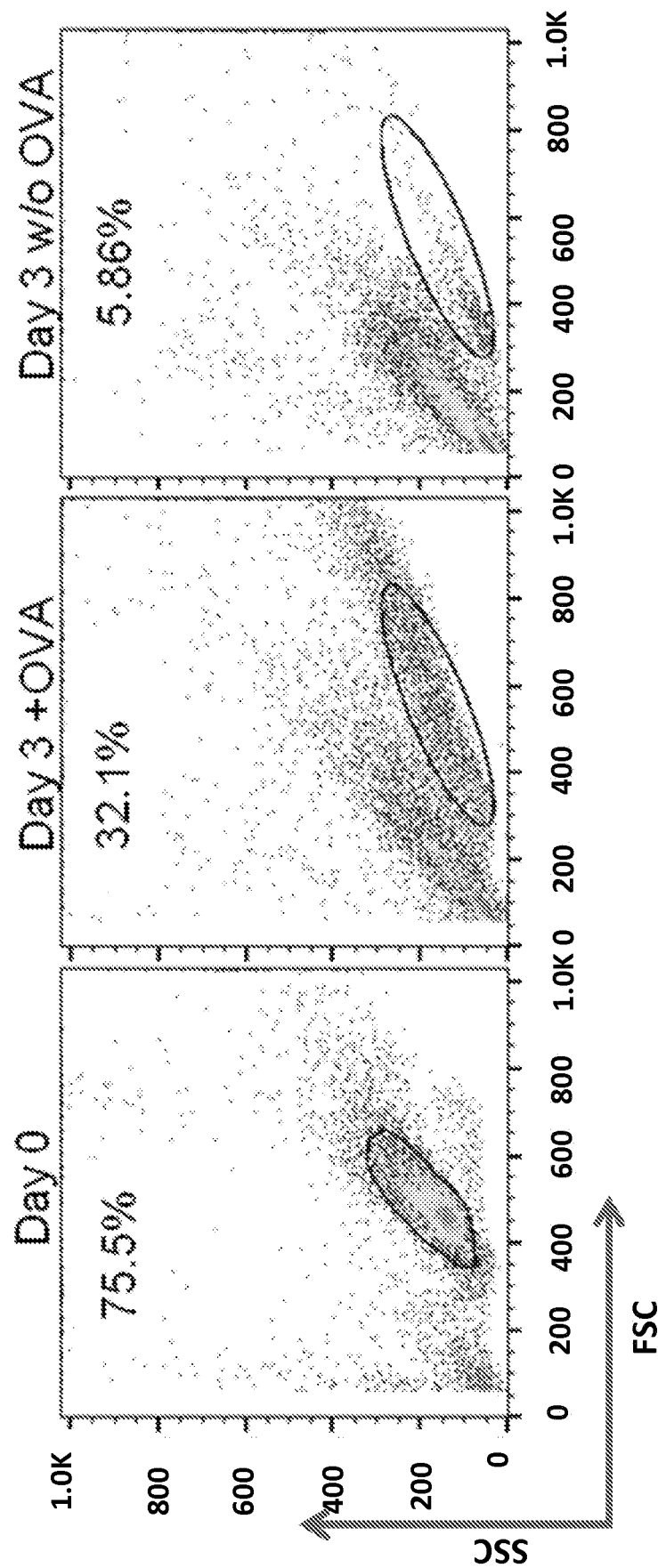
FIG. 13B shows representative FACS plots of lymphocytes at seeding day and 3 days post activation.
Figures 14A, 14B:
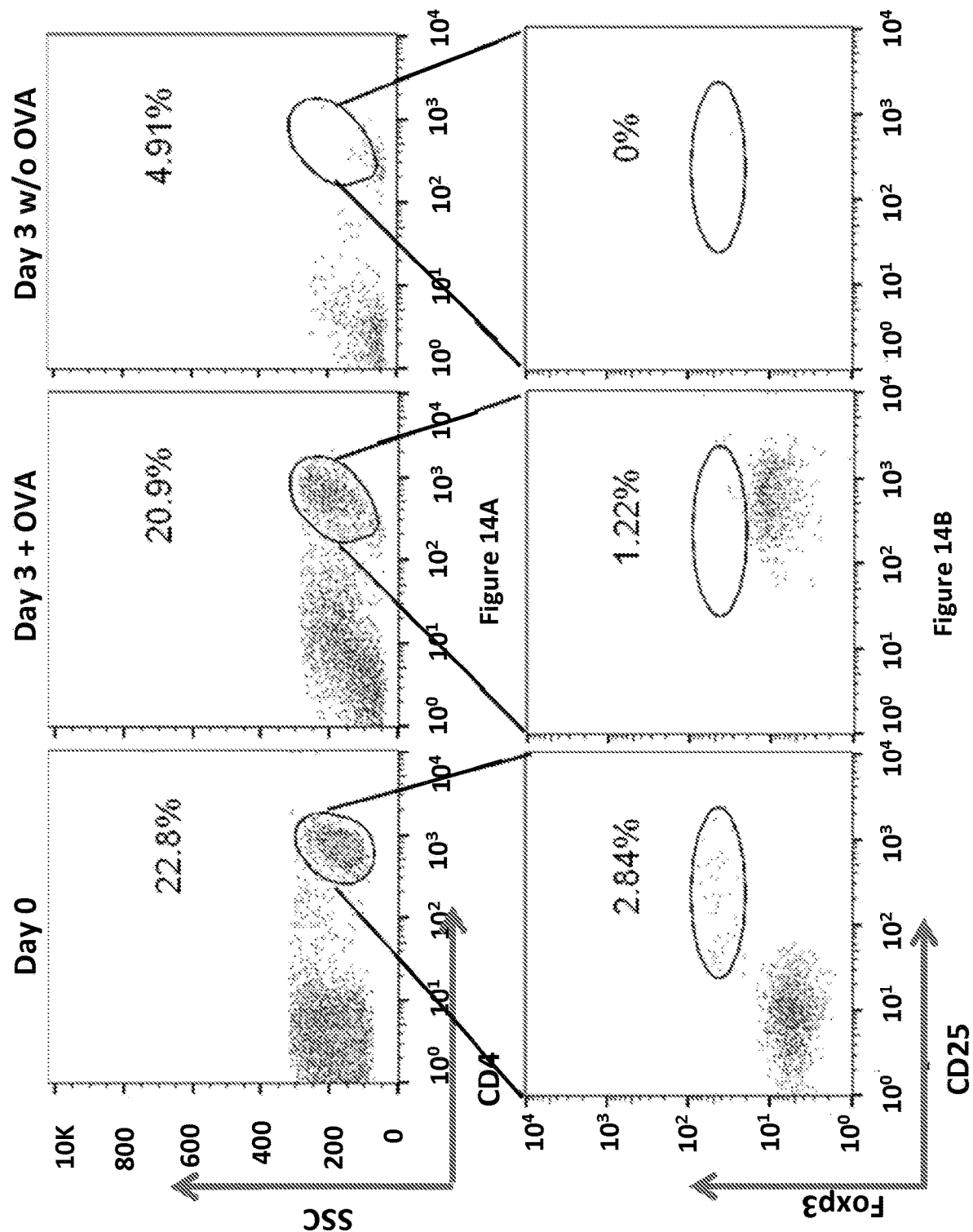
FIG. 14 shows in the upper row FACS plots of CD4+ T cells population as found prior to seeding and 3 days post seeding, with or without activation, demonstrating that the OVA activation was effective in maintaining CD4+ T cells in culture. The lower row shows FACS plots of CD4+CD25+ Foxp3+ Tregs population, as found before seeding and 3 days post seeding, with or without OVA activation, demonstrating that it supports CD4+ activation by the OVA peptide.
Figure 15A:
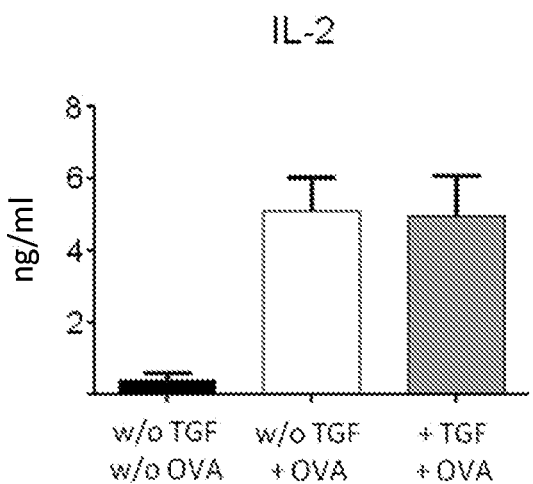
FIG. 15A shows a graph measuring the secretion levels of IL-2 from CD4 T cells (magnetically separated from OTII mice) co-cultured ($0.5\times10^6$ total cells/culture) within the alginate scaffold with bone marrow DCs within the alginate scaffold and with or without afTGF-β (50 ng/scaffold), indicating that the T cells were activated by the OVA peptide.
Figure 15B:
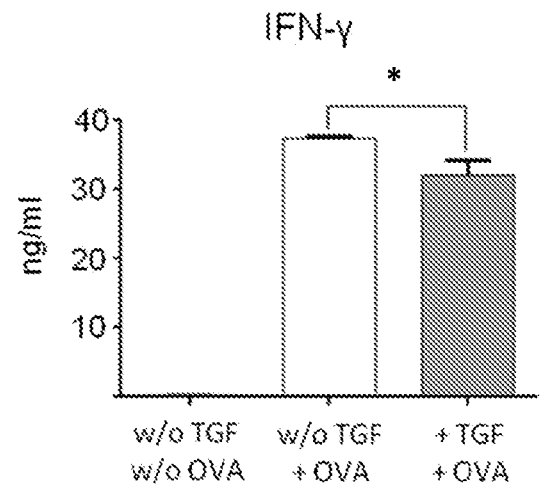
FIG. 15B shows a graph measuring the secretion levels of IFN-γ from CD4+ T cells (magnetically separated from OTII mice) co-cultured ($0.5\times10^6$ total cells/culture) within the alginate scaffold with bone marrow DCs within the alginate scaffold and with or without afTGF-β (50 ng/scaffold), indicating that the T cells were activated by the OVA peptide.
Figure 15C:
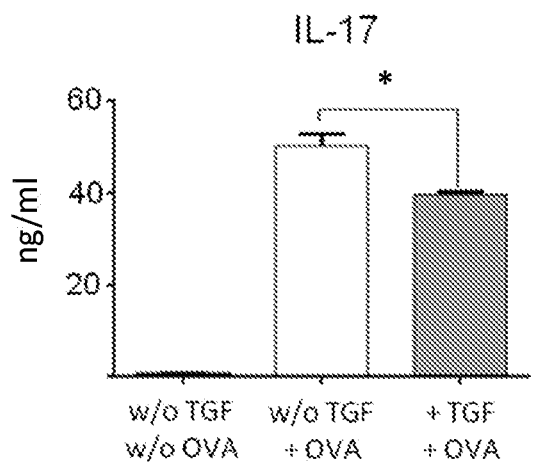
FIG. 15C shows a graph measuring the secretion levels of IL-17 from CD4+ T cells (magnetically separated from OTII mice) co-cultured ($0.5\times10^6$ total cells/culture) within the alginate scaffold with bone marrow DCs within the alginate scaffold and with or without afTGF-β (50 ng/scaffold), indicating that the T cells were activated by the OVA peptide. A significant decrease in IFN-γ and IL-17 levels in the presence of afTGF-β indicates the immunoregulation of afTGF-β.
Figure 15D:
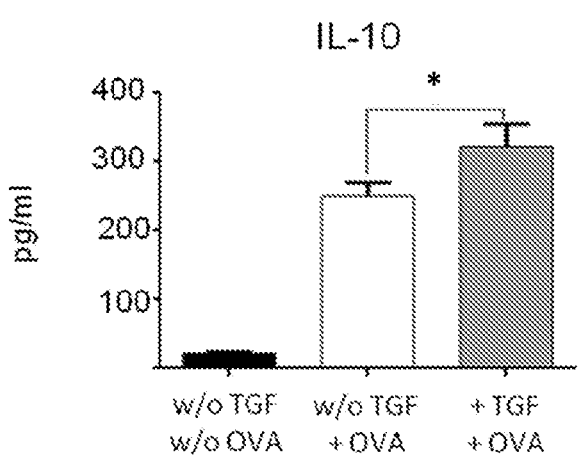
FIG. 15D shows a graph measuring the secretion levels of IL-10 from CD4+ T cells (magnetically separated from OTII mice) co-cultured ($0.5\times10^6$ total cells/culture) within the alginate scaffold with bone marrow DCs within the alginate scaffold and with or without afTGF-β (50 ng/scaffold), indicating that the T cells were activated by the OVA peptide.
Figure 15E:
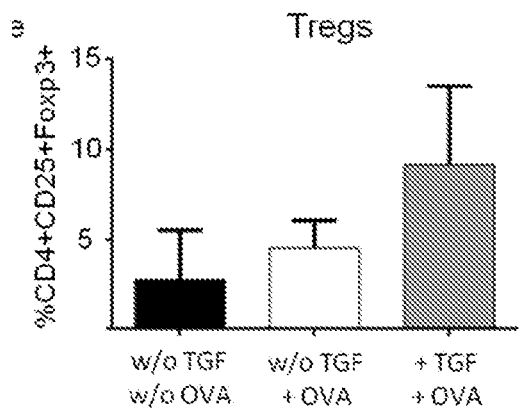
FIG. 15E shows a graph measuring levels of CD4+CD25+ Foxp3+ Tregs demonstrating a trend of increased levels of Tregs evident in cultures subjected to afTGF-β treatment. Results represent the mean values and SDs of 3 triplicates, and are compared by a two-way ANOVA, with Tukey's post-hoc test used to determine differences between the treatments. * $p<0.05$.

Next, we examined whether the spatial presentation of afTGF-β in alginate-sulfate/alginate scaffolds (afTGF-β construct) generates an immunoregulatory microenvironment. We performed preliminary studies to test whether total splenocyte leukocytes can be cultured, maintained viable, and elicit antigen-specific T-cell responses in the scaffold. To this end, erythrocyte-depleted spleen leukocytes were isolated from OTII OVA-TCR Tg mice (where lymphocytes are OVA-specific) and seeded in the scaffold, in the absence or presence of OVA as the T-cell activating peptide (FIG. 2A). FIG. 13A shows a typical construct, 3 days after cell seeding, with leukocytes distributed throughout the scaffold and with DCs and CD4 T cells in close proximity, allowing cell-cell interactions. OVA-induced T-cell proliferation was validated, revealing that 32% and 6% of the T cells survived with and without OVA activation, respectively (FIG. 13B). Approximately 20% of the surviving lymphocytes in the OVA-activated constructs were CD4+CD25+(FIG. 14A, B).

The immunoregulatory effect of afTGF-β was manifested in the cytokine profile and the appearance of CD4+CD25+ Foxp3+ regulatory T cells (Treg) in splenocytes (FIG. 2B-E) and in purified DCs (FIG. 15A-E) seeded within the afTGF-β construct. As shown in FIG. 15B-E, afTGF-β significantly suppressed the secretion of the pro-inflammatory cytokine IL-17A, significantly increased the regulatory cytokine IL-10, and did not affect the levels of secreted IL-2 or IFN-γ. Importantly, the presence of afTGF-β in the device led to a 2.88-fold increase in the frequency of CD4+CD25+ Foxp3+ T cells out of the total CD4+ T-cell population (30.6%±3.4% and 11.8%±3.1% of the total T-cell population with and without OVA, respectively; p=0.008, FIG. 3, FIG. 4A-C). Overall, this finding demonstrates that afTGF-β promotes an anti-inflammatory milieu within the cell transplantation device. Notably, the reduced levels of secreted IL-17 and the increased Treg frequencies observed in the afTGF-β constructs were not observed in the presence of anti-IL-10 (FIG. 5A-F) or when using splenocytes from CD11c$^{dnr}$ Tg mice expressing a dominant negative form of the human TGF-β receptor II gene under the CD11c promoter (FIG. 5G-H, FIG. 6A-6E).

Overall, our data point to a mechanism whereby afTGF-β signaling in DCs induces IL-10 upregulation, which then favors Treg differentiation and attenuates effector function of the CD4 T cells. This mechanism appears to be significantly more prominent in the 3-dimensional (3D) microenvironment of the transplantation device than when 2D cell monolayers are supplemented with soluble TGF-β (FIG. 16A-E, FIG. 17 A-B).

Example 2

In Vivo Vascularization of the Device

Vascularization of the cell transplantation device after implantation is crucial to support the viability and function of transplanted allocells, especially in highly dense-seeded cell devices. To enhance vascularization, our devices were supplemented with VEGF and PDGF-ββ. To discern the possibility that differences in cell behavior and viability in afTGF-β constructs (versus constructs lacking TGF-β) is due to differences in the extent of vascularization, we compared the extent of vascularization in afTGF-β constructs to that in TGF-β-lacking constructs; both types of constructs were seeded with an allogeneic NIH/3T3 fibroblast cell line from a Swiss murine origin infected to express GFP (5×10$^5$ cells/scaffold).

Figure 3:
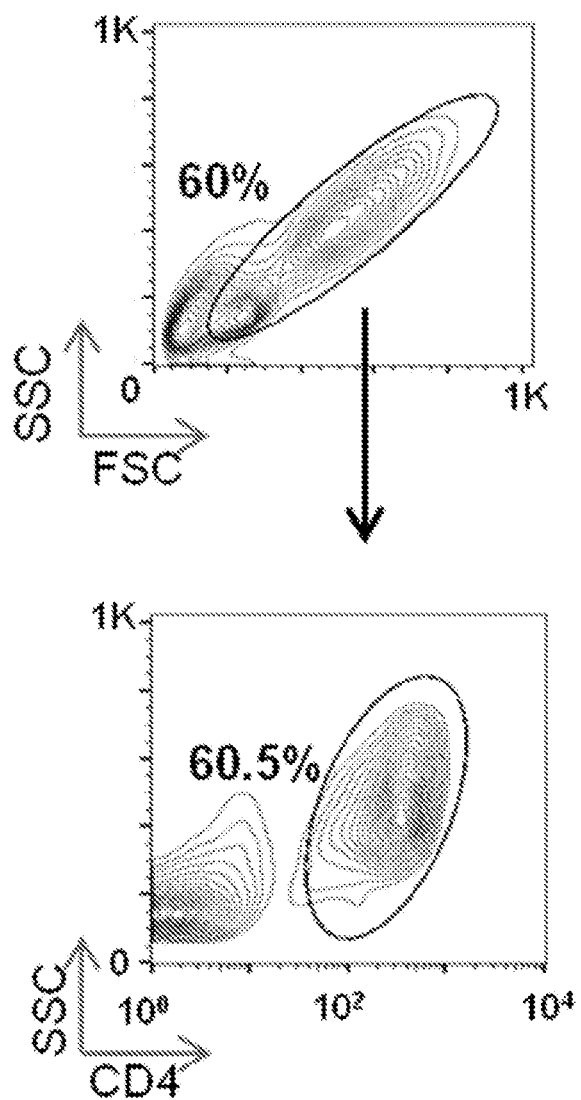
FIG. 3 shows FACS plots demonstrating lymphocytes and CD4 T cells gating representative FACS plots, 3 days post activation.
Figure 4A:
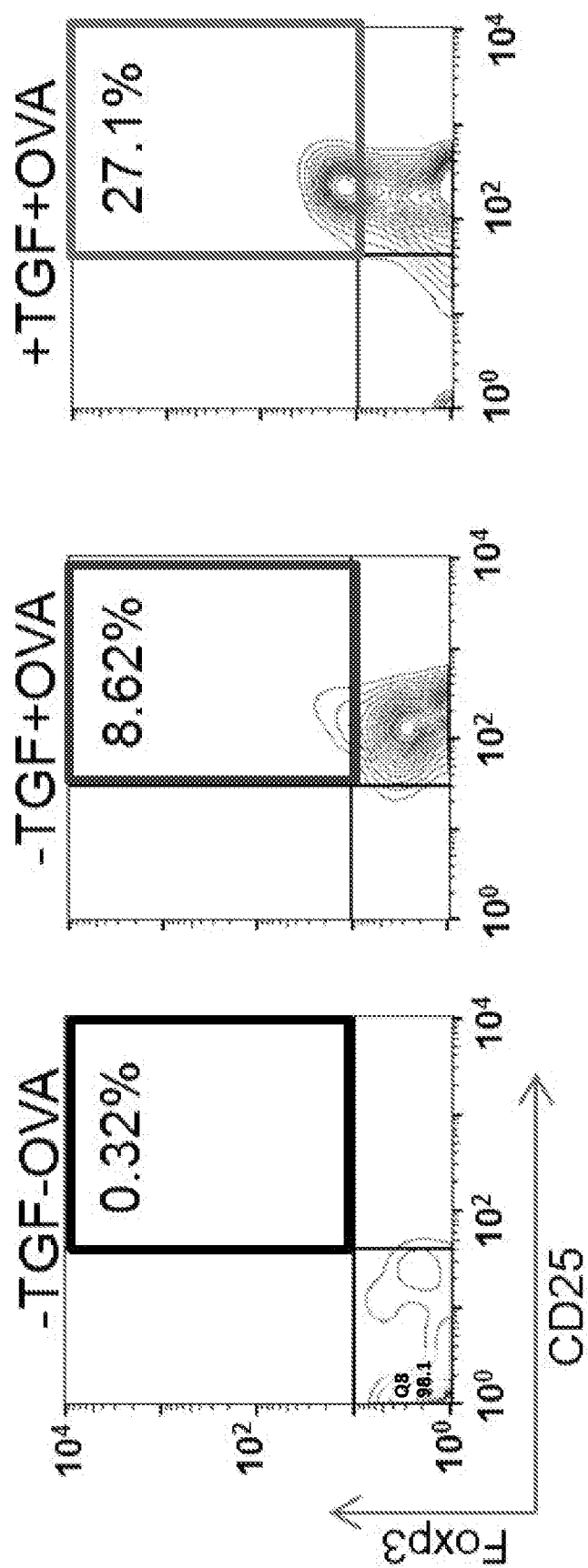
FIG. 4A shows representative FACS plots of CD4+ T cells expressing CD25 and Foxp3, 3 days post activation.
Figure 4C:
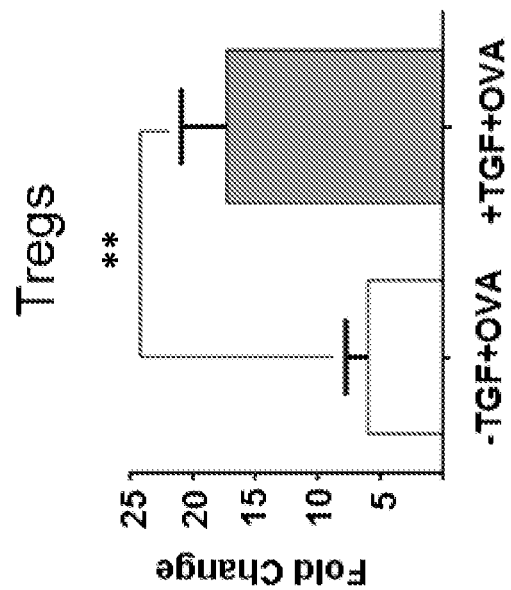
FIG. 4C shows a graph measuring percentage of Tregs from total CD4+ T cells with and without afTGF-β, as compared to -TGF-OVA control. Red: afTGF-β; blue: TGF-β-lacking; black: control. Data represent mean values of triplicates and SEM of 3 separate experiments. Results were compared by unpaired t-test, ** $p<0.01$.
Figure 4B:
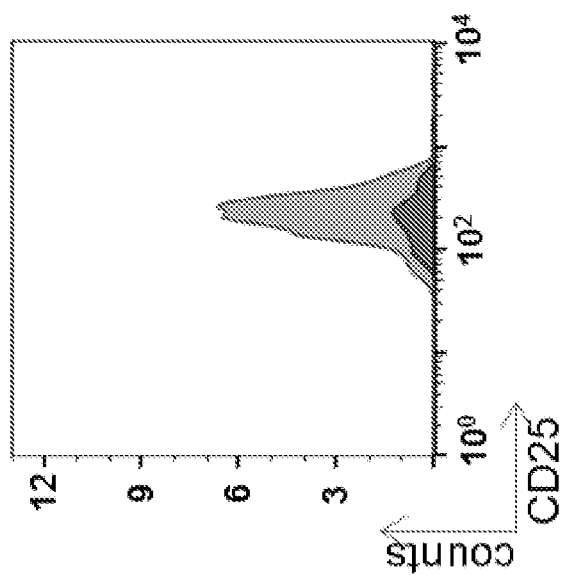
FIG. 4B shows a FACS histogram demonstrating increased frequency of Tregs within afTGF-β constructs compared to TGF-β-lacking constructs representative FACS histogram.
Figure 5A:
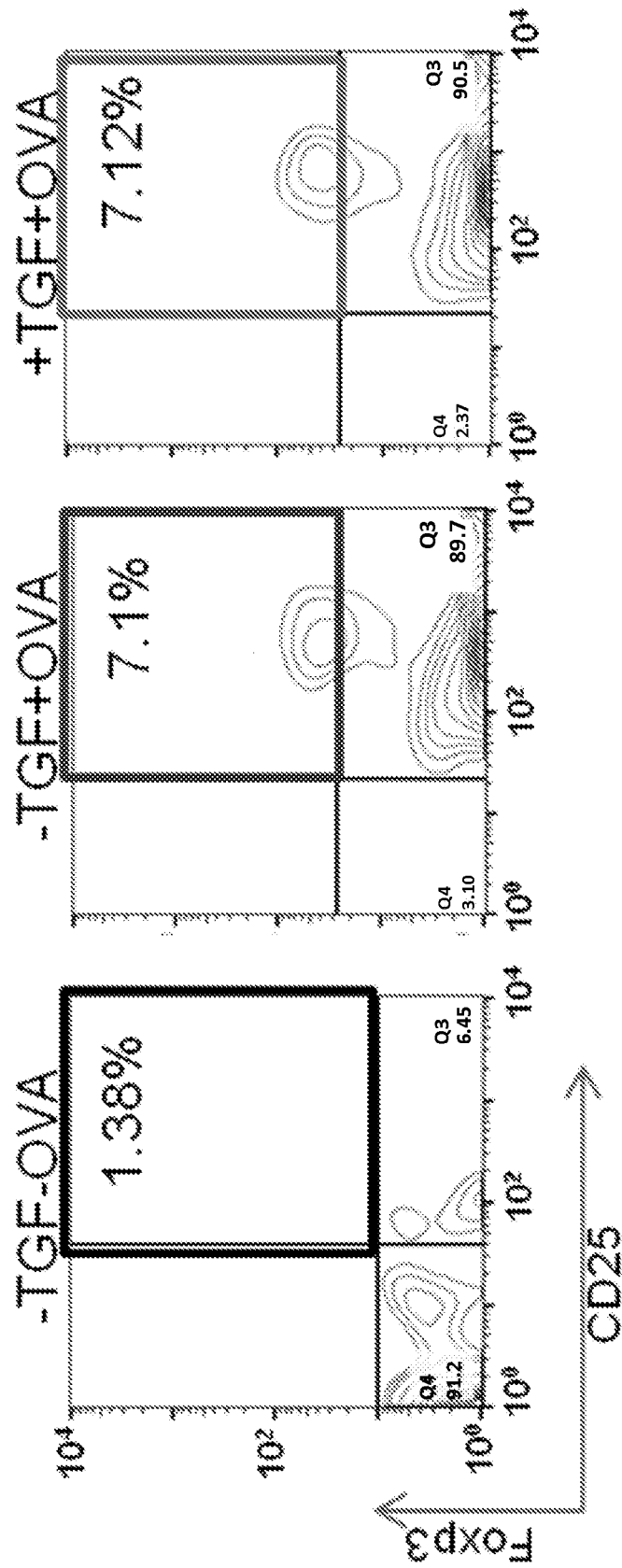
FIG. 5A shows representative FACS plots of CD4+ T cells expressing CD25 and Foxp3, 3 days post seeding. Splenocytes were cultured in afTGF-β constructs and TGF-β-lacking constructs and were stimulated with OVA in the presence of anti-IL-10 (1 ng/ml). Red: afTGF-β; blue: TGF-β-lacking; black: control.
Figure 5B:
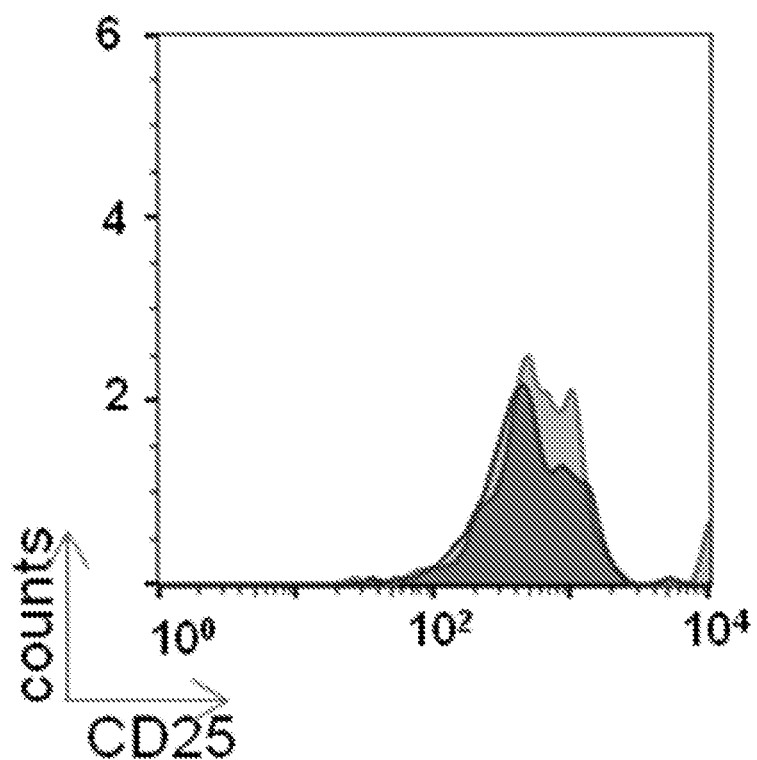
FIG. 5B shows representative FACS histogram showing no difference in the frequency of Tregs between afTGF-β constructs and TGF-β-lacking constructs. Red: afTGF-β; blue: TGF-β-lacking; black: control.
Figure 5G:
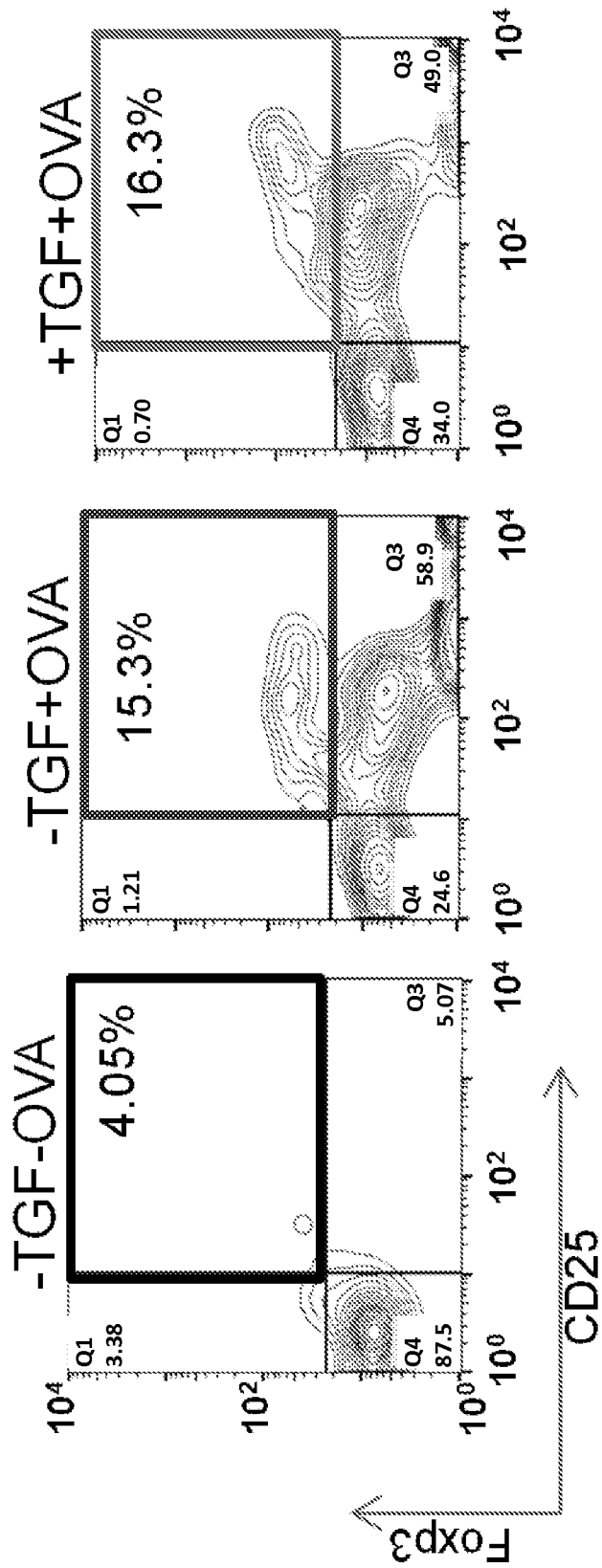
FIG. 5G shows representative FACS plots of CD25 and Foxp3 expressing CD4+ T cells 3 days post co-culturing. OVA T cells were co-cultured with splenocytes from CD11c$^{dnr}$ Tg mice within afTGF-β constructs and TGF-β-lacking constructs. Red: afTGF-β; blue: TGF-β-lacking; black: control.
Figure 5H:
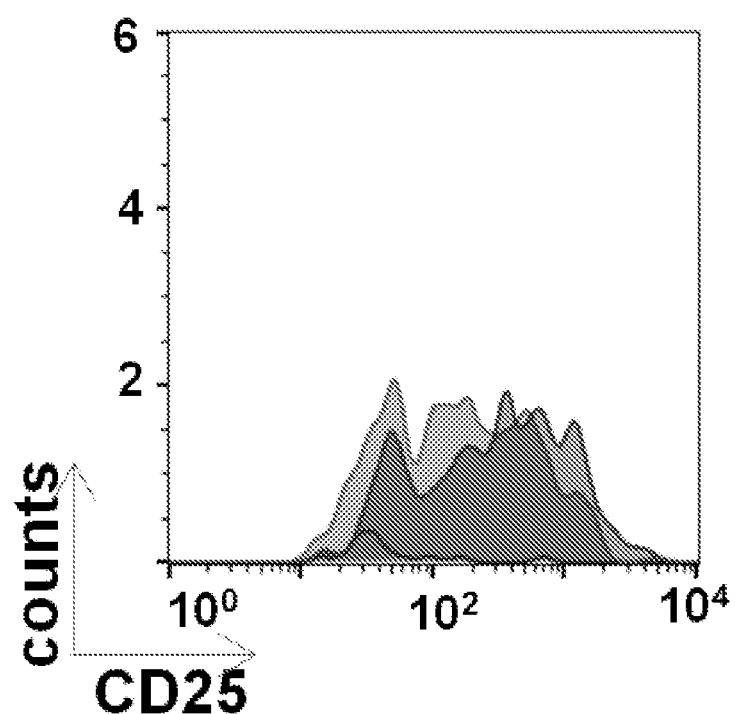
FIG. 5H shows representative FACS histogram showing no difference in Treg population within afTGF-β constructs and TGF-β-lacking constructs. Red: afTGF-β; blue: TGF-β-lacking; black: control.
Figure 7A:
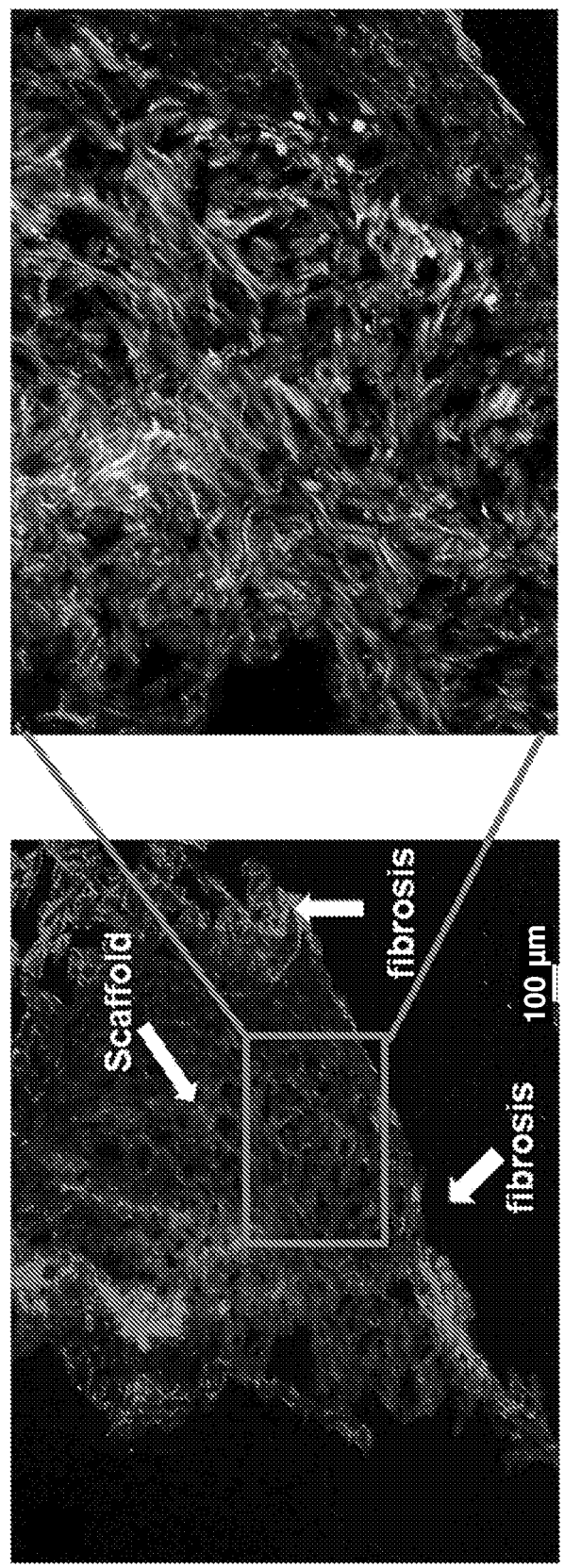
FIG. 7A shows PECAM (CD31) stained cryo-sections of retrieved devices containing fibroblasts 10 days post transplantation exhibit host endothelial cell penetration to the scaffold.
Figures 7B, 7C:
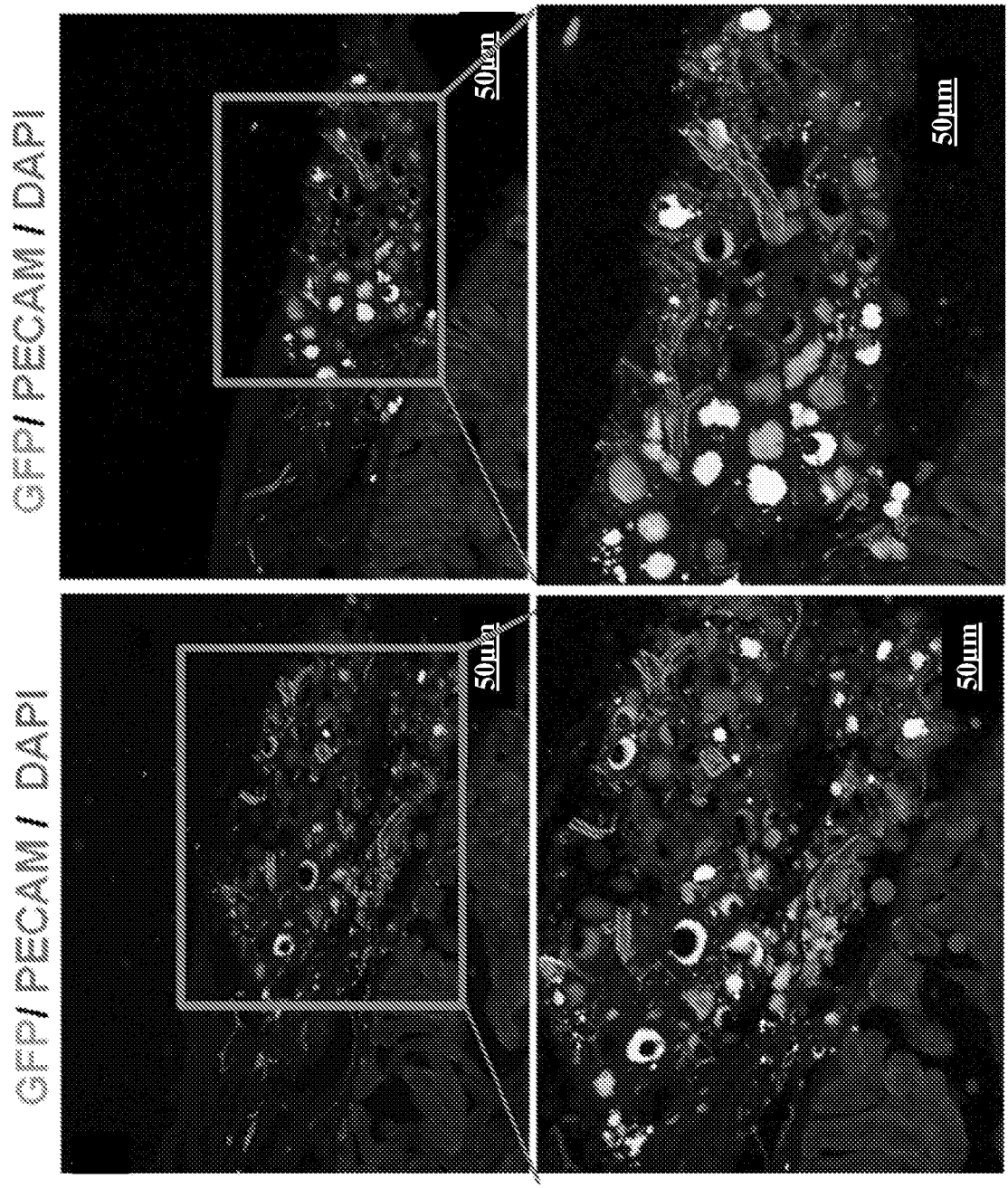
FIG. 7B shows confocal imaging of blood vessels (red) formed within the TGF-β-lacking construct containing allofibroblasts (green) 15 days post transplantation.
FIG. 7C shows confocal imaging of blood vessels (red) formed within afTGF-β constructs containing allofibroblasts (green) 15 days post transplantation.
Figure 8:
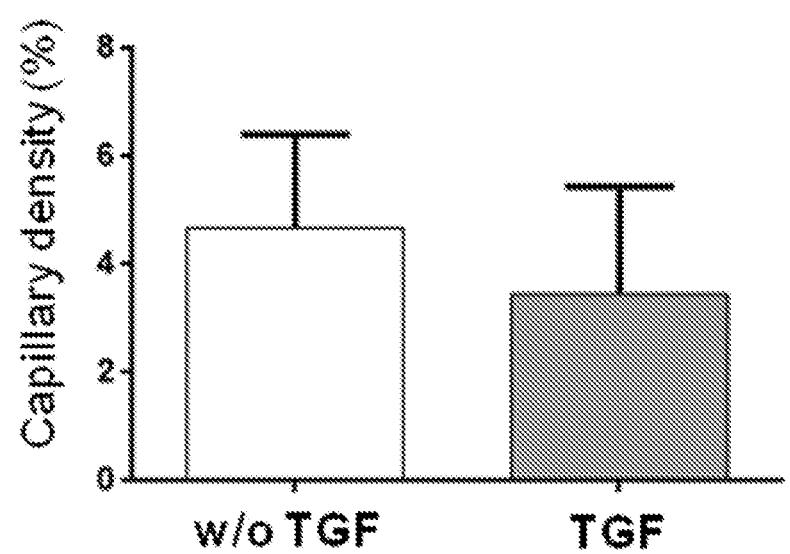
FIG. 8 shows the graph of blood vessel density calculated as the percent area occupied by PECAM staining divided by the total area of the section. Data were collected from 15 different fields, randomly selected from the PECAM-immunostained cross-sectional slides. n=5; results were compared with unpaired t-test, $p<0.05$.

FIG. 7A shows that, within 10 days after being transplanted under the kidney capsule, both cell-seeded devices were populated with PECAM+ (CD31) endothelial cells, forming blood capillaries scattered among the GFP-fibroblasts. By day 15, clear capillaries were observed in the transplanted constructs (FIG. 7B, C), occupying 3-4% of the cell devices with and without afTGF-β (FIG. 8).

Example 3

In Vivo Local Immunoregulation and Allofibroblast Graft Survival

The next sets of experiments confirmed, in vivo, the establishment of a local immunoregulatory microenvironment in the afTGF-β scaffold. Moreover, given the extensive vascularization in the device, the efficacy of such a potential transplantation device to maintain the viability and function of transplanted allofibroblasts was examined.

Figure 9A:
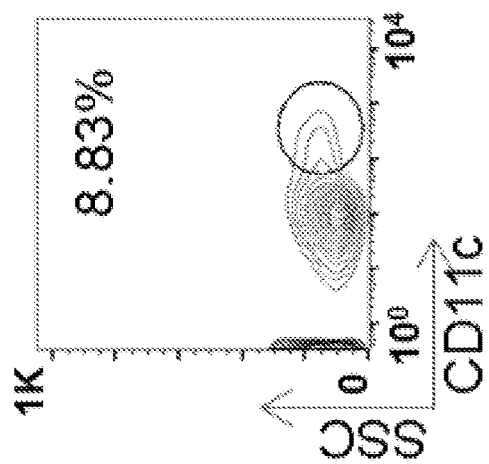
FIG. 9A shows penetrating cells to constructs without afTGF-β, representative FACS plot demonstrating CD11c+ cells gating.
Figure 9B:
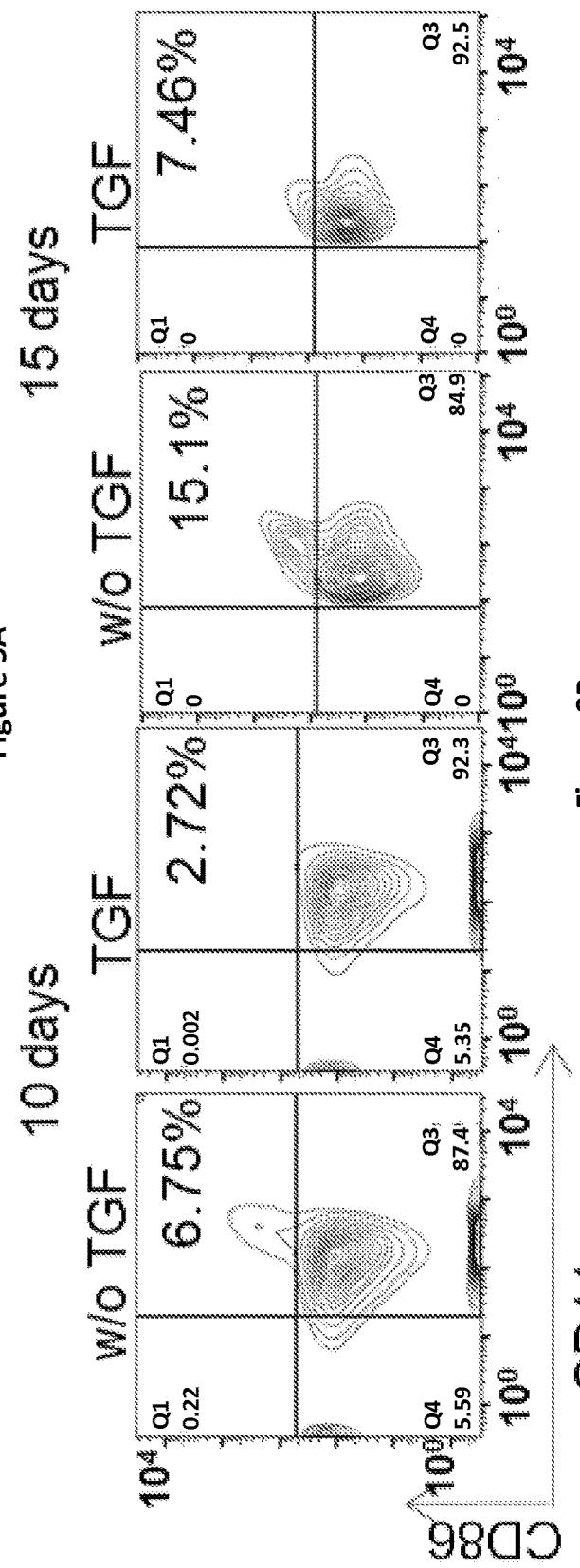
FIG. 9B shows FACS plots demonstrating increased levels of mature CD11c+CD86+ DCs in TGF-β-lacking constructs compared to afTGF-β constructs.
Figure 9C:
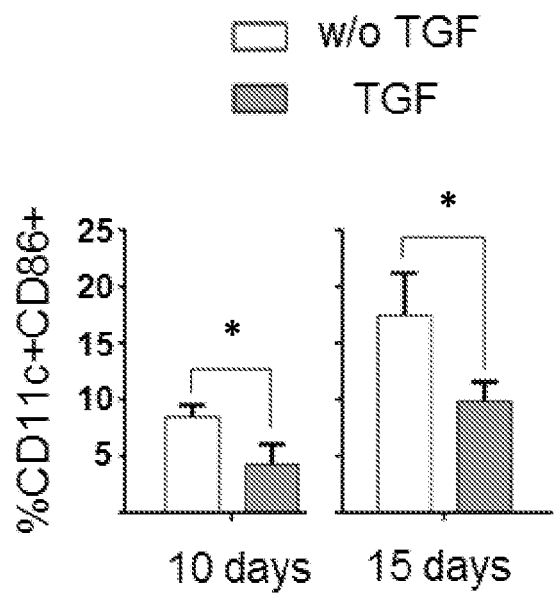
FIG. 9C shows a graph demonstrating that percentage of the CD11c+CD86+ population from total CD11c+ cells is significantly higher in TGF-β-lacking constructs.
Figure 9D:
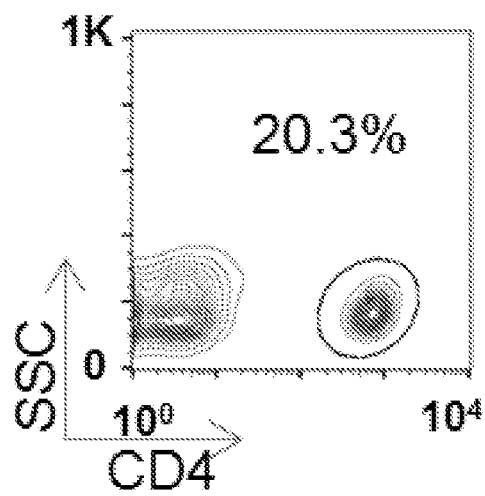
FIG. 9D shows a FACS plot demonstrating gating of CD4 T cells penetrating TGF-β-lacking constructs.
Figure 9E:
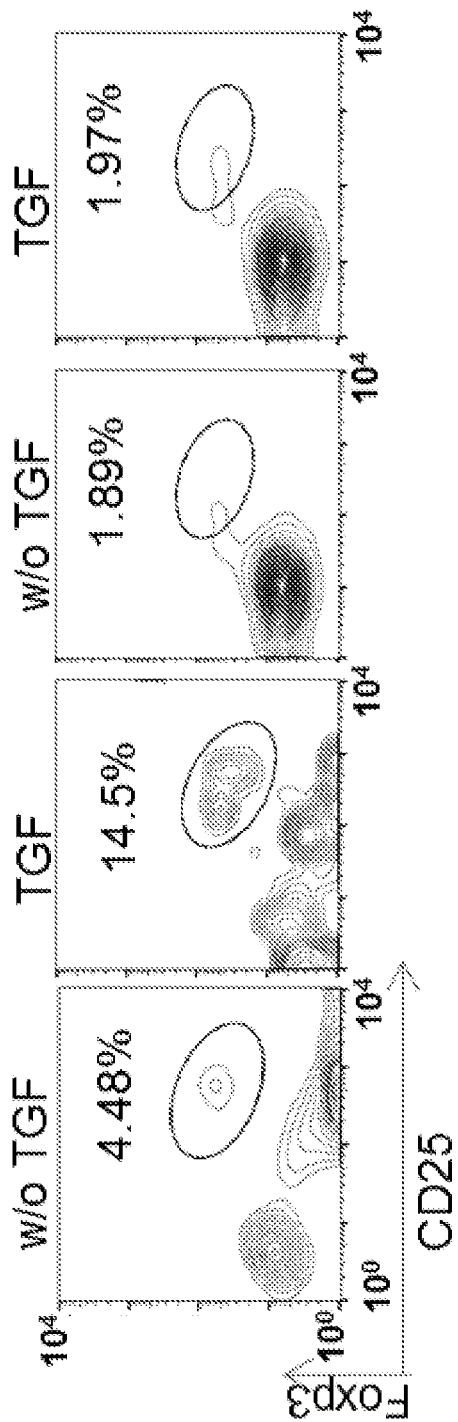
FIG. 9E shows FACS plots demonstrating Tregs percentage from total penetrating CD4+ T cells gated in afTGF-β constructs and TGF-β-lacking constructs.
Figure 9F:
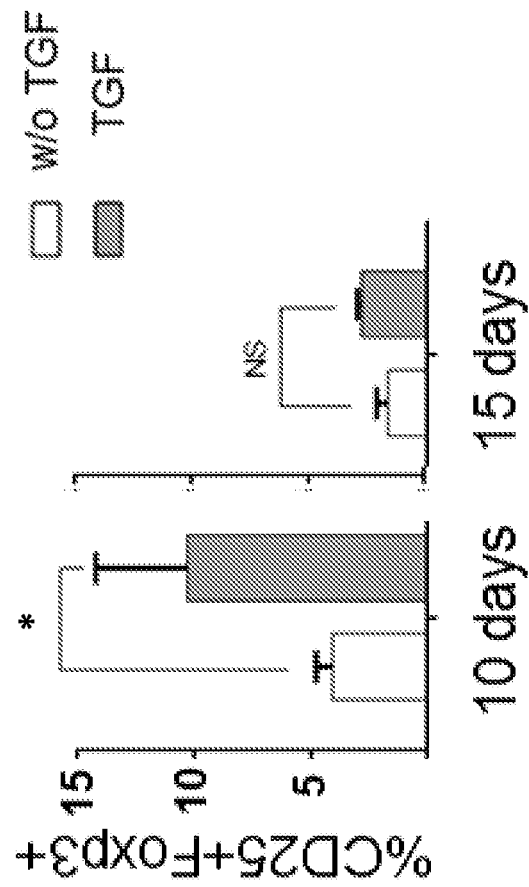
FIG. 9F shows a graph demonstrating a significantly larger Tregs population from total CD4+ T cells penetrating the device in afTGF-3 constructs at 10 days post transplantation.
Figure 9G:
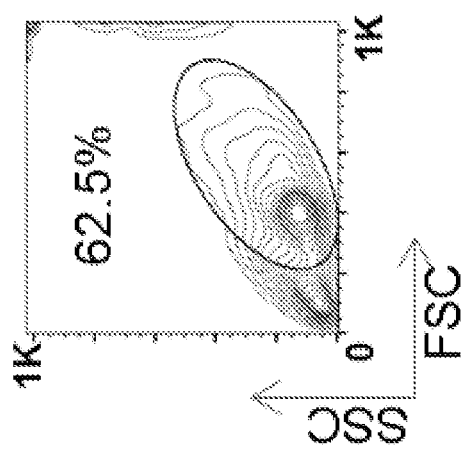
FIG. 9G shows a FACS plot demonstrating gating of penetrating lymphocytes in TGF-β-lacking construct.
Figure 9H:
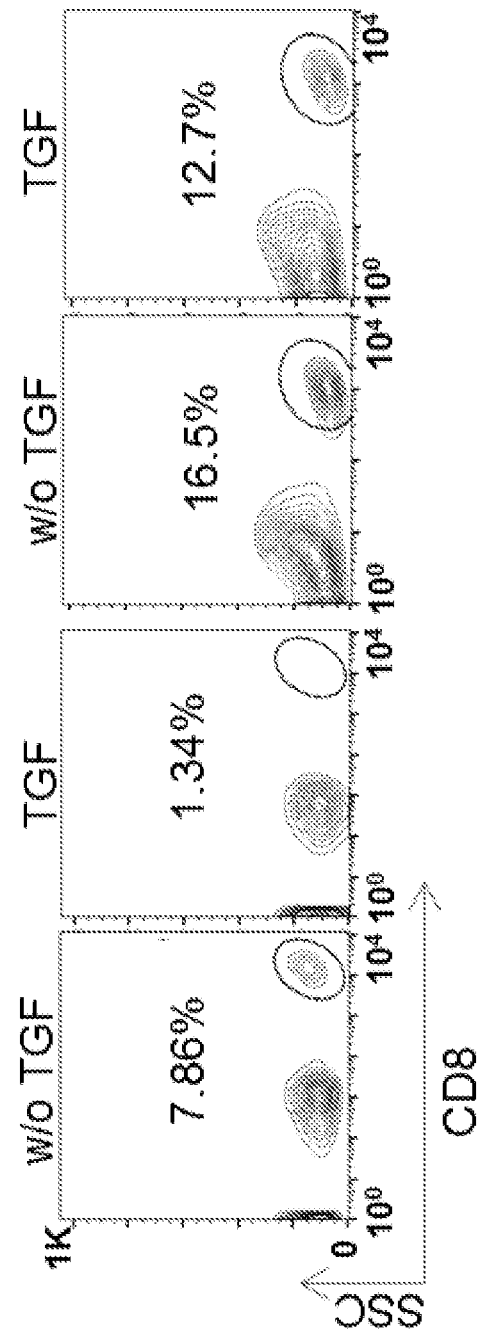
FIG. 9H shows FACS plots demonstrating CD8+ penetrating T cells in constructs with and without afTGF-β.
Figures 9I, 9J:
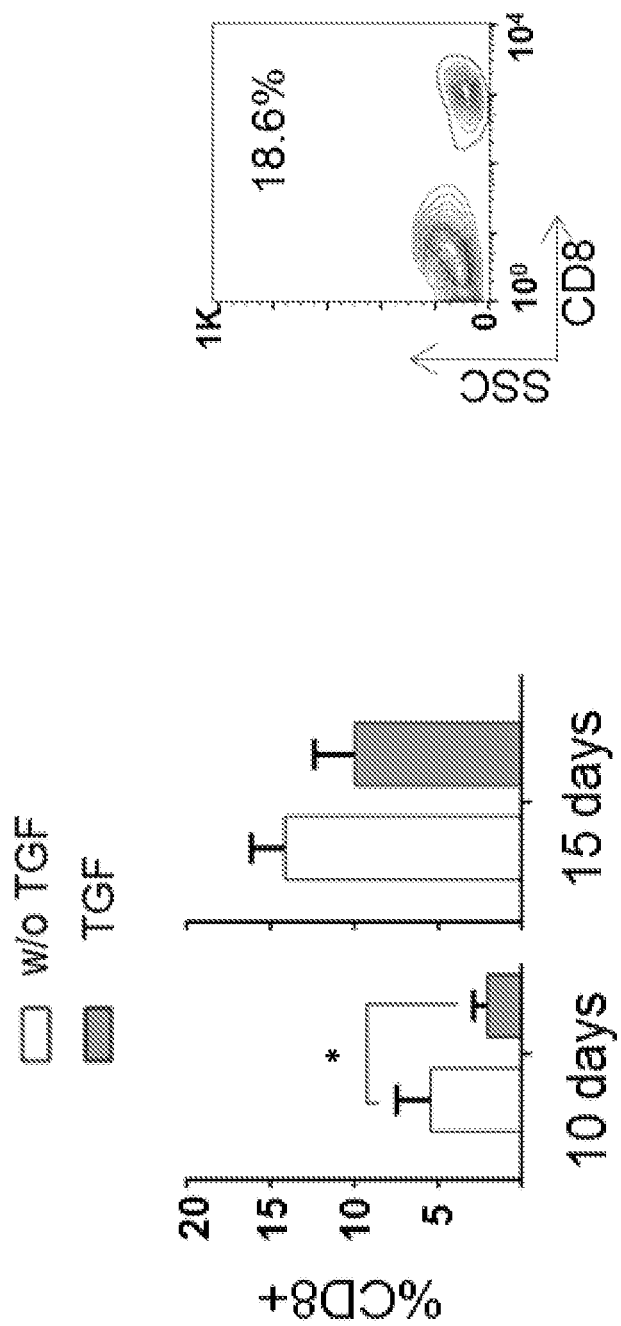
FIG. 9I shows a graph demonstrating percentage of penetrating CD8+ population from total penetrating lymphocytes in afTGF-β constructs and in TGF-β-lacking constructs.
FIG. 9J shows a FACS plot demonstrating gating of penetrating CD8+ T cells in TGF-β-lacking construct.
Figure 9K:
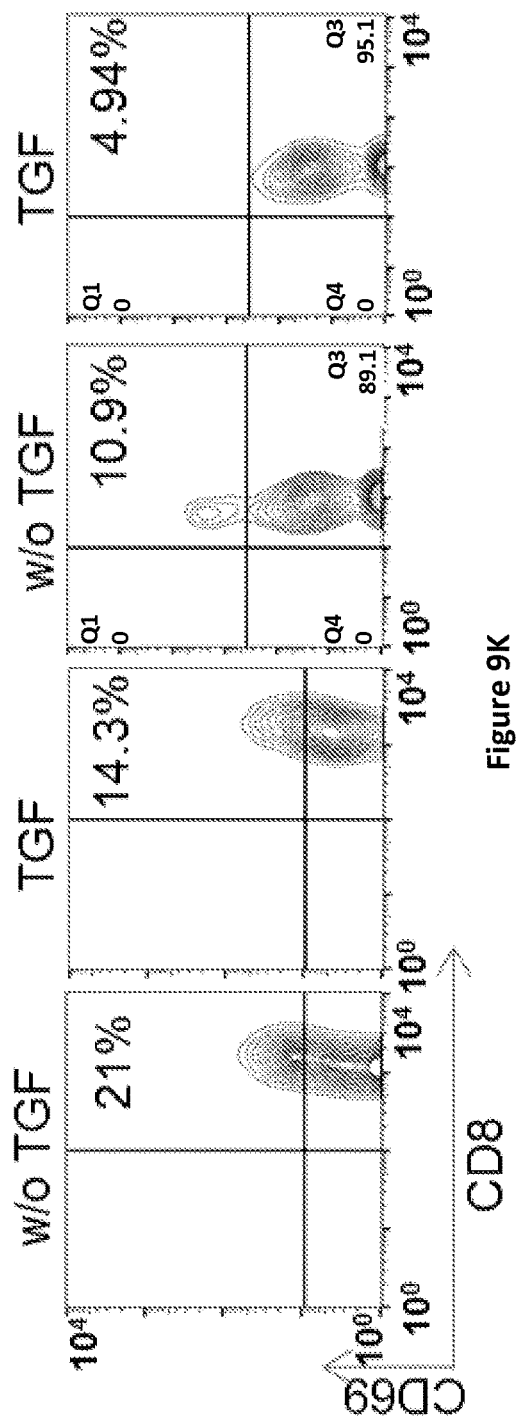
FIG. 9K shows FACS plots demonstrating active CD8+CD69+ penetrating T cells in constructs with and without afTGF-β.
Figure 9L:
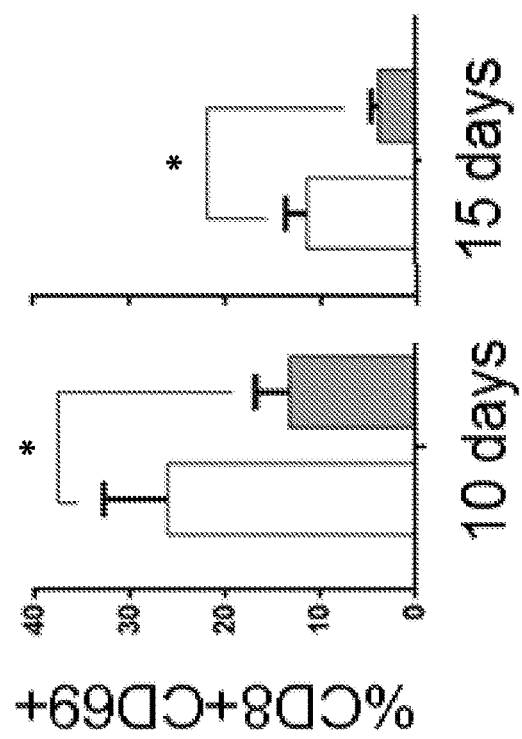
FIG. 9L shows a graph demonstrating lower active CD8+CD69+ T cells percentage from total CD8+ penetrating T cells with afTGF-β than in TGF-β-lacking constructs.

A FACS analysis of the constructs retrieved 10 and 15 days post-transplantation revealed a significant lower percentage of mature CD11c+ DCs expressing the co-stimulatory molecule CD86 (FIG. 9A-C), and a significantly higher percentage of CD4+CD25+Foxp3+ Tregs (FIG. 9D-F, $p<0.05$), in the afTGF-β constructs than in the TGF-β-lacking constructs. The increase in Tregs was evident only on day 10 post transplantation. Accordingly, a significantly lower percentage of CD8+ T cells was evident in the afTGF-β constructs, as compared with constructs lacking TGF-β, on day 10 post transplantation (2.1%±0.4% versus 5.5%±0.9%, respectively, $p=0.019$) (FIG. 9G-I). Furthermore, a significant decrease in the fraction of CD8 T cells expressing the activation marker CD69 was observed in afTGF-β constructs, as compared with constructs lacking TGF-β, at 10 days post transplantation (13.4%±3.5% versus 22.9%±9.3%, respectively, $p=0.015$) and at 15 days post transplantation (4%±0.8% versus 12.0%±2.5%, respectively, $p=0.0001$) (FIG. 9J-L).

Figure 10D:
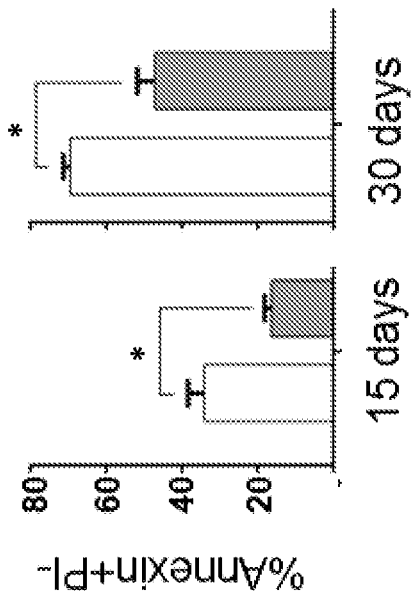
FIG. 10D shows a graph demonstrating that percentage of viable fibroblasts, (GFP+AnnexinV−PI−, was significantly higher in devices with afTGF-β.
Figure 10E:
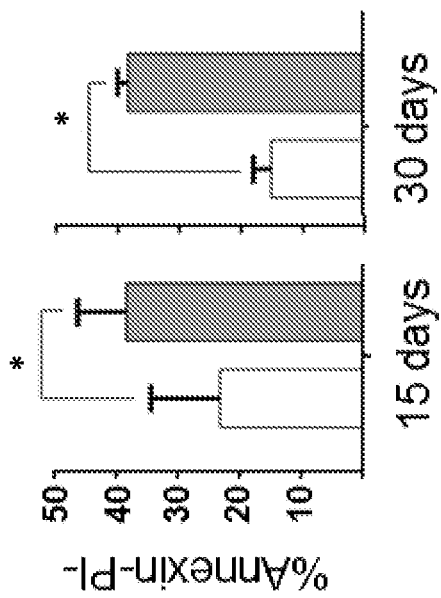
FIG. 10E shows a graph demonstrating that percentage of apoptotic fibroblasts (GFP+AnnexinV+PI−) was significantly higher in TGF-β-lacking constructs.
Figure 10F:
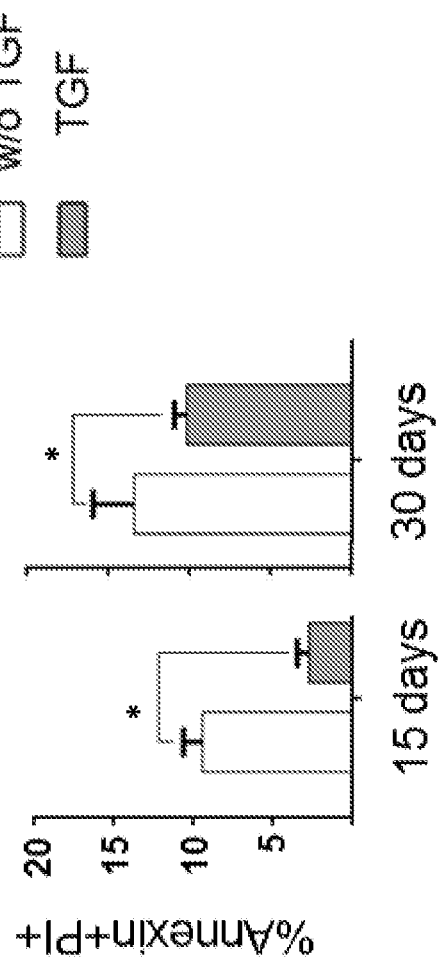
FIG. 10F shows a graph demonstrating that percentage of dead fibroblasts (GFP+AnnexinV+PI+) was significantly higher in TGF-β-lacking constructs. n=12, results were compared at each time point by unpaired t-test*$p<0.05$.

To determine whether the immunotolerant environment affects allofibroblast survival, we determined the number of viable allofibroblasts and the frequency of cells undergoing apoptosis. GFP+ cells retrieved from the devices were calculated as the percentage of GFP+ cells from the total GFP+ cells that were present in the device at 3 days post transplantation (FIG. 17 C, D). This baseline was selected to eliminate cell deaths that are not associated with T-cell-mediated cytotoxicity. The percentage of retrieved allofibroblasts at 15 days post transplantation was 50.4%±2% and 44.6%±0.7% in the afTGF-β and in the TGF-β-lacking constructs, respectively ($p<0.05$, FIG. 10A, B), with a trend of a higher percentage of retrieved allofibroblasts from the afTGF-13 device observed 30 days post transplantation. The viability of the surviving allofibroblasts was further validated by FACS analysis of the GFP cells labeled with Annexin V and PI (FIG. 10C). At 15 days post transplantation, the percentage of viable allofibroblasts (GFP+Annexin–PI–) was significantly higher in the afTGF-β constructs than in the TGF-β-lacking constructs (38.5%±3.5% and 23.2%±5.0%, respectively, $p=0.038$, FIG. 10D). Accordingly, the percentage of GFP+AnnexinV+PI-apoptotic cells and of GFP+AnnexinV+PI+ cells from total number of GFP+ allofibroblasts at 15 days and 30 days post transplantation was significantly lower in the afTGF-β constructs than in the TGF-β-lacking constructs (FIG. 10E, F). These data indicate that the local presentation of afTGF-β in the constructs maintains infiltrating DCs in their immature state, thereby increasing the frequency of Tregs and suppressing the activation of cytotoxic CD8 T cells.

Example 4

Affinity-Bound TGF-β Suppresses the Activation of Allo-Cell Specific Peripheral T Cells A major obstacle in cell or tissue transplantation is that immunosuppressive drugs are not antigen-specific and, thus, compromise host defense mechanisms. In addition, drug withdrawal often results in a rebound immune response, eventually leading to graft rejection. Long-term graft survival without compromising host immunity may be achieved by inducing allograft-specific T-cell tolerance. To determine whether the vascularized afTGF-β construct induces allofibroblast-specific peripheral tolerance, splenocytes were isolated from mice on day 15 and on day 30 post transplantation and examined for allofibroblast-specific T-helper and T-cytotoxic responses. As compared with the transplantation of TGF-β-lacking constructs, splenocytes excised from mice transplanted with afTGF-β constructs have a significantly reduced allofibroblast-specific Th17 effector function on day 15 (FIG. 11A; 55.5% secreted IL-17 compared to splenocytes excised from mice transplanted with TGF-β-lacking constructs, $p<0.05$). Strikingly, these splenocytes also show diminished Th1 and/or CD8 T-cell effector functions on day 30 post transplantation (FIG. 11B-C; 45.2% and 20.9% secreted IL-2 and IFN-γ compared to splenocytes excised from mice transplanted with TGF-β-lacking constructs, respectively, $p<0.05$). IL-10 secretion levels were not significantly different between the groups (FIG. 11D).

Figure 11E:
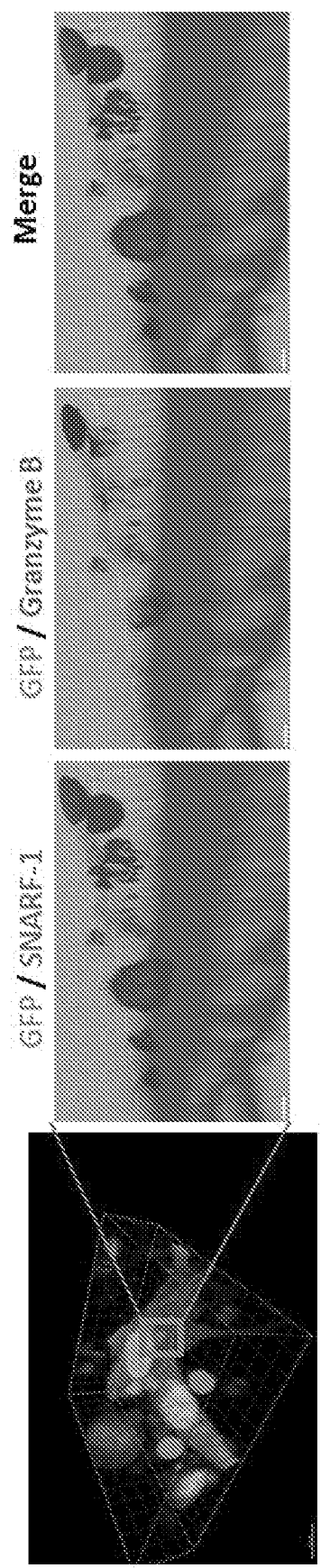
FIG. 11E shows a representative confocal image of cytotoxic CD8 (Granzyme B stained CD8+, blue) T cell forming a synapse with an allofibroblast in vitro that was captured during the cytotoxicity assay, wherein CD8+ T cells were magnetically isolated 15 and 30 days post transplantation from whole splenocytes of hosts that were transplanted with or without afTGF-β and WT mice, and subsequently were co-cultured with allofibroblasts at a ratio of 1:4.

Next, we determined whether the allocell-specific CD8 T-cell cytotoxicity response is also suppressed in mice transplanted with afTGF-β constructs. Splenocytes were thus isolated from the transplanted mice and from wild-type mice, and CD8 T cells were then isolated (as described in Methods and in FIG. 17E) and co-cultured with allofibroblasts at a cell ratio of 1:4, respectively. Confocal imaging showed that CD8+ T cells isolated from mice transplanted with TGF-β-lacking constructs formed an immunological synapse with allofibroblasts and exerted cytotoxicity (FIG. 11E and FIG. 18).

Figure 11F:
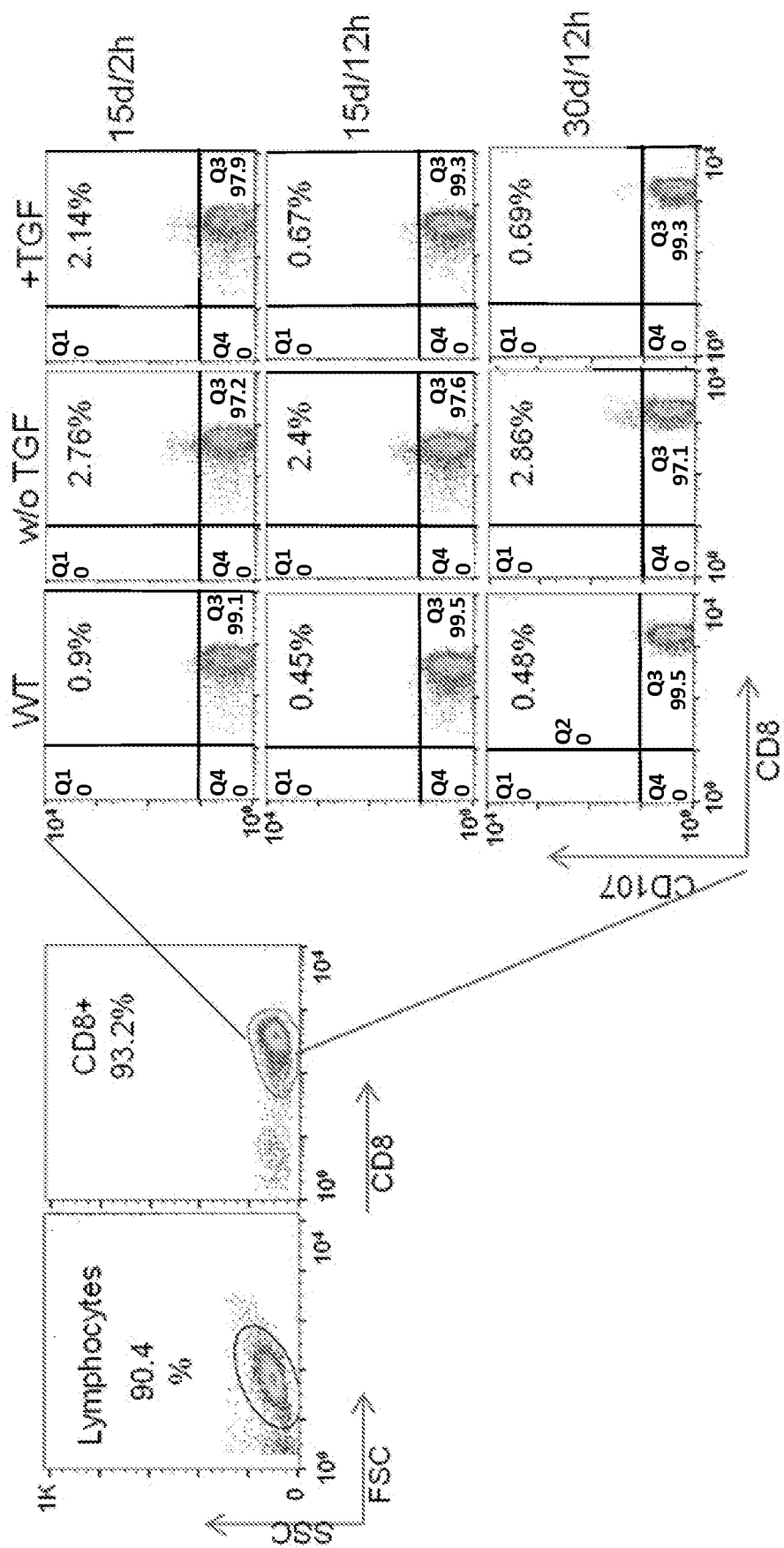
FIG. 11F shows representative FACS plots of CD8+ CD107+ cells co-cultured with fibroblasts in the cytotoxicity assay.
Figure 12A:
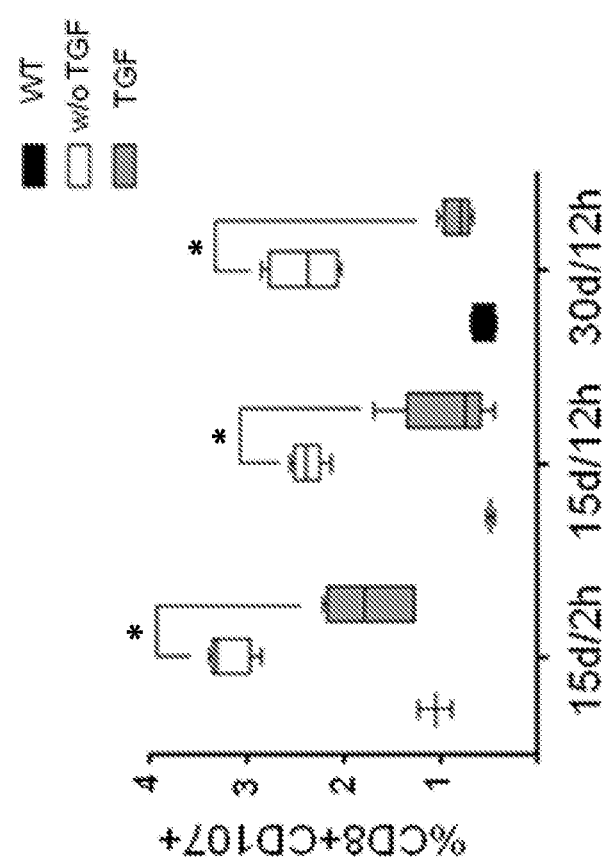
FIG. 12A shows a graph demonstrating that percentage of cytotoxic CD8+CD107+ T cells from total CD8+ cells is significantly higher when generated from hosts transplanted with TGF-β-lacking constructs, as compared with afTGF-3 constructs and WT mice.
Figure 12B:
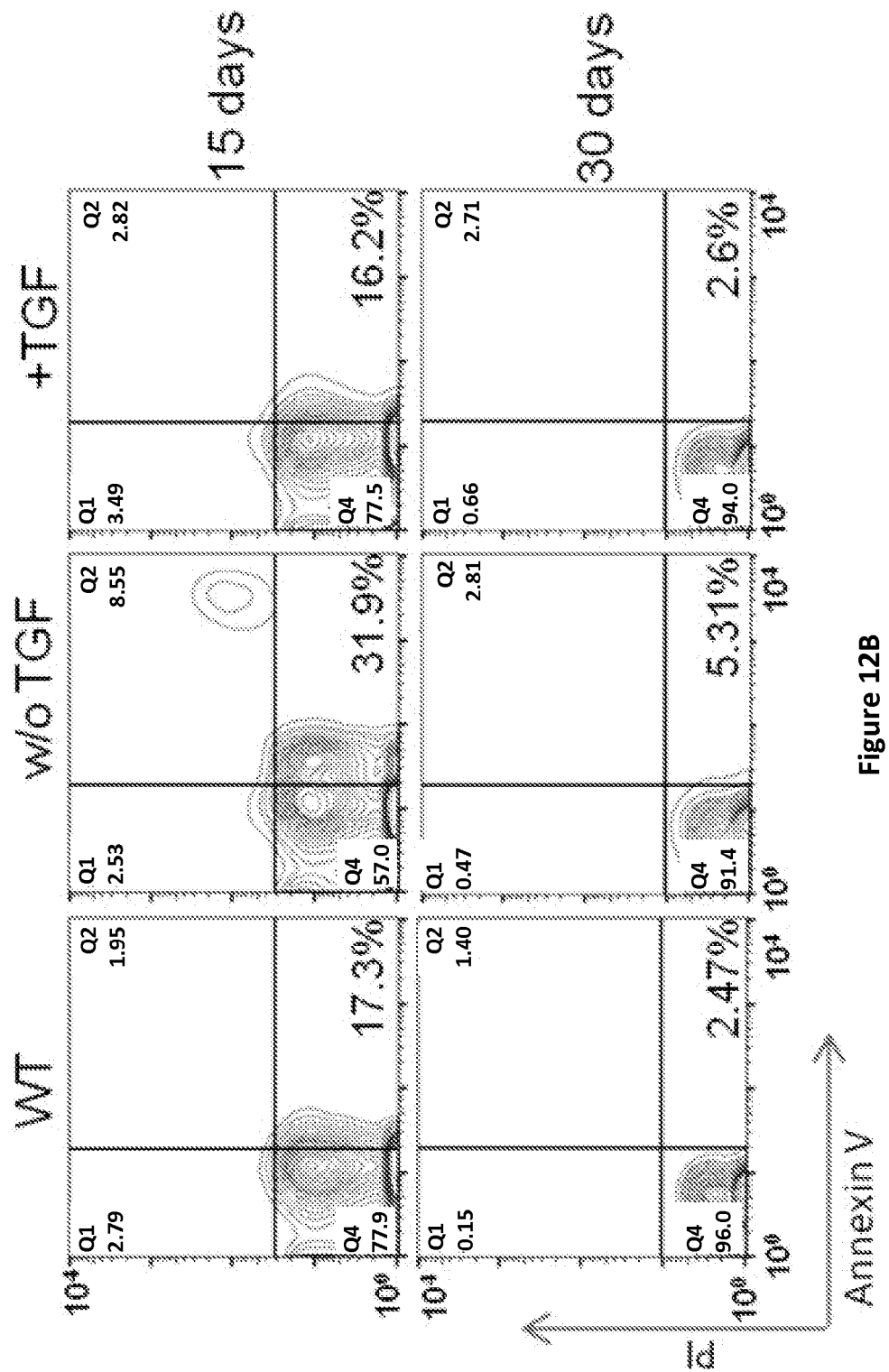
FIG. 12B shows FACS plots demonstrating that percentage of cytotoxic CD8+CD107+ T cells from total CD8+ cells is significantly higher when generated from hosts transplanted with TGF-β-lacking constructs, as compared with afTGF-3 constructs and WT mice.
Figure 12C:
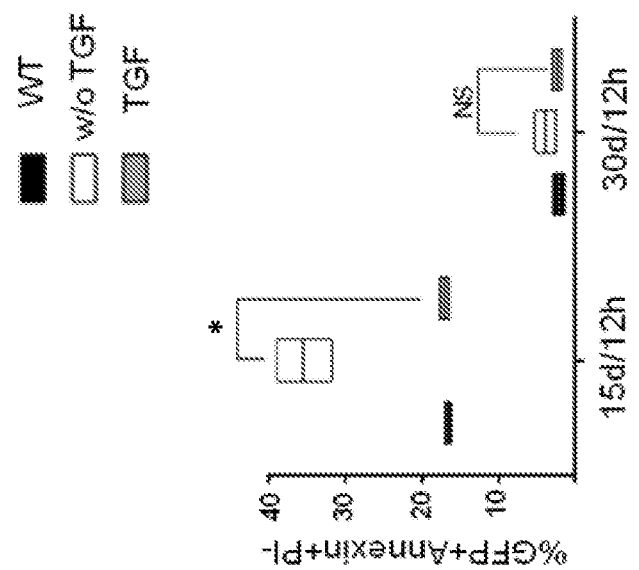
FIG. 12C shows a graph measuring percentage of apoptotic GFP+AnnexinV+PI-fibroblasts from total co-cultured fibroblasts after a cytotoxicity assay. Results represent the mean value of 3 triplicates and SEM of 2 separate experiments, compared by a two-way ANOVA. Tukey's post-hoc test was carried out to determine differences between the treatments. * $p<0.05$.

A FACS evaluation of the frequency of cytotoxic CD8 T cells expressing CD107 at 2 h and at 12 h after co-culturing the CD8 T cells with allofibroblasts indicated that, at both time points, the percentage of cytotoxic CD8+CD107+ T cells was significantly lower in splenocytes from mice transplanted with afTGF-β constructs than in splenocytes from mice transplanted with TGF-β-lacking constructs (FIG. 11F, 12A). Moreover, as compared with mice transplanted with TGF-β-lacking constructs, significantly fewer allofibroblasts underwent apoptosis when co-cultured with spleen-derived CD8 T cells isolated from mice transplanted with afTGF-β constructs (35.5%±5.1% vs. 17.2%±0.9%, respectively, at day 15; FIG. 12B, C). Notably, both the frequency and the cytotoxic activity of activated CD8 T cells obtained from mice transplanted with afTGF-β were similar to those in wild-type mice, indicating that the transplantation of allofibroblasts in the context of the TGF-β constructs elicited a very mild cytotoxic response.

We tested the hypothesis that local presentation of TGF-β as affinity-bound to matrix in a cell transplantation device promotes an immunoregulatory microenvironment, which protects cell allografts from being rejected. We show that afTGF-β exerts its regulatory functions by maintaining DCs in an immature phenotype and by increasing the frequency of Tregs and reducing the effector functions of CD4 and CD8 cytotoxic T cells in an IL-10-dependant manner. Importantly, we show that the local immunoregulatory effects of afTGF-β are projected to the spleen, which shows significantly reduced effector functions of allofibroblast-specific CD4 and CD8 T cells.

TGF-β is a key immunoregulatory cytokine, which, depending on the adjacent cytokine milieu, can drive both anti-inflammatory and pro-inflammatory responses.

Whether the presented TGF-β can regulate activated effector T cells when affinity-bound to the alginate scaffold is unclear. Our in vitro results indicate that afTGF-β suppresses the activation of CD4 T cells when DCs or, to a greater extent, when total splenocytes are used as antigen-presenting cells (APCs), and that it increases the levels of secreted IL-10 and the frequency of Tregs. Blocking experiments performed in vitro with anti-IL-10 or with CD11c-DNR splenocytes suggest that afTGF-β have a regulatory function in two pathways: (1) enhancing IL-10 signaling to DCs and maintaining their immature phenotype. Consequently, immature DCs reduce the effector function of T cells and increase the frequency of CD4+CD25+Foxp3+ Tregs, as was also observed in previous studies; and (2) it signals directly to effector T cells and attenuates their effector function.

Notably, afTGF-β is more effective than soluble TGF-β in a 2D culture. This phenomenon may be due to the local presentation of TGF-β to cells as affinity bound to the matrix, thereby, enhancing signal transduction. Furthermore, the affinity-binding of TGF-β resulted in prolonged sustained release of active cytokine, as compared to the rapid release when it was adsorbed to a pristine scaffold. Both of these mechanisms contribute to the successful generation of an immunoregulatory environment. TGF-β-controlled release systems have been used previously to induce and expand the population of Tregs in vitro and in vivo. However, none of these systems exploited affinity-binding of the cytokine or attempted to explore this strategy to create a 3D immunoregulatory environment that will facilitate its use as an allocell transplantation device.

As a transplantation device, the alginate scaffold was supplemented with the angiogenic factors VEGF and PDGF-β, which extensively enhance scaffold vascularization. A potential ramification of such a cell transplantation device is that, while vascularization is promoted to enable an efficient mass transport to and from the transplanted cells, enhanced leukocyte infiltration may facilitate allograft rejection. Our data show that afTGF-β exerts similar regulatory effects, as observed both in vitro and in vivo. As compared with TGF-β-lacking constructs, constructs with afTGF-β retrieved 10 and 15 days after transplantation showed a significantly reduced frequency of mature DCs, an increased frequency of Tregs, and a decreased frequency of cytotoxic T cells. Furthermore, mice transplanted with afTGF-β constructs also evoked peripheral tolerance, as splenocyte-derived allofibroblast reactive CD4 and CD8 T cells exhibited significantly reduced levels of pro-inflammatory cytokines and an almost completely abolished cytotoxic activity. Therefore, vascularization of the transplanted device not only increases the survival of the graft but also attenuates the peripheral immune reaction evoked in response to the transplanted cells, providing that TGF-β is presented locally within the scaffold.

We propose a 2-stage model to explain the unique properties of the afTGF-β constructs relative to the TGF-β-lacking constructs. In the first stage, afTGF-β signals to infiltrating APCs and maintains them in an immature state while they phagocytose the transplanted cells. Capillaries form within few days after transplantation, through which APCs migrate to the draining lymph nodes and then promote either anergy or mild activation of naïve allofibroblast-reactive CD4 and CD8 T cells. In the second stage, afTGF-β signaling to scaffold-infiltrating T cells, together with the presence of immature DCs, further attenuate DCs activation and promote Treg differentiation and/or expansion. These processes lead, overall, to significantly reduced allofibroblast cytotoxicity, observed at 15 and 30 days following the transplantation of the afTGF-β constructs.

As the alginate scaffold is eroded in the host, it is of great importance that the TGF-β-rich environment expands the local antigen-specific immunoregulation to systemic and antigen-specific immunotolerance. In the case of type-1 diabetes, for example, such peripheral tolerance evoked in response to transplanted β cells may allow blocking the immune attack in the pancreas and, perhaps, prevent islet regeneration. Similar strategies can be used to treat other tissue-specific autoimmune diseases, while avoiding compromising the host defense against pathogens, such as is the case of immuno-suppressive drugs.

Example 5

TGF-β Affinity-Bound to the Alginate/Sulfated Alginate Matrix (afTGF-β) for Treating Multiple Sclerosis (MS)

Experimental Autoimmune Encephalomyelitis (EAE) is used as a model of MS. C57BL6 mice are immunized with myelin oligodendrocyte glycoprotein (MOG) residues 35-55. 7-10 days later, mice develop tail and limb paralysis with progressing clinical scores. The disease is manifested by leukocyte infiltration into the spinal cord forming the typical lesions characteristics of MS. The disease often presents in a relapsing remitting fashion. Alginate/sulfated alginate scaffolds carrying or lacking TGF-β and MOG35-55 peptides are implanted either before or after immunization at different time points (e.g., day 5 before disease onset, day 15 at peak clinical score or day 20 at remission), and EAE clinical scores (as described in e.g. Miller et al., "Experimental Autoimmune Encephalomyelitis in the Mouse." *Curr Protoc Immunol.* 2007 May; CHAPTER: Unit-15.1, incorporated herein by reference) are examined along with the phenotype of MOG-specific CD4 T cells (cytokine profile and activation markers) and spinal cord histopathology i.e., infiltrating leukocytes and demyelination.

Results show that MOG-specific T cells are tolerated and hence prevent or ameliorate the acute and chronic disease process including reduction of EAE clinical scores, lymphocyte infiltration and decreased number of MS lesions in the animals receiving scaffolds carrying TGF-β and MOG35-55.

In clinical trials, TGFβ scaffolds carry several immunodominant epitopes depending on the specific HLA alleles in the subject with MS.

Example 6 afTGF-β for Treating Type I Diabetes

In a mouse model of type I diabetes (such as NOD mice) in which leukocytes destroy β cells in the pancreas, allogeneic or syngeneic pancreatic β cells expressing TGFβ are transplanted before or after disease onset (around 10 weeks), and insulin and glucose levels are examined in mice, along with immune infiltration, pathophysiology and β cell survival both in the scaffold and in the pancreas.

Results show that β cells-specific lymphocytes are tolerated, and hence prevent or ameliorate the acute and chronic disease process including reduction of β cells mortality, increase in insulin levels and reduction in blood glucose levels in the animals receiving pancreatic β cells expressing TGFβ.

What is claimed is:

1. A method for simultaneously inducing a peripheral and a localized immunotolerant response in a subject, the method comprising administering to said subject a composition comprising a sulfated polysaccharide and an immunoregulatory cytokine, wherein said immunoregulatory cytokine non-covalently associates with a sulfate group of the sulfated polysaccharide, and wherein said induction of a peripheral immunotolerant response comprises inhibiting peripheral antigen-specific leukocytes, wherein said immunoregulatory cytokine is selected from the group consisting of transforming growth factor β1 (TGFβ1), vascular endothelial growth factor (VEGF), and PDGF-ββ.

2. The method of claim 1, wherein said immunotolerant response comprises a reduction or prevention of an allograft rejection, an improvement in allograft success, a suppression of an immune response to an allocell transplantation, a suppression of allocell apoptosis, an increase in allocell survival, a stimulation of vascularization of an allocell transplant, or a combination thereof.

3. The method of claim 1, wherein said immunotolerant response comprises a suppression of inflammatory signaling, a suppression of dendritic cell maturation, a suppression of CD8+ T cell cytotoxicity response, a stimulation of regulatory T cell differentiation, or a combination thereof.

4. The method of claim 1, wherein said immunotolerant response comprises treatment or suppression of an autoimmune disorder.

5. The method of claim 4, wherein said autoimmune disease or disorder comprises multiple sclerosis, psoriasis, or type I diabetes.

6. The method of claim 5, wherein when said autoimmune disease or disorder is type I diabetes, said composition further comprises pancreatic beta-cells.

7. The method of claim 1, wherein said immunoregulatory cytokine comprises interleukin-10 (IL-10).

8. The method of claim 1, wherein said composition further comprises at least one additional bioactive polypeptide, wherein the at least one additional bioactive polypeptide non-covalently associates with a sulfate group of the sulfated polysaccharide.

9. The method of claim 8, wherein said at least one additional bioactive polypeptide comprises a positively-charged polypeptide, a heparin-binding polypeptide, a polypeptide exhibiting angiogenic activity, an autoantigen, or a combination thereof.

10. The method of claim 8, wherein said at least one additional bioactive polypeptide comprises antithrombin III (AT III), thrombopoietin (TPO), serine protease inhibitor (SLP1), C1 esterase inhibitor (C1 INH), Vaccinia virus complement control protein (VCP), a fibroblast growth factor (FGF), a FGF receptor, hepatocyte growth factor (HGF), insulin-like growth factor (IGF), a platelet-derived growth factor (PDGF), bone morphogenetic protein (BMP), epidermal growth factor (EGF), CXC chemokine ligand 4 (CXCL4), stromal cell-derived factor-1 (SDF-1), interleukin-6 (IL-6), interleukin-8 (IL-8), Regulated on Activation, Normal T Expressed and Secreted (RANTES), monocyte chemoattractant protein-1 (MCP-1), macrophage inflammatory peptide-1 (MIP-1), lymphotactin, fractalkine, an annexin, apolipoprotein E (ApoE), immunodeficiency virus type-1 (HIV-1) coat protein gp120, cyclophilin A (CypA), Tat protein, viral coat glycoprotein gC, gB or gD of herpes simplex virus (HSV), an envelope protein of Dengue virus, circumsporozoite (CS) protein of *Plasmodium falciparum*, bacterial surface adhesion protein OpaA, 1-selectin, P-selectin, heparin-binding growth-associated molecule (HB-GAM), thrombospondin type I repeat (TSR), amyloid P (AP), PDGF-AA, BMP-2, BMP-4, or BMP-7.

11. The method of claim 9, wherein said polypeptide exhibiting angiogenic activity is VEGF, bFGF, aFGF, IGF, HGF, BMP, or a combination thereof.

12. The method of claim 11, wherein said polypeptide exhibiting angiogenic activity comprises both VEGF and PDGF-ββ.

13. The method of claim 9, wherein said autoantigen comprises peptide myelin oligodendrocyte glycoprotein (MOG).

14. The method of claim 1, wherein said composition further comprises a supporting matrix.

15. The method of claim 14, wherein said supporting matrix is a polymer selected from the group consisting of a polysaccharide, a protein, an extracellular matrix component, a synthetic polymer, and a mixture thereof.

16. The method of claim 15, wherein said polysaccharide comprises a combination of alginate and sulfated alginate.

17. The method of claim 1, wherein said sulfated polysaccharide contains uronic acid residues.

18. The method of claim 1, wherein said sulfated polysaccharide is alginate sulfate or hyaluronan sulfate.

* * * * *